United States Patent
Rueger et al.

(10) Patent No.: US 10,364,292 B2
(45) Date of Patent: Jul. 30, 2019

(54) MONOVALENT BLOOD BRAIN BARRIER SHUTTLE MODULES

(71) Applicant: Hoffmann-La Roche Inc., Little Falls, NJ (US)

(72) Inventors: Petra Rueger, Penzberg (DE); Georg Tiefenthaler, Sindelsdorf (DE); Ekkehard Moessner, Kreuzlingen (CH); Jens Niewoehner, Munich (DE); Adrian Hugenmatter, Zurich (CH); Cuiying Shao, Shanghai (CN); Francesca Ros, Bernried (DE); Gang Xu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/203,057

(22) Filed: Jul. 6, 2016

(65) Prior Publication Data

US 2017/0051071 A1 Feb. 23, 2017

Related U.S. Application Data

(63) Continuation of application No. PCT/EP2014/079353, filed on Dec. 29, 2014.

(30) Foreign Application Priority Data

Jan. 6, 2014 (WO) ................ PCT/CN2014/070183

(51) Int. Cl.
*C07K 16/00* (2006.01)
*C07K 16/28* (2006.01)
*C07K 16/18* (2006.01)
*A61K 39/00* (2006.01)

(52) U.S. Cl.
CPC .......... *C07K 16/2881* (2013.01); *C07K 16/18* (2013.01); *A61K 2039/505* (2013.01); *C07K 2317/31* (2013.01); *C07K 2317/35* (2013.01); *C07K 2317/55* (2013.01); *C07K 2317/56* (2013.01); *C07K 2317/622* (2013.01); *C07K 2319/33* (2013.01)

(58) Field of Classification Search
None
See application file for complete search history.

(56) References Cited

U.S. PATENT DOCUMENTS

| | | |
|---|---|---|
| 2009/0162359 A1 | 6/2009 | Klein et al. |
| 2012/0171120 A1* | 7/2012 | Dennis ............ C07K 16/18 424/9.1 |

FOREIGN PATENT DOCUMENTS

| | | |
|---|---|---|
| EP | 2 708 560 A1 | 3/2014 |
| WO | WO 93/10819 A1 | 6/1993 |
| WO | WO 2007/044323 A2 | 4/2007 |
| WO | WO 2008/022349 A2 | 2/2008 |
| WO | 2010/115553 A1 | 10/2010 |
| WO | 2012/087835 A2 | 6/2012 |
| WO | WO 2012/075037 A1 | 6/2012 |
| WO | 2012/130831 A1 | 10/2012 |
| WO | WO 2012/143379 A1 | 10/2012 |
| WO | 2014/033074 A1 | 3/2014 |
| WO | 2014/189973 A2 | 11/2014 |

OTHER PUBLICATIONS

Weisser et al (Biotech Adv 27: 502-520, 2009).*
Boado, R.J., et al. Drug Targeting of Erythropoietin Across the Primate Blood Brain Barrier with an IgG Molecular Trojan Horse, J. Pharm. Exp. Ther. 333(3):961-69 (2010), 9 pages.
Boado, R.J., et al. Selective Targeting of a TNFR Decoy Receptor Pharmaceutical to the Primate Brain as a Receptor-Specific IgG Fusion Protein, J Biotechnol. 146(1-2):84-91(2010), 22 pages.
Boado, R.J., et al. Engineering and Expression of a Chimeric Transferrin Receptor Monoclonal Antibody for Blood-Brain Barrier Delivery in the Mouse, Biotechnol Bioeng. 102(4):1251-58 (2009), 19 pages.
Hust, M., et al. Single Chain Fab (scFab) Fragment, BMC Biotechnology 7:14 (2007), 15 pages.
Pardridge, W.M., Drug Transport Across the Blood-Brain Barrier, Journal of Cerebral Blood Flow & Metabolism 32:1959-72 (2012), 14 pages.
Yu, Y.J., and Watts, R.J., Developing Therapeutic Antibodies for Neurodegenerative Disease, Neurotherapeutics 10:459-72 (2013), 14 pages.
International Search Report prepared by the European Patent Office dated Apr. 8, 2015, for International Application No. PCT/EP2014/079353, 6 pages.
Written Opinion prepared by the European Patent Office for International Application No. PCT/EP2014/079353, 8 pages.

* cited by examiner

*Primary Examiner* — Daniel E Kolker
*Assistant Examiner* — Aditi Dutt
(74) *Attorney, Agent, or Firm* — Steven Cui

(57) ABSTRACT

Herein is reported a blood brain barrier shuttle module comprising a brain effector entity, a linker and one monovalent binding entity which binds to a blood brain barrier receptor, wherein the linker couples the effector entity to the monovalent binding entity which binds to the blood brain barrier receptor wherein the monovalent binding entity does not comprise the variable domains of the anti-transferrin receptor antibody 8D3 (SEQ ID NO: 01 and SEQ ID NO: 02) or of the variant anti-transferrin receptor antibody 8D3v (SEQ ID NO: 01 and SEQ ID NO: 03).

10 Claims, 1 Drawing Sheet
Specification includes a Sequence Listing.

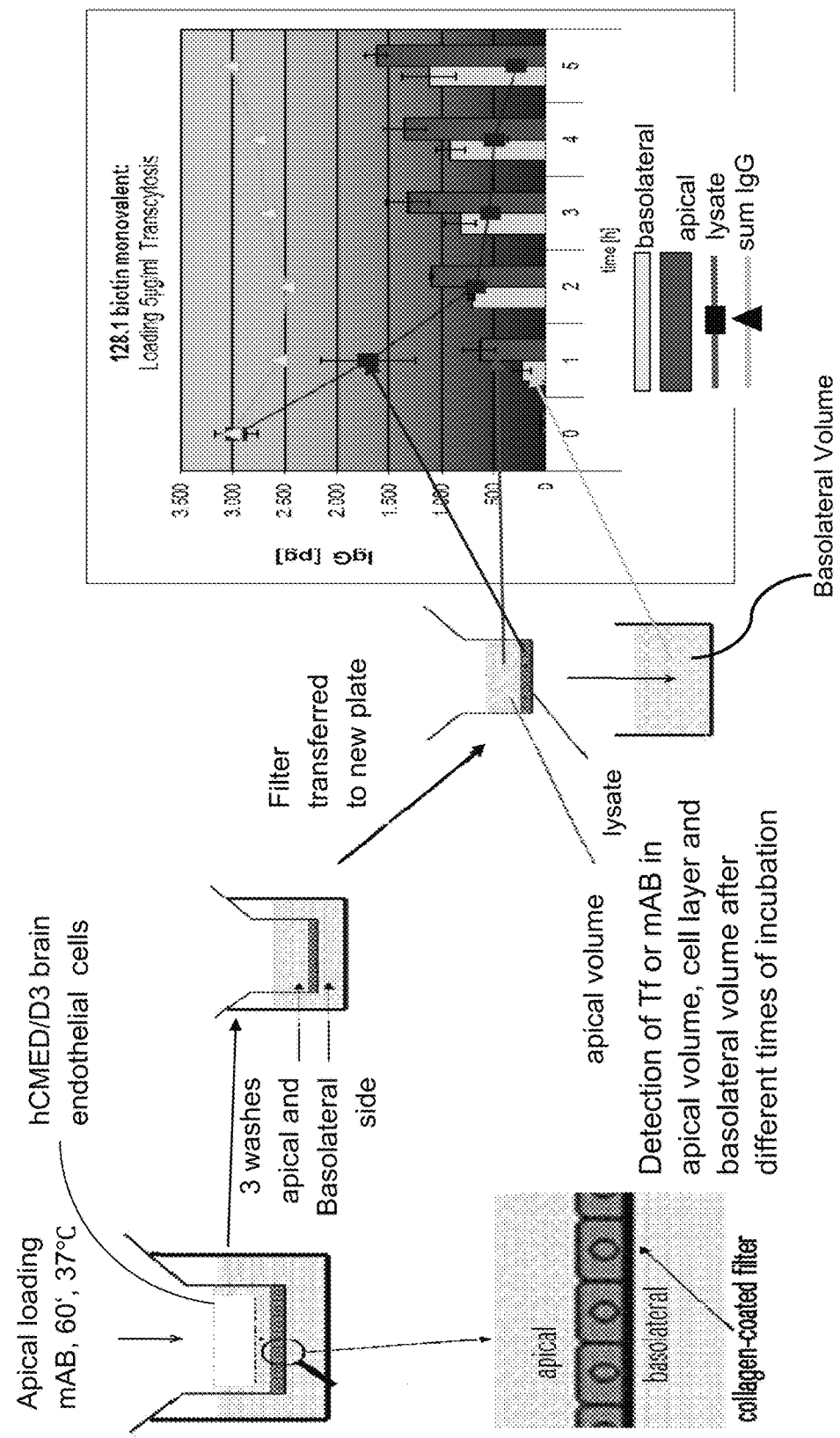

```
                            SEQUENCE LISTING

<160> NUMBER OF SEQ ID NOS: 122

<210> SEQ ID NO 1
<211> LENGTH: 118
<212> TYPE: PRT
<213> ORGANISM: Mus musculus

<400> SEQUENCE: 1

Glu Val Gln Leu Val Glu Ser Gly Gly Gly Leu Val Gln Pro Gly Asn
1               5                   10                  15

Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Met Asn Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser
        115

<210> SEQ ID NO 2
<211> LENGTH: 107
<212> TYPE: PRT
<213> ORGANISM: Mus musculus

<400> SEQUENCE: 2

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Leu Glu Leu Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: variant anti-transferrin receptor antibody 8D3v
      has a light chain variable domain with mutants L104V and L106I

<400> SEQUENCE: 3
```

```
Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Val Glu Ile Lys
            100                 105
```

<210> SEQ ID NO 4
<211> LENGTH: 15
<212> TYPE: PRT
<213> ORGANISM: Artificial Sequence
<220> FEATURE:
<223> OTHER INFORMATION: Epitope mapping peptide

<400> SEQUENCE: 4

```
Ile Gly Gln Asn Met Val Thr Ile Val Gln Ser Asn Gly Asn Leu
1               5                   10                  15
```

<210> SEQ ID NO 5
<211> LENGTH: 15
<212> TYPE: PRT
<213> ORGANISM: Artificial Sequence
<220> FEATURE:
<223> OTHER INFORMATION: Epitope mapping peptide

<400> SEQUENCE: 5

```
Asn Met Val Thr Ile Val Gln Ser Asn Gly Asn Leu Asp Pro Val
1               5                   10                  15
```

<210> SEQ ID NO 6
<211> LENGTH: 15
<212> TYPE: PRT
<213> ORGANISM: Artificial Sequence
<220> FEATURE:
<223> OTHER INFORMATION: Epitope mapping peptide

<400> SEQUENCE: 6

```
Gln Ser Asn Gly Asn Leu Asp Pro Val Glu Ser Pro Glu Gly Tyr
1               5                   10                  15
```

<210> SEQ ID NO 7
<211> LENGTH: 32
<212> TYPE: PRT
<213> ORGANISM: Artificial Sequence
<220> FEATURE:
<223> OTHER INFORMATION: Peptide linker

<400> SEQUENCE: 7

```
Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Ser Gly Gly
            20                  25                  30
```

<210> SEQ ID NO 8

```
<211> LENGTH: 20
<212> TYPE: PRT
<213> ORGANISM: Artificial Sequence
<220> FEATURE:
<223> OTHER INFORMATION: Peptide linker

<400> SEQUENCE: 8

Gly Gly Gly Gly Ser Gly Gly Gly Ser Gly Gly Gly Ser Gly
1               5                   10                  15

Gly Gly Gly Ser
            20

<210> SEQ ID NO 9
<211> LENGTH: 18
<212> TYPE: PRT
<213> ORGANISM: Artificial Sequence
<220> FEATURE:
<223> OTHER INFORMATION: peptidic linker

<400> SEQUENCE: 9

Gly Gly Ser Gly Gly Gly Ser Gly Gly Gly Ser Gly Gly Gly
1               5                   10                  15

Gly Ser

<210> SEQ ID NO 10
<211> LENGTH: 30
<212> TYPE: PRT
<213> ORGANISM: Artificial Sequence
<220> FEATURE:
<223> OTHER INFORMATION: peptidic linker

<400> SEQUENCE: 10

Gly Gly Gly Gly Ser Gly Gly Gly Gly Ser Gly Gly Gly Ser Gly
1               5                   10                  15

Gly Gly Ser Gly Gly Gly Gly Ser Gly Gly Gly Gly Ser
            20                  25                  30

<210> SEQ ID NO 11
<211> LENGTH: 137
<212> TYPE: PRT
<213> ORGANISM: Mus musculus

<400> SEQUENCE: 11

Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Ser Leu Asp Tyr Trp Gly
        115                 120                 125

Gln Gly Thr Ser Val Thr Val Ser Ser
    130                 135
```

-continued

```
<210> SEQ ID NO 12
<211> LENGTH: 128
<212> TYPE: PRT
<213> ORGANISM: Mus musculus

<400> SEQUENCE: 12

Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Ile Asp Tyr Ile His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Pro Glu Asp Ala Ala Thr Tyr Tyr Cys His Gln Arg
            100                 105                 110

Asn Ser Tyr Pro Trp Thr Phe Gly Gly Gly Thr Arg Leu Glu Ile Arg
        115                 120                 125

<210> SEQ ID NO 13
<211> LENGTH: 116
<212> TYPE: PRT
<213> ORGANISM: Artificial Sequence
<220> FEATURE:
<223> OTHER INFORMATION: clone 0128 VH

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Tyr
            20                  25                  30

Met Ser Trp Val Arg Gln Ala Pro Gly Lys Gly Leu Glu Trp Ile Gly
        35                  40                  45

Ile Ile Tyr Pro Ser Gly Tyr Ala Tyr Tyr Thr Ser Trp Ala Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Asp Val
                85                  90                  95

Gly Asp Gly Gly Gly Thr Phe Asp Ile Trp Gly Gln Gly Thr Met Val
            100                 105                 110

Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: clone 128 VL

<400> SEQUENCE: 14

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Thr Pro Tyr
                85                  90                  95

Thr Phe Gly Gln Gly Thr Lys Leu Glu Ile Lys Arg
            100                 105
```

<210> SEQ ID NO 15
<211> LENGTH: 121
<212> TYPE: PRT
<213> ORGANISM: Artificial Sequence
<220> FEATURE:
<223> OTHER INFORMATION: clone 0143 VH

<400> SEQUENCE: 15

```
Gly Val Gln Cys Gln Ser Leu Glu Glu Ser Gly Gly Arg Leu Val Thr
1               5                   10                  15

Pro Gly Gly Ser Leu Thr Leu Cys Thr Val Ser Gly Ile Asp Leu
            20                  25                  30

Ser Thr Tyr Ser Met Gly Trp Val Arg Gln Ser Pro Gly Lys Gly Leu
        35                  40                  45

Glu Tyr Ile Gly Ile Ile Ser Ser Asp Asn Thr Tyr Tyr Thr Ser
    50                  55                  60

Trp Ala Lys Gly Arg Phe Thr Ile Ser Lys Thr Ser Thr Val Asp
65                  70                  75                  80

Leu Lys Ile Thr Ser Pro Thr Thr Glu Asp Thr Ala Thr Tyr Phe Cys
                85                  90                  95

Ala Arg Gly Tyr Asn Gly Gly Trp Lys Thr Pro Met Asp Val Trp Gly
            100                 105                 110

Gln Arg Thr Thr Val Thr Val Ser Ser
            115                 120
```

<210> SEQ ID NO 16
<211> LENGTH: 108
<212> TYPE: PRT
<213> ORGANISM: Artificial Sequence
<220> FEATURE:
<223> OTHER INFORMATION: clone 0143 VL

<400> SEQUENCE: 16

```
Asp Ile Gln Met Thr Gln Ser Pro Ser Ser Leu Ser Val Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Glu Leu Leu Ile
        35                  40                  45

Tyr Ala Ala Ser Ile Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Thr Tyr Pro Pro
```

```
                    85                  90                  95

Thr Phe Gly Gln Gly Thr Lys Leu Glu Ile Lys Arg
                100                 105

<210> SEQ ID NO 17
<211> LENGTH: 129
<212> TYPE: PRT
<213> ORGANISM: Artificial Sequence
<220> FEATURE:
<223> OTHER INFORMATION: clone 0146 VH

<400> SEQUENCE: 17

Gly Val Gln Cys Glu Val Gln Leu Val Glu Ser Gly Gly Leu Val
1               5                   10                  15

Gln Pro Gly Gly Ser Leu Arg Leu Ser Cys Ala Ala Ser Gly Phe Thr
            20                  25                  30

Phe Gly Asp Phe Ala Met Asn Trp Val Arg Gln Ala Pro Gly Lys Gly
        35                  40                  45

Leu Glu Trp Val Ser Gly Ile Ser Ala Ser Gly Val Ser Thr Tyr Tyr
    50                  55                  60

Ala Asp Ser Val Lys Gly Arg Val Thr Ile Ser Arg Asp Asn Ser Lys
65                  70                  75                  80

Asn Thr Leu Asn Leu Gln Met Asn Ser Leu Arg Ala Glu Asp Thr Ala
                85                  90                  95

Val Tyr Tyr Cys Ala Arg Asp Pro Cys Asp Ala Ser Asn Asp Tyr Gly
            100                 105                 110

Tyr Cys Lys Leu Asp Val Trp Gly Gln Gly Thr Thr Val Thr Val Ser
        115                 120                 125

Ser

<210> SEQ ID NO 18
<211> LENGTH: 108
<212> TYPE: PRT
<213> ORGANISM: Artificial Sequence
<220> FEATURE:
<223> OTHER INFORMATION: clone 0146 VL

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys Arg
            100                 105

<210> SEQ ID NO 19
<211> LENGTH: 118
<212> TYPE: PRT
<213> ORGANISM: Artificial Sequence
<220> FEATURE:
<223> OTHER INFORMATION: clone 0279 VH
```

```
<400> SEQUENCE: 19

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Trp Ile Gly
        35                  40                  45

Tyr Ile Trp Ser Gly Gly Ser Ala Asp Tyr Ala Ser Trp Ala Lys Gly
    50                  55                  60

Arg Phe Thr Ile Ser Lys Thr Ser Thr Thr Val Asp Leu Lys Ile Pro
65                  70                  75                  80

Ser Pro Thr Met Glu Asp Thr Ala Thr Tyr Phe Cys Ala Arg Gly Asp
                85                  90                  95

Ala Glu Tyr Gly Asp Ala Asn Gly Phe Ala Ile Trp Gly Pro Gly Thr
            100                 105                 110

Leu Val Thr Val Ser Leu
            115

<210> SEQ ID NO 20
<211> LENGTH: 111
<212> TYPE: PRT
<213> ORGANISM: Artificial Sequence
<220> FEATURE:
<223> OTHER INFORMATION: clone 0279 VL

<400> SEQUENCE: 20

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Asp Phe Thr Leu Thr Ile Ser Gly Val Gly Cys
65                  70                  75                  80

Ala Asp Ala Ala Thr Tyr Tyr Cys Gln Gln Thr Leu Ser Thr Ile Asn
                85                  90                  95

Ile Asp Asn Thr Phe Gly Gly Gly Thr Glu Val Val Val Lys Arg
            100                 105                 110

<210> SEQ ID NO 21
<211> LENGTH: 122
<212> TYPE: PRT
<213> ORGANISM: Artificial Sequence
<220> FEATURE:
<223> OTHER INFORMATION: clone 0291 VH

<400> SEQUENCE: 21

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Gly Ala
            20                  25                  30

Met Thr Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60
```

```
Arg Phe Thr Ile Ser Lys Ser Thr Thr Val Asp Leu Lys Ile Thr
 65                  70                  75                  80

Ser Pro Thr Thr Glu Asp Thr Ala Thr Tyr Phe Cys Ala Arg Gly Tyr
                 85                  90                  95

Gly Ala Asp Tyr Pro Asp Phe Gly Asp Ala Asn Gly Phe Asp Pro Trp
            100                 105                 110

Gly Pro Gly Thr Leu Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: clone 0291 VL

<400> SEQUENCE: 22

Ala Tyr Asp Met Thr Gln Thr Pro Ala Ser Val Glu Val Ala Val Gly
 1               5                  10                  15

Gly Thr Val Thr Ile Lys Cys Gln Ala Ser Gln Ser Ile Ser Ser Tyr
             20                  25                  30

Leu Ala Trp Tyr Gln Gln Lys Pro Gly Gln Pro Pro Lys Leu Leu Ile
         35                  40                  45

Tyr Arg Ala Ser Thr Leu Ala Ser Gly Val Ser Ser Arg Phe Lys Gly
 50                  55                  60

Ser Gly Ser Gly Thr Gln Phe Thr Leu Thr Ile Ser Asp Leu Glu Cys
 65                  70                  75                  80

Ala Asp Ala Ala Thr Tyr Tyr Cys Gln Gln Gly Leu Ser Thr Ile Asn
                 85                  90                  95

Val Asp Asn Thr Phe Gly Gly Gly Thr Glu Val Val Val Lys Arg
            100                 105                 110

<210> SEQ ID NO 23
<211> LENGTH: 122
<212> TYPE: PRT
<213> ORGANISM: Artificial Sequence
<220> FEATURE:
<223> OTHER INFORMATION: clone 0299 VH

<400> SEQUENCE: 23

Gln Ser Met Glu Glu Ser Gly Gly Arg Leu Val Thr Pro Gly Thr Pro
 1               5                  10                  15

Leu Thr Leu Thr Cys Thr Val Ser Gly Phe Ser Leu Ser Ser Tyr Ala
             20                  25                  30

Met Ser Trp Val Arg Gln Ala Pro Gly Lys Gly Leu Glu Trp Ile Gly
         35                  40                  45

Tyr Ile Trp Ser Gly Gly Ser Thr Asp Tyr Ala Ser Trp Ala Lys Gly
 50                  55                  60

Arg Phe Thr Ile Ser Lys Ser Thr Thr Val Asp Leu Lys Ile Thr
 65                  70                  75                  80

Ser Pro Thr Thr Glu Asp Thr Ala Thr Tyr Phe Cys Ala Arg Arg Tyr
                 85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
        115                 120
```

```
<210> SEQ ID NO 24
<211> LENGTH: 111
<212> TYPE: PRT
<213> ORGANISM: Artificial Sequence
<220> FEATURE:
<223> OTHER INFORMATION: clone 0299 VL

<400> SEQUENCE: 24

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Cys Tyr Ser Ser Ser Asn
                85                  90                  95

Val Asp Asn Thr Phe Gly Gly Gly Thr Glu Val Val Val Lys Arg
            100                 105                 110

<210> SEQ ID NO 25
<211> LENGTH: 117
<212> TYPE: PRT
<213> ORGANISM: Artificial Sequence
<220> FEATURE:
<223> OTHER INFORMATION: clone 0300 VH

<400> SEQUENCE: 25

Gln Ser Val Glu Glu Ser Gly Gly Arg Leu Val Thr Pro Gly Thr Pro
1               5                   10                  15

Leu Thr Leu Thr Cys Thr Ala Ser Glu Phe Ser Leu Ser Asn Tyr Tyr
            20                  25                  30

Met Ser Trp Val Arg Gln Ala Pro Gly Lys Gly Leu Glu Tyr Ile Gly
        35                  40                  45

Phe Ile His Thr Asp Gly Ser Thr Asn Tyr Ala Ser Trp Val Asn Gly
50                  55                  60

Arg Phe Thr Ile Ser Arg Thr Ser Thr Thr Val Asp Leu Lys Thr Thr
65                  70                  75                  80

Ser Leu Thr Thr Glu Asp Thr Ala Thr Tyr Phe Cys Cys Arg Tyr Leu
                85                  90                  95

Val Ser Gly Gly Thr Ile Ala Phe Asp Leu Trp Gly Pro Gly Thr Leu
            100                 105                 110

Val Thr Val Ser Ser
        115

<210> SEQ ID NO 26
<211> LENGTH: 112
<212> TYPE: PRT
<213> ORGANISM: Artificial Sequence
<220> FEATURE:
<223> OTHER INFORMATION: clone 0300 VL

<400> SEQUENCE: 26

Ala Asp Val Val Met Thr Gln Thr Pro Ala Ser Val Glu Ala Ala Val
1               5                   10                  15

Gly Gly Thr Val Thr Ile Lys Cys Gln Ala Ser Gln Ser Ile Ser Ser
            20                  25                  30
```

```
Tyr Phe Ala Trp Tyr Gln Gln Lys Pro Gly Gln Pro Pro Lys Leu Leu
            35                  40                  45

Ile Tyr Arg Ala Ser Lys Leu Ala Thr Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Thr Cys Gly Ser Ile Ser
                85                  90                  95

Thr Tyr Gly Gly Ala Phe Gly Gly Thr Glu Val Val Val Lys Arg
                100                 105                 110
```

<210> SEQ ID NO 27
<211> LENGTH: 121
<212> TYPE: PRT
<213> ORGANISM: Artificial Sequence
<220> FEATURE:
<223> OTHER INFORMATION: clone 302 VH

<400> SEQUENCE: 27

```
Gln Ser Leu Glu Glu Ser Gly Gly Arg Leu Val Thr Pro Gly Gly Ser
1               5                   10                  15

Leu Thr Leu Thr Cys Thr Val Ser Gly Phe Ser Leu Ser Thr Tyr Ala
                20                  25                  30

Met Thr Trp Val Arg Gln Ala Pro Gly Lys Gly Leu Glu Trp Ile Gly
            35                  40                  45

Ile Ile Tyr Ala Gly Thr Asp Ile Thr Trp Tyr Ala Ser Trp Ala Lys
    50                  55                  60

Gly Arg Phe Thr Ile Ser Lys Thr Ser Thr Thr Val Asp Leu Ser Ile
65                  70                  75                  80

Thr Ser Pro Thr Thr Glu Asp Thr Ala Thr Tyr Phe Cys Ala Lys Val
                85                  90                  95

Pro Tyr Thr Gly Val Ser Asp Tyr Leu Tyr Tyr Phe Asp Leu Trp Gly
                100                 105                 110

Pro Gly Thr Leu Val Thr Val Ser Ser
        115                 120
```

<210> SEQ ID NO 28
<211> LENGTH: 111
<212> TYPE: PRT
<213> ORGANISM: Artificial Sequence
<220> FEATURE:
<223> OTHER INFORMATION: clone 0302 VL

<400> SEQUENCE: 28

```
Ala Phe Glu Met Thr Gln Thr Pro Ser Ser Val Ser Glu Pro Val Gly
1               5                   10                  15

Gly Thr Val Thr Ile Lys Cys Gln Ala Ser Glu Asn Ile Tyr Ser Phe
                20                  25                  30

Leu Ala Trp Tyr Gln Gln Lys Pro Gly Gln Pro Pro Lys Leu Leu Ile
            35                  40                  45

Tyr Asp Ala Ser Asp Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Gln Gly Tyr Ser Gly Asn Val
                85                  90                  95

Ile Leu Asn Ala Phe Gly Gly Gly Thr Glu Val Val Val Lys Arg
```

-continued

```
                    100                 105                 110

<210> SEQ ID NO 29
<211> LENGTH: 122
<212> TYPE: PRT
<213> ORGANISM: Artificial Sequence
<220> FEATURE:
<223> OTHER INFORMATION: clone 0304 VH

<400> SEQUENCE: 29

Gln Ser Met Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Arg Tyr
                85                  90                  95

Gly Thr Ser Tyr Pro Asp Tyr Gly Asp Ala Asn Gly Phe Asp Pro Trp
            100                 105                 110

Gly Pro Gly Thr Leu Val Thr Val Ser Ser
        115                 120

<210> SEQ ID NO 30
<211> LENGTH: 111
<212> TYPE: PRT
<213> ORGANISM: Artificial Sequence
<220> FEATURE:
<223> OTHER INFORMATION: clone 0304 VL

<400> SEQUENCE: 30

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Cys Tyr Ser Ser Ser Asn
                85                  90                  95

Val Asp Asn Thr Phe Gly Gly Gly Thr Glu Val Val Val Lys Arg
            100                 105                 110

<210> SEQ ID NO 31
<211> LENGTH: 118
<212> TYPE: PRT
<213> ORGANISM: Artificial Sequence
<220> FEATURE:
<223> OTHER INFORMATION: clone 0323 VH

<400> SEQUENCE: 31

Gln Ser Val Glu Glu Ser Gly Gly Arg Leu Val Thr Pro Gly Thr Pro
1               5                   10                  15
```

Leu Pro Leu Thr Cys Thr Val Ser Gly Phe Ser Leu Ser Asn Tyr Ala
            20                  25                  30

Met Gly Trp Phe Arg Gln Ala Pro Gly Lys Gly Leu Glu Trp Ile Gly
        35                  40                  45

Tyr Ile Trp Ser Gly Gly Ser Thr Asp Tyr Ala Ser Trp Ala Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Ala Asp
                85                  90                  95

Thr Val Tyr Arg Asp Asp Tyr Gly Trp Ser Leu Trp Gly Pro Gly Thr
            100                 105                 110

Leu Val Thr Val Ser Ser
            115

<210> SEQ ID NO 32
<211> LENGTH: 111
<212> TYPE: PRT
<213> ORGANISM: Artificial Sequence
<220> FEATURE:
<223> OTHER INFORMATION: clone 0323 VL

<400> SEQUENCE: 32

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ile Tyr
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Ala Tyr Ser Tyr Ser Asn
                85                  90                  95

Val Asp Asn Val Phe Gly Gly Gly Thr Glu Val Val Val Lys Arg
            100                 105                 110

<210> SEQ ID NO 33
<211> LENGTH: 120
<212> TYPE: PRT
<213> ORGANISM: Artificial Sequence
<220> FEATURE:
<223> OTHER INFORMATION: clone 0325 VH

<400> SEQUENCE: 33

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asn
            20                  25                  30

Met Gly Trp Val Arg Gln Ala Pro Gly Lys Gly Leu Glu Trp Ile Gly
        35                  40                  45

Ile Ile Ser Asp Ala Gly Ser Ala Trp Tyr Ala Ser Trp Val Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Ala Ala Thr Tyr Phe Cys Ala Arg Gly Asp

```
                85                  90                  95
Ala Ala Ala Tyr Thr Thr Gly Thr Glu Phe Phe Ser Leu Trp Gly Pro
            100                 105                 110

Gly Thr Leu Val Thr Val Ser Ser
        115                 120

<210> SEQ ID NO 34
<211> LENGTH: 111
<212> TYPE: PRT
<213> ORGANISM: Artificial Sequence
<220> FEATURE:
<223> OTHER INFORMATION: clone 0325 VL

<400> SEQUENCE: 34

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Arg Pro Lys Leu Leu Ile
        35                  40                  45

Tyr Ala Val Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Gln Cys
65                  70                  75                  80

Ala Asp Ala Ala Thr Tyr Tyr Cys Gln Gln Gly Tyr Ser Ser Ser Asn
                85                  90                  95

Leu Asp Asn Ala Phe Gly Gly Thr Glu Val Val Val Arg Arg
            100                 105                 110

<210> SEQ ID NO 35
<211> LENGTH: 120
<212> TYPE: PRT
<213> ORGANISM: Artificial Sequence
<220> FEATURE:
<223> OTHER INFORMATION: clone 0329 VH

<400> SEQUENCE: 35

Gly Val Gln Cys Gln Ser Leu Glu Glu Ser Gly Gly Gly Leu Val Lys
1               5                   10                  15

Pro Gly Gly Thr Leu Thr Leu Thr Cys Thr Val Ser Gly Phe Ser Leu
            20                  25                  30

Asn Ser Tyr Ser Met Thr Trp Val Arg Gln Ala Pro Gly Lys Gly Leu
        35                  40                  45

Glu Trp Ile Gly Tyr Ile Trp Ser Gly Gly Ser Ala Asp Tyr Ala Asn
    50                  55                  60

Trp Ala Lys Gly Arg Phe Thr Ile Ser Lys Thr Ser Thr Thr Val Asp
65                  70                  75                  80

Leu Lys Met Thr Ser Leu Thr Ala Glu Asp Thr Ala Thr Tyr Phe Cys
                85                  90                  95

Gly Arg Gly Tyr Asp Thr Thr Asp Asn Gly Phe Asn Leu Trp Gly Pro
            100                 105                 110

Gly Thr Leu Val Thr Val Ser Ser
        115                 120

<210> SEQ ID NO 36
<211> LENGTH: 111
<212> TYPE: PRT
<213> ORGANISM: Artificial Sequence
<220> FEATURE:
```

<223> OTHER INFORMATION: clone 0329 VL

<400> SEQUENCE: 36

Ala Tyr Asp Met Thr Gln Thr Pro Ala Ser Val Glu Ala Val Gly
1               5                   10                  15

Gly Thr Val Thr Ile Lys Cys Gln Ala Ser Gln Ser Ile Thr Ser Tyr
            20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Ser Ser Arg Phe Lys Gly
50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Thr Tyr Arg Tyr Met Asn
                85                  90                  95

Val Asp Asn Val Phe Gly Gly Gly Thr Glu Val Val Val Lys Arg
                100                 105                 110

<210> SEQ ID NO 37
<211> LENGTH: 123
<212> TYPE: PRT
<213> ORGANISM: Artificial Sequence
<220> FEATURE:
<223> OTHER INFORMATION: clone 0339 VH

<400> SEQUENCE: 37

Gly Val Gln Cys Gln Ser Val Glu Glu Ser Gly Gly Arg Leu Val Thr
1               5                   10                  15

Pro Gly Thr Pro Leu Thr Leu Thr Cys Thr Val Ser Gly Ile Asp Leu
            20                  25                  30

Ser Ser His Ala Met Thr Trp Val Arg Gln Ala Pro Gly Lys Gly Leu
            35                  40                  45

Glu Trp Ile Gly Tyr Ile Trp Ser Gly Gly Ser Ala Asp Tyr Ala Ser
            50                  55                  60

Trp Ala Lys Gly Arg Phe Thr Ile Ser Lys Thr Ser Ser Thr Thr Val
65                  70                  75                  80

Asp Leu Lys Ile Pro Ser Pro Thr Thr Glu Asp Thr Ala Thr Tyr Phe
                85                  90                  95

Cys Ala Arg Gly Ala Asp Glu Tyr Gly Asp Ala Asn Gly Phe Asn Ile
                100                 105                 110

Trp Gly Pro Gly Thr Leu Val Thr Val Ser Leu
            115                 120

<210> SEQ ID NO 38
<211> LENGTH: 111
<212> TYPE: PRT
<213> ORGANISM: Artificial Sequence
<220> FEATURE:
<223> OTHER INFORMATION: clone 0339 VL

<400> SEQUENCE: 38

Ala Tyr Asp Met Thr Gln Thr Pro Ser Ser Val Glu Ala Val Gly
1               5                   10                  15

Gly Thr Val Thr Ile Lys Cys Gln Ala Ser Gln Ser Ile Ser Asn Tyr
            20                  25                  30

Leu Ala Trp Tyr Gln Gln Lys Pro Gly Gln Pro Pro Glu Leu Leu Ile
            35                  40                  45

Tyr Arg Ala Ser Thr Leu Ala Ser Gly Val Ser Ser Arg Phe Arg Gly

```
                    50                  55                  60
Ser Gly Ser Gly Thr Asp Phe Thr Leu Thr Ile Ser Gly Val Gly Cys
 65                  70                  75                  80

Ala Asp Ala Ala Thr Tyr Tyr Cys Gln Gln Gly Leu Ser Ser Ser Tyr
                    85                  90                  95

Val Asp Asn Thr Phe Gly Gly Gly Thr Glu Val Val Val Lys Arg
                    100                 105                 110

<210> SEQ ID NO 39
<211> LENGTH: 123
<212> TYPE: PRT
<213> ORGANISM: Artificial Sequence
<220> FEATURE:
<223> OTHER INFORMATION: clone 0343 VH

<400> SEQUENCE: 39

Gly Val Gln Cys Gln Glu Gln Leu Lys Glu Ser Gly Gly Gly Leu Val
 1               5                  10                  15

Thr Pro Gly Thr Pro Leu Thr Leu Thr Cys Thr Ala Ser Gly Phe Ser
                    20                  25                  30

Leu Ser Ile Tyr Tyr Met Ser Trp Val Arg Gln Ala Pro Gly Lys Gly
                    35                  40                  45

Leu Asp Trp Ile Gly Phe Ile Tyr Val Asp Ser Ser Ser Ala His Tyr
                    50                  55                  60

Ala Ser Trp Ala Lys Gly Arg Phe Thr Ile Ser Lys Thr Ser Thr Thr
 65                  70                  75                  80

Val Asp Leu Lys Ile Thr Ser Pro Thr Thr Glu Asp Thr Ala Thr Tyr
                    85                  90                  95

Phe Cys Ala Arg Asp Val Asp Ser Ser Tyr Phe Trp Gly Phe Asn Leu
                    100                 105                 110

Trp Gly Pro Gly Thr Leu Val Thr Val Ser Ser
                    115                 120

<210> SEQ ID NO 40
<211> LENGTH: 112
<212> TYPE: PRT
<213> ORGANISM: Artificial Sequence
<220> FEATURE:
<223> OTHER INFORMATION: clone 0343 VL

<400> SEQUENCE: 40

Ala Asp Val Val Met Thr Gln Thr Pro Ser Pro Val Ser Gly Ala Val
 1               5                  10                  15

Gly Gly Thr Val Thr Ile Lys Cys Gln Ala Ser Gln Ser Ile Asp Ser
                    20                  25                  30

Tyr Leu Ser Trp Tyr Gln Gln Lys Pro Gly Gln Pro Pro Lys Leu Leu
                    35                  40                  45

Ile Tyr Ser Ala Ser Thr Leu Ala Ser Gly Val Ser Ser Arg Phe Lys
 50                  55                  60

Gly Ser Gly Ser Gly Thr Gln Phe Thr Leu Thr Ile Ser Asp Leu Glu
 65                  70                  75                  80

Cys Ala Asp Ala Ala Thr Tyr Tyr Cys Gln Cys Thr Tyr Tyr Asp Ser
                    85                  90                  95

Ser Ser Ile Gly Gly Phe Gly Gly Thr Glu Val Val Val Lys Arg
                    100                 105                 110

<210> SEQ ID NO 41
<211> LENGTH: 116
```

```
<212> TYPE: PRT
<213> ORGANISM: Artificial Sequence
<220> FEATURE:
<223> OTHER INFORMATION: clone 0346 VH

<400> SEQUENCE: 41

Gly Val Gln Cys Gln Ser Val Glu Glu Ser Gly Gly Arg Leu Val Thr
1               5                   10                  15

Pro Gly Thr Pro Leu Thr Leu Thr Cys Thr Val Ser Gly Phe Ser Leu
            20                  25                  30

Ser Ser Asn Ala Ile Asn Trp Val Arg Gln Ala Pro Gly Lys Gly Leu
        35                  40                  45

Glu Trp Ile Gly Tyr Ile Tyr Thr Asp Gly Asn Thr Tyr Tyr Ala Ser
    50                  55                  60

Trp Ala Lys Gly Arg Phe Thr Ile Ser Lys Thr Ser Thr Thr Val Asp
65                  70                  75                  80

Leu Lys Ile Thr Ser Pro Thr Thr Glu Asp Thr Ala Thr Tyr Phe Cys
                85                  90                  95

Ala Arg Gly Val Gly Tyr Ser Asp Leu Trp Gly Pro Gly Thr Leu Val
            100                 105                 110

Thr Val Ser Ser
            115

<210> SEQ ID NO 42
<211> LENGTH: 110
<212> TYPE: PRT
<213> ORGANISM: Artificial Sequence
<220> FEATURE:
<223> OTHER INFORMATION: clone 0346 VL

<400> SEQUENCE: 42

Asp Val Val Met Thr Gln Thr Pro Ser Ser Val Ser Glu Pro Val Gly
1               5                   10                  15

Gly Thr Val Thr Ile Asn Cys Gln Ala Ser Glu Asn Ile Tyr Ser Ser
            20                  25                  30

Leu Asp Trp Tyr Gln Gln Lys Pro Gly Gln Pro Pro Lys Leu Leu Ile
        35                  40                  45

Tyr Ser Ala Ser Asn Leu Ala Ser Gly Val Ser Ser Arg Phe Lys Gly
    50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Gln Cys Ile Asp Gly Gly Asn Arg
                85                  90                  95

Gly Lys Pro Phe Gly Gly Gly Thr Glu Val Val Val Lys Arg
            100                 105                 110

<210> SEQ ID NO 43
<211> LENGTH: 122
<212> TYPE: PRT
<213> ORGANISM: Artificial Sequence
<220> FEATURE:
<223> OTHER INFORMATION: clone 0348 VH

<400> SEQUENCE: 43

Gly Val Gln Cys Gln Ser Val Glu Glu Ser Gly Gly Arg Leu Val Thr
1               5                   10                  15

Pro Gly Thr Pro Leu Thr Leu Thr Cys Thr Ala Ser Gly Phe Ser Leu
            20                  25                  30

Asn Ser Val Tyr Met Ser Trp Val Arg Gln Ala Pro Gly Lys Gly Leu
```

```
                35                  40                  45
Glu Trp Ile Gly Ile Ile Tyr Ala Ser Gly Ser Ile Tyr Tyr Ala Ser
        50                  55                  60

Trp Ala Lys Gly Arg Phe Thr Ile Ser Arg Thr Ser Ser Thr Thr Val
65                  70                  75                  80

Asp Leu Lys Met Thr Ser Leu Thr Thr Glu Asp Thr Ala Thr Tyr Phe
                85                  90                  95

Cys Val Arg Ser Ala Asp Tyr Asp Ser Gly Met Pro Phe Asp Leu Trp
            100                 105                 110

Gly Pro Gly Thr Leu Val Thr Val Ser Ser
            115                 120

<210> SEQ ID NO 44
<211> LENGTH: 111
<212> TYPE: PRT
<213> ORGANISM: Artificial Sequence
<220> FEATURE:
<223> OTHER INFORMATION: clone 0348 VL

<400> SEQUENCE: 44

Ala Gln Val Leu Thr Gln Thr Ala Ser Ser Val Ser Ala Ala Val Gly
1               5                   10                  15

Gly Thr Val Thr Ile Ser Cys Gln Ser Ser Gln Ser Val Trp Asn Asn
            20                  25                  30

Asn Phe Leu Ser Trp Tyr Gln Gln Lys Pro Gly Gln Pro Pro Lys Leu
                35                  40                  45

Leu Ile Tyr Leu Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Val Tyr Ser Asp
                85                  90                  95

Asn Ile Phe Ala Phe Gly Gly Gly Thr Glu Val Val Val Lys Arg
            100                 105                 110

<210> SEQ ID NO 45
<211> LENGTH: 121
<212> TYPE: PRT
<213> ORGANISM: Artificial Sequence
<220> FEATURE:
<223> OTHER INFORMATION: clone 0349 VH

<400> SEQUENCE: 45

Gly Val Gln Cys Gln Ser Val Glu Glu Ser Gly Gly Arg Leu Val Thr
1               5                   10                  15

Pro Gly Thr Pro Leu Thr Leu Thr Cys Thr Val Ser Gly Phe Ser Leu
            20                  25                  30

Ser Ser Ser Tyr Met Ala Trp Val Arg Gln Ala Pro Gly Lys Gly Leu
                35                  40                  45

Glu Tyr Ile Gly Phe Ile His Thr Asp Gly Ser Thr Tyr Tyr Ala Thr
        50                  55                  60

Trp Val Asn Gly Arg Phe Thr Ile Ser Arg Thr Ser Thr Thr Val Thr
65                  70                  75                  80

Leu Lys Met Thr Ser Leu Thr Thr Glu Asp Thr Ala Thr Tyr Phe Cys
                85                  90                  95

Ala Arg Tyr Leu Val Gly Ser Gly Ala Val Ala Phe Asp Leu Trp Gly
            100                 105                 110
```

```
Pro Gly Thr Leu Val Thr Val Ser Ser
        115                 120

<210> SEQ ID NO 46
<211> LENGTH: 112
<212> TYPE: PRT
<213> ORGANISM: Artificial Sequence
<220> FEATURE:
<223> OTHER INFORMATION: clone 0349 VL

<400> SEQUENCE: 46

Ala Asp Val Val Met Thr Gln Thr Pro Ala Ser Val Glu Ala Ala Val
1               5                   10                  15

Gly Gly Thr Val Thr Ile Lys Cys Gln Ala Ser Gln Ser Ile Ser Ser
            20                  25                  30

Tyr Phe Ala Trp Tyr Gln Gln Lys Pro Gly Gln Pro Pro Lys Leu Leu
        35                  40                  45

Ile Tyr Arg Ala Ser Asn Leu Ala Thr Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Ser Cys Gly Ser Ile Ser
                85                  90                  95

Thr Tyr Gly Gly Ala Phe Gly Gly Gly Thr Glu Val Val Val Lys Arg
            100                 105                 110

<210> SEQ ID NO 47
<211> LENGTH: 121
<212> TYPE: PRT
<213> ORGANISM: Artificial Sequence
<220> FEATURE:
<223> OTHER INFORMATION: clone 0350 VH

<400> SEQUENCE: 47

Gly Val Gln Cys Gln Ser Val Glu Glu Ser Gly Gly Arg Leu Val Thr
1               5                   10                  15

Pro Gly Thr Pro Leu Thr Leu Thr Cys Thr Val Ser Gly Phe Ser Leu
            20                  25                  30

Ser Ser Tyr Ala Met Gly Trp Val Arg Gln Ala Pro Gly Lys Gly Leu
        35                  40                  45

Glu Trp Ile Gly Tyr Ile Trp Ser Gly Gly Ser Thr Asp Tyr Ala Thr
    50                  55                  60

Trp Ala Lys Gly Arg Phe Thr Ile Ser Lys Thr Ser Thr Thr Val Asp
65                  70                  75                  80

Leu Ser Ile Thr Ser Pro Thr Thr Glu Asp Thr Ala Ala Tyr Phe Cys
                85                  90                  95

Val Arg Ser Ala Gly Ser Gly Asp Ala Met Gly Phe Asn Leu Trp Gly
            100                 105                 110

Pro Gly Thr Leu Val Thr Val Ser Ser
        115                 120

<210> SEQ ID NO 48
<211> LENGTH: 111
<212> TYPE: PRT
<213> ORGANISM: Artificial Sequence
<220> FEATURE:
<223> OTHER INFORMATION: clone 0350 VL

<400> SEQUENCE: 48

Ala Tyr Asp Met Thr Gln Thr Pro Ala Ser Val Ser Glu Pro Val Gly
```

```
1               5                   10                  15
Gly Thr Val Thr Ile Lys Cys Gln Ala Ser Gln Ser Ile Ser Ser Tyr
                20                  25                  30

Leu Ser Trp Tyr Gln Gln Lys Pro Gly Gln Pro Lys Leu Leu Ile
            35                  40                  45

Tyr Arg Ala Ser Thr Leu Glu Ser Gly Val Pro Ser Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gln Gly Leu Ser Val Ile His
                85                  90                  95

Val Asp Asn Thr Phe Gly Gly Gly Thr Glu Val Val Val Lys Arg
                100                 105                 110
```

<210> SEQ ID NO 49
<211> LENGTH: 122
<212> TYPE: PRT
<213> ORGANISM: Artificial Sequence
<220> FEATURE:
<223> OTHER INFORMATION: clone 0411 VH

<400> SEQUENCE: 49

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
                20                  25                  30

Met Thr Trp Val Arg Gln Ala Pro Gly Lys Gly Leu Glu Trp Ile Gly
            35                  40                  45

Tyr Ile Trp Ser Gly Gly Ser Thr Asp Tyr Ala Thr Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Tyr
                85                  90                  95

Gly Ala Gly Tyr Pro Asp Tyr Gly Asp Ala Asn Gly Phe Asp Pro Trp
                100                 105                 110

Gly Pro Gly Thr Leu Val Thr Val Ser Ser
            115                 120
```

<210> SEQ ID NO 50
<211> LENGTH: 111
<212> TYPE: PRT
<213> ORGANISM: Artificial Sequence
<220> FEATURE:
<223> OTHER INFORMATION: clone 0411 VL

<400> SEQUENCE: 50

```
Ala Tyr Asp Met Thr Gln Thr Pro Ala Ser Val Ser Ala Ala Val Gly
1               5                   10                  15

Gly Thr Val Ser Ile Asn Cys Gln Ala Ser Gln Ser Ile Ser Gly Tyr
                20                  25                  30

Leu Ser Trp Tyr Gln Gln Lys Pro Gly Gln Arg Pro Lys Leu Leu Ile
            35                  40                  45

Tyr Arg Ala Ser Thr Leu Ala Ser Gly Val Ser Ser Arg Phe Lys Gly
        50                  55                  60

Ser Gly Ser Gly Thr Gln Phe Thr Leu Thr Ile Ser Gly Val Glu Cys
65                  70                  75                  80
```

-continued

```
Ala Asp Ala Ala Thr Tyr Tyr Cys Gln Gln Gly Tyr Ser Ile Ile Asn
                85                  90                  95

Val Asp Asn Thr Phe Gly Gly Gly Thr Glu Val Val Val Lys Arg
            100                 105                 110

<210> SEQ ID NO 51
<211> LENGTH: 120
<212> TYPE: PRT
<213> ORGANISM: Artificial Sequence
<220> FEATURE:
<223> OTHER INFORMATION: clone 0431 VH

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Ser Ser Tyr Ile Ser Gly Phe Asp Tyr Trp Gly Gln
            100                 105                 110

Gly Thr Leu Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: clone 0431 VL

<400> SEQUENCE: 52

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asp Tyr Gly Asp Gly
                85                  90                  95

Val Phe Gly Gly Gly Thr Lys Leu Thr Val Leu
            100                 105

<210> SEQ ID NO 53
<211> LENGTH: 120
<212> TYPE: PRT
<213> ORGANISM: Artificial Sequence
<220> FEATURE:
<223> OTHER INFORMATION: clone 0432 VH
```

```
<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Ser Trp Trp Leu Ser Gly Leu Asp Tyr Trp Gly Gln
            100                 105                 110

Gly Thr Leu Val Thr Val Ser Ser
        115                 120

<210> SEQ ID NO 54
<211> LENGTH: 107
<212> TYPE: PRT
<213> ORGANISM: Artificial Sequence
<220> FEATURE:
<223> OTHER INFORMATION: clone 0432 VL

<400> SEQUENCE: 54

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Met Thr Glu Ser Met Asn Tyr
                85                  90                  95

Val Phe Gly Gly Gly Thr Lys Leu Thr Val Leu
            100                 105

<210> SEQ ID NO 55
<211> LENGTH: 120
<212> TYPE: PRT
<213> ORGANISM: Artificial Sequence
<220> FEATURE:
<223> OTHER INFORMATION: clone 0433 VH

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60
```

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Ser Thr Trp Phe Ser Gly Phe Asp Tyr Trp Gly Gln
            100                 105                 110

Gly Thr Leu Val Thr Val Ser Ser
            115                 120

<210> SEQ ID NO 56
<211> LENGTH: 108
<212> TYPE: PRT
<213> ORGANISM: Artificial Sequence
<220> FEATURE:
<223> OTHER INFORMATION: clone 0433 VL

<400> SEQUENCE: 56

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asp Ser Ser Gly Asn His
                85                  90                  95

Asp Val Phe Gly Gly Gly Thr Lys Leu Thr Val Leu
            100                 105

<210> SEQ ID NO 57
<211> LENGTH: 120
<212> TYPE: PRT
<213> ORGANISM: Artificial Sequence
<220> FEATURE:
<223> OTHER INFORMATION: clone 0434 VH

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Pro Trp Tyr Ile Trp Ser Tyr Asp Tyr Trp Gly Gln
            100                 105                 110

Gly Thr Leu Val Thr Val Ser Ser
            115                 120

<210> SEQ ID NO 58
```

```
<211> LENGTH: 108
<212> TYPE: PRT
<213> ORGANISM: Artificial Sequence
<220> FEATURE:
<223> OTHER INFORMATION: clone 0434 VL

<400> SEQUENCE: 58

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Pro Asp Ser Ile Ala Tyr Gly
                85                  90                  95

Val Val Phe Gly Gly Gly Thr Lys Leu Thr Val Leu
            100                 105

<210> SEQ ID NO 59
<211> LENGTH: 119
<212> TYPE: PRT
<213> ORGANISM: Artificial Sequence
<220> FEATURE:
<223> OTHER INFORMATION: clone 0435 VH

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Phe Leu Ser Gly Phe Asp Tyr Trp Gly Gln Gly
            100                 105                 110

Thr Ile Val Thr Val Ser Ser
        115

<210> SEQ ID NO 60
<211> LENGTH: 107
<212> TYPE: PRT
<213> ORGANISM: Artificial Sequence
<220> FEATURE:
<223> OTHER INFORMATION: clone 0435 VL

<400> SEQUENCE: 60

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30
```

```
Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Glu Asp Ser Glu Ser Asn Leu
                 85                  90                  95

Val Phe Gly Gly Gly Thr Lys Leu Thr Val Leu
                100                 105

<210> SEQ ID NO 61
<211> LENGTH: 118
<212> TYPE: PRT
<213> ORGANISM: Artificial Sequence
<220> FEATURE:
<223> OTHER INFORMATION: clone 0441 VH

<400> SEQUENCE: 61

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Trp Phe Gly Glu Trp Met Asp Tyr Trp Gly Gln Gly Thr
                100                 105                 110

Leu Val Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: clone 0441 VL

<400> SEQUENCE: 62

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ile Asp Ser Ala Leu Asp His
                 85                  90                  95

Val Phe Gly Gly Gly Thr Lys Leu Thr Val Leu
                100                 105
```

<210> SEQ ID NO 63
<211> LENGTH: 119
<212> TYPE: PRT
<213> ORGANISM: Artificial Sequence
<220> FEATURE:
<223> OTHER INFORMATION: clone 0445 VH

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Trp Tyr Gly Trp Ala Phe Asp Tyr Trp Gly Gln Gly
            100                 105                 110

Thr Leu Val Thr Val Ser Ser
        115

<210> SEQ ID NO 64
<211> LENGTH: 107
<212> TYPE: PRT
<213> ORGANISM: Artificial Sequence
<220> FEATURE:
<223> OTHER INFORMATION: clone 0445 VL

<400> SEQUENCE: 64

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Met Ser Leu Asn Val
                85                  90                  95

Val Phe Gly Gly Gly Thr Lys Leu Thr Val Leu
            100                 105

<210> SEQ ID NO 65
<211> LENGTH: 119
<212> TYPE: PRT
<213> ORGANISM: Artificial Sequence
<220> FEATURE:
<223> OTHER INFORMATION: clone 0447 VH

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Phe Tyr Gly Trp Ala Phe Asp Tyr Trp Gly Gln Gly
                100                 105                 110

Thr Leu Val Thr Val Ser Ser
            115

<210> SEQ ID NO 66
<211> LENGTH: 108
<212> TYPE: PRT
<213> ORGANISM: Artificial Sequence
<220> FEATURE:
<223> OTHER INFORMATION: clone 0447 VL

<400> SEQUENCE: 66

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Thr Leu Ile Val
                85                  90                  95

Val Val Phe Gly Gly Gly Thr Lys Leu Thr Val Leu
                100                 105

<210> SEQ ID NO 67
<211> LENGTH: 119
<212> TYPE: PRT
<213> ORGANISM: Artificial Sequence
<220> FEATURE:
<223> OTHER INFORMATION: clone 0449 VH

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Trp Gly Trp Val Ala Phe Asp Tyr Trp Gly Gln Gly
            100                 105                 110

Thr Leu Val Thr Val Ser Ser
        115

<210> SEQ ID NO 68
<211> LENGTH: 108
<212> TYPE: PRT
<213> ORGANISM: Artificial Sequence
<220> FEATURE:
<223> OTHER INFORMATION: clone 0449 VL

<400> SEQUENCE: 68

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Pro Asp Ser Ser Val Asn Tyr
                85                  90                  95

Met Val Phe Gly Gly Gly Thr Lys Leu Thr Val Leu
            100                 105

<210> SEQ ID NO 69
<211> LENGTH: 120
<212> TYPE: PRT
<213> ORGANISM: Artificial Sequence
<220> FEATURE:
<223> OTHER INFORMATION: clone 0451 VH

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Tyr Tyr Tyr Leu Ser Gly Phe Asp Tyr Trp Gly Gln
            100                 105                 110

Gly Thr Leu Val Thr Val Ser Ser
        115                 120

<210> SEQ ID NO 70
<211> LENGTH: 107
<212> TYPE: PRT
<213> ORGANISM: Artificial Sequence
<220> FEATURE:
<223> OTHER INFORMATION: clone 0451 VL

<400> SEQUENCE: 70

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Ile Thr Ile Thr Gly Ala Gln Ala Glu
65                  70                  75                  80

Asp Glu Ala Asp Tyr Tyr Cys Asn Ser Arg Asp Ile Ile Gly Asp Ala
                85                  90                  95

Val Phe Gly Gly Gly Thr Lys Leu Thr Val Leu
            100                 105

<210> SEQ ID NO 71
<211> LENGTH: 120
<212> TYPE: PRT
<213> ORGANISM: Artificial Sequence
<220> FEATURE:
<223> OTHER INFORMATION: clone 0452 VH

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Trp Asp Tyr Leu Ser Ser Met Asp Tyr Trp Gly Gln
            100                 105                 110

Gly Thr Leu Val Thr Val Ser Ser
        115                 120

<210> SEQ ID NO 72
<211> LENGTH: 108
<212> TYPE: PRT
<213> ORGANISM: Artificial Sequence
<220> FEATURE:
<223> OTHER INFORMATION: clone 0452 VL

<400> SEQUENCE: 72

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

```
Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ile Asp Ser Glu Gly Asn Asp
                 85                  90                  95

Ile Val Phe Gly Gly Gly Thr Lys Leu Thr Val Leu
            100                 105

<210> SEQ ID NO 73
<211> LENGTH: 117
<212> TYPE: PRT
<213> ORGANISM: Artificial Sequence
<220> FEATURE:
<223> OTHER INFORMATION: clone 0453 VH

<400> SEQUENCE: 73

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Val Tyr Gly His Leu Asp Tyr Trp Gly Gln Gly Thr Leu
                100                 105                 110

Val Thr Val Ser Ser
            115

<210> SEQ ID NO 74
<211> LENGTH: 107
<212> TYPE: PRT
<213> ORGANISM: Artificial Sequence
<220> FEATURE:
<223> OTHER INFORMATION: clone 0453 VL

<400> SEQUENCE: 74

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ile Asp Leu Ser Met Asp Ile
                 85                  90                  95

Val Phe Gly Gly Gly Thr Lys Leu Thr Val Leu
            100                 105

<210> SEQ ID NO 75
<211> LENGTH: 121
<212> TYPE: PRT
```

<213> ORGANISM: Artificial Sequence
<220> FEATURE:
<223> OTHER INFORMATION: clone 0486 VH

<400> SEQUENCE: 75

| Glu | Val | Gln | Leu | Gln | Gln | Ser | Gly | Pro | Glu | Leu | Glu | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Ile | Ser | Cys | Lys | Ala | Ser | Gly | Tyr | Ser | Phe | Thr | Gly | Tyr |
|---|---|---|---|---|---|---|---|---|---|---|---|---|---|---|---|
| | | | 20 | | | | | 25 | | | | | 30 | | |

| Asn | Met | Asn | Trp | Val | Lys | Gln | Ser | Asn | Gly | Glu | Arg | Leu | Glu | Trp | Ile |
|---|---|---|---|---|---|---|---|---|---|---|---|---|---|---|---|
| | | 35 | | | | | 40 | | | | | 45 | | | |

| Gly | Ser | Ile | Asp | Pro | Phe | Tyr | Gly | Gly | Thr | Tyr | Asn | Gln | Lys | Phe |
|---|---|---|---|---|---|---|---|---|---|---|---|---|---|---|
| 50 | | | | | 55 | | | | | 60 | | | | |

| Lys | Asp | Lys | Ala | Thr | Leu | Thr | Val | Asp | Lys | Pro | Ser | Ser | Thr | Ala | Tyr |
|---|---|---|---|---|---|---|---|---|---|---|---|---|---|---|---|
| 65 | | | | | 70 | | | | | 75 | | | | | 80 |

| Met | Gln | Leu | Thr | Ser | Leu | Thr | Ala | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Gly | Gly | Asn | Tyr | Tyr | Gly | Pro | Trp | Phe | Ala | Tyr | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ala |
|---|---|---|---|---|---|---|---|---|
| | | 115 | | | | | 120 | |

<210> SEQ ID NO 76
<211> LENGTH: 113
<212> TYPE: PRT
<213> ORGANISM: Artificial Sequence
<220> FEATURE:
<223> OTHER INFORMATION: clone 0486 VL

<400> SEQUENCE: 76

| Asp | Val | Leu | Met | Thr | Gln | Thr | Pro | Leu | Ser | Leu | Pro | Val | Ser | Leu | Gly |
|---|---|---|---|---|---|---|---|---|---|---|---|---|---|---|---|
| 1 | | | | 5 | | | | | 10 | | | | | 15 | |

| Asp | Gln | Ala | Ser | Ile | Ser | Cys | Arg | Ser | Thr | Gln | Ser | Val | Val | His | Ser |
|---|---|---|---|---|---|---|---|---|---|---|---|---|---|---|---|
| | | | 20 | | | | | 25 | | | | | 30 | | |

| Asp | Gly | Ile | Thr | His | Leu | Glu | Trp | Tyr | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Lys | Leu | Leu | Ile | Tyr | Lys | Val | Phe | Asn | Arg | Phe | Tyr | Gly | Val | Pro |
|---|---|---|---|---|---|---|---|---|---|---|---|---|---|---|---|
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Leu | Gly | Val | Tyr | Tyr | Cys | Phe | Gln | Gly |
|---|---|---|---|---|---|---|---|---|---|---|---|---|---|---|---|
| | | | | 85 | | | | | 90 | | | | | 95 | |

| Ser | His | Val | Pro | Trp | Thr | Phe | Gly | Gly | Gly | Thr | Lys | Leu | Glu | Ile | Lys |
|---|---|---|---|---|---|---|---|---|---|---|---|---|---|---|---|
| | | | 100 | | | | | 105 | | | | | 110 | | |

Arg

<210> SEQ ID NO 77
<211> LENGTH: 121
<212> TYPE: PRT
<213> ORGANISM: Artificial Sequence
<220> FEATURE:
<223> OTHER INFORMATION: clone 0487 VH

<400> SEQUENCE: 77

| Asp | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Arg | Lys | Leu | Ser | Cys | Ala | Ala | Ser | Gly | Phe | Thr | Phe | Ser | Ser | Phe |
|---|---|---|---|---|---|---|---|---|---|---|---|---|---|---|---|
| | | | 20 | | | | | 25 | | | | | 30 | | |

```
Gly Met His Trp Val Arg Gln Ala Pro Glu Lys Gly Leu Glu Trp Val
            35                  40                  45

Ala Tyr Ile Ser Ser Gly Ser Gly Thr Ile Tyr Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Thr Leu Arg Ser Glu Asp Thr Ala Met Tyr Tyr Cys
                85                  90                  95

Ala Arg Ser Tyr Tyr Ser Asp Phe Gly His Ala Met Asp Tyr Trp Gly
            100                 105                 110

Gln Gly Thr Ser Val Thr Val Ser Ser
            115                 120

<210> SEQ ID NO 78
<211> LENGTH: 113
<212> TYPE: PRT
<213> ORGANISM: Artificial Sequence
<220> FEATURE:
<223> OTHER INFORMATION: clone 0487 VL

<400> SEQUENCE: 78

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Tyr Thr
            20                  25                  30

Ile Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ser
                85                  90                  95

Thr His Phe Pro Leu Thr Phe Gly Ala Gly Thr Lys Leu Glu Leu Arg
            100                 105                 110

Arg

<210> SEQ ID NO 79
<211> LENGTH: 119
<212> TYPE: PRT
<213> ORGANISM: Artificial Sequence
<220> FEATURE:
<223> OTHER INFORMATION: clone 0488 VH

<400> SEQUENCE: 79

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Thr Phe
            20                  25                  30

Gly Met His Trp Val Arg Gln Thr Pro Glu Arg Gly Leu Glu Trp Val
            35                  40                  45

Ala Tyr Ile Ser Ser Gly Gly Thr Asn Ile Tyr Tyr Ala Asp Pro Val
 50                  55                  60

Lys Gly Arg Phe Thr Ile Ser Arg Asp Asn Pro Lys Lys Thr Leu Phe
 65                  70                  75                  80

Leu Gln Met Thr Gly Leu Arg Ser Glu Asp Thr Ala Ile Tyr Tyr Cys
                85                  90                  95
```

```
Ala Arg Asp Gly Phe Gly Asn Tyr Trp Phe Ala Tyr Trp Gly Gln Gly
            100                 105                 110

Thr Leu Val Thr Val Ser Ala
        115
```

<210> SEQ ID NO 80
<211> LENGTH: 108
<212> TYPE: PRT
<213> ORGANISM: Artificial Sequence
<220> FEATURE:
<223> OTHER INFORMATION: clone 0488 VL

<400> SEQUENCE: 80

```
Asp Ile Gln Met Thr Gln Ser Pro Ala Ser Leu Ser Ala Thr Val Gly
1               5                   10                  15

Glu Thr Val Thr Ile Thr Cys Arg Thr Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Gly Gln Thr Leu Ala Glu Gly Val Pro Ser Lys Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Phe Cys His Gln Tyr Phe Tyr Pro Pro Leu
                85                  90                  95

Thr Phe Gly Thr Gly Thr Lys Leu Glu Ile Lys Arg
            100                 105
```

<210> SEQ ID NO 81
<211> LENGTH: 120
<212> TYPE: PRT
<213> ORGANISM: Artificial Sequence
<220> FEATURE:
<223> OTHER INFORMATION: clone 0489 VH

<400> SEQUENCE: 81

```
Glu Val Gln Leu Gln Gln Ser Gly Thr Glu Leu Val Arg Pro Gly Ala
1               5                   10                  15

Leu Val Arg Leu Ser Cys Lys Ala Ser Asp Phe Asn Ile Lys Asp Tyr
            20                  25                  30

Tyr Leu His Trp Val Lys Gln Arg Pro Glu Gln Gly Leu Glu Trp Val
        35                  40                  45

Gly Trp Ile Asp Pro Glu Thr Leu Asn Thr Ile Tyr Gly Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Gly Leu Thr Ser Glu Asp Ile Ala Val Tyr Tyr Cys
                85                  90                  95

Thr Ser Ser Thr Val Ile Ser Tyr Trp His Phe Asp Val Trp Gly Ala
            100                 105                 110

Gly Thr Ser Val Thr Val Ser Ser
        115                 120
```

<210> SEQ ID NO 82
<211> LENGTH: 108
<212> TYPE: PRT
<213> ORGANISM: Artificial Sequence
<220> FEATURE:
<223> OTHER INFORMATION: clone 0489 VL -continued

<400> SEQUENCE: 82

Asp Ile Val Met Thr Gln Ser His Lys Phe Met Ser Thr Ser Val Gly
1               5                   10                  15

Asp Arg Val Thr Phe Thr Cys Lys Ala Ser Gln Asp Val Arg Ser Ala
            20                  25                  30

Val Ala Trp Tyr Gln Gln Lys Ala Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ser Val Tyr Tyr Cys Gln Gln His Tyr Thr Thr Pro Leu
                85                  90                  95

Thr Phe Gly Ala Gly Thr Lys Leu Glu Leu Lys Arg
            100                 105

<210> SEQ ID NO 83
<211> LENGTH: 121
<212> TYPE: PRT
<213> ORGANISM: Artificial Sequence
<220> FEATURE:
<223> OTHER INFORMATION: clone 0490 VH

<400> SEQUENCE: 83

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Gly Thr Ile Tyr Tyr Ala Asp Thr Met
    50                  55                  60

Lys Gly Arg Phe Thr Ile Ser Arg Asp Asn Pro Lys Asn Thr Leu Phe
65                  70                  75                  80

Leu Gln Met Thr Thr Leu Arg Ser Glu Asp Thr Ala Met Tyr Tyr Cys
                85                  90                  95

Ala Arg Ser Tyr Tyr Ser Asp Phe Gly His Ala Met Asp Tyr Trp Gly
            100                 105                 110

Gln Gly Thr Ser Val Thr Val Ser Ser
        115                 120

<210> SEQ ID NO 84
<211> LENGTH: 113
<212> TYPE: PRT
<213> ORGANISM: Artificial Sequence
<220> FEATURE:
<223> OTHER INFORMATION: clone 0490 VL

<400> SEQUENCE: 84

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Ile Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ser
                 85                  90                  95

Thr His Phe Pro Leu Thr Phe Gly Ala Gly Thr Lys Leu Glu Leu Arg
                100                 105                 110

Arg
```

```
<210> SEQ ID NO 85
<211> LENGTH: 119
<212> TYPE: PRT
<213> ORGANISM: Artificial Sequence
<220> FEATURE:
<223> OTHER INFORMATION: clone 0491 VH

<400> SEQUENCE: 85

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Thr Phe
                 20                  25                  30

Gly Met His Trp Val Arg Gln Thr Pro Glu Arg Gly Leu Glu Trp Val
             35                  40                  45

Ala Tyr Ile Ser Ser Gly Ser Thr Asn Ile Tyr Tyr Ala Asp Pro Val
     50                  55                  60

Lys Gly Arg Phe Thr Ile Ser Arg Asp Asn Pro Lys Thr Leu Phe
 65                  70                  75                  80

Leu Gln Met Thr Gly Leu Arg Ser Glu Asp Thr Ala Met Tyr Tyr Cys
                 85                  90                  95

Ala Arg Asp Gly Phe Gly Asn Tyr Trp Phe Ala Tyr Trp Gly Gln Gly
                100                 105                 110

Thr Leu Val Thr Val Ser Ala
            115
```

```
<210> SEQ ID NO 86
<211> LENGTH: 108
<212> TYPE: PRT
<213> ORGANISM: Artificial Sequence
<220> FEATURE:
<223> OTHER INFORMATION: clone 0491 VL

<400> SEQUENCE: 86

Asp Ile Gln Met Thr Gln Ser Pro Ala Ser Leu Ser Ala Thr Val Gly
 1               5                  10                  15

Glu Thr Val Thr Ile Thr Cys Arg Thr Ser Gly Asn Ile His Asn Tyr
                 20                  25                  30

Leu Ala Trp Tyr Gln Gln Lys Gln Gly Lys Ser Pro Gln Leu Leu Val
             35                  40                  45

Tyr Asn Gly Gln Thr Leu Ala Glu Gly Val Pro Ser Lys Phe Ser Gly
     50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Phe Cys His Gln Tyr Phe Tyr Pro Leu
                 85                  90                  95

Thr Phe Gly Thr Gly Thr Lys Leu Glu Ile Lys Arg
                100                 105
```

```
<210> SEQ ID NO 87
<211> LENGTH: 121
```

```
<212> TYPE: PRT
<213> ORGANISM: Artificial Sequence
<220> FEATURE:
<223> OTHER INFORMATION: clone 0492 VH

<400> SEQUENCE: 87

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Ala Ser Leu Arg Ser Glu Asp Thr Ala Met Tyr Tyr Cys
                85                  90                  95

Ala Arg Ser Tyr Tyr Gly Asn Phe Gly Phe Ala Met Asp Tyr Trp Gly
            100                 105                 110

Gln Gly Thr Ser Val Thr Val Ser Ser
        115                 120

<210> SEQ ID NO 88
<211> LENGTH: 113
<212> TYPE: PRT
<213> ORGANISM: Artificial Sequence
<220> FEATURE:
<223> OTHER INFORMATION: clone 0492 VL

<400> SEQUENCE: 88

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Thr
            20                  25                  30

Gln Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Ser
                85                  90                  95

Thr His Phe Pro Leu Thr Phe Gly Ala Gly Thr Lys Leu Glu Leu Lys
            100                 105                 110

Arg

<210> SEQ ID NO 89
<211> LENGTH: 119
<212> TYPE: PRT
<213> ORGANISM: Artificial Sequence
<220> FEATURE:
<223> OTHER INFORMATION: clone 0493 VH

<400> SEQUENCE: 89

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30
```

Gly Met His Trp Val Arg Gln Thr Pro Glu Arg Gly Leu Glu Trp Val
                35                  40                  45

Ala Tyr Ile Ser Ser Asp Ser Ser Asn Ile Tyr Tyr Ala Asp Pro Val
         50                  55                  60

Lys Gly Arg Phe Thr Ile Ser Arg Asp Asn Pro Lys Lys Thr Leu Phe
 65                  70                  75                  80

Leu Gln Met Thr Gly Leu Arg Ser Glu Asp Thr Ala Ile Tyr Tyr Cys
                 85                  90                  95

Ala Arg Asp Gly Phe Gly Asn Tyr Trp Phe Ala Tyr Trp Gly Gln Gly
                100                 105                 110

Thr Leu Val Thr Val Ser Ala
            115

<210> SEQ ID NO 90
<211> LENGTH: 108
<212> TYPE: PRT
<213> ORGANISM: Artificial Sequence
<220> FEATURE:
<223> OTHER INFORMATION: clone 0493 VL

<400> SEQUENCE: 90

Asp Ile Gln Met Thr Gln Ser Pro Ala Ser Leu Ser Ala Thr Val Gly
  1               5                  10                  15

Glu Thr Val Thr Ile Thr Cys Arg Thr Ser Gly Asn Ile His Asn Tyr
             20                  25                  30

Leu Ala Trp Tyr Gln Gln Lys Gln Gly Lys Ser Pro Gln Leu Leu Val
         35                  40                  45

Tyr Asn Gly Gln Thr Leu Ala Glu Gly Val Pro Ser Lys Phe Ser Gly
     50                  55                  60

Ser Gly Ser Gly Thr Gln Tyr Ser Leu Lys Ile Asn Ser Leu Gln Pro
 65                  70                  75                  80

Glu Asp Phe Gly Ser Tyr Phe Cys His Gln Tyr Phe Tyr Phe Pro Leu
                 85                  90                  95

Thr Phe Gly Thr Gly Thr Lys Leu Glu Ile Lys Arg
                100                 105

<210> SEQ ID NO 91
<211> LENGTH: 119
<212> TYPE: PRT
<213> ORGANISM: Artificial Sequence
<220> FEATURE:
<223> OTHER INFORMATION: clone 0494 VH

<400> SEQUENCE: 91

Glu Val Gln Leu Gln Gln Ser Gly Ala Val Leu Val Lys Pro Gly Ala
  1               5                  10                  15

Ser Val Lys Leu Ser Cys Pro Ala Ser Gly Phe Asn Ile Lys Asp Thr
             20                  25                  30

Tyr Ile His Trp Val Ile Gln Arg Pro Glu Gln Gly Leu Glu Trp Ile
         35                  40                  45

Gly Arg Ile Asp Pro Ala Asn Gly Asp Thr Lys Cys Asp Pro Lys Phe
     50                  55                  60

Gln Val Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Phe Cys
                 85                  90                  95

Val Arg Asp Tyr Leu Tyr Pro Tyr Tyr Phe Asp Phe Trp Gly Gln Gly

Thr Thr Leu Thr Val Ser Ser
            115

<210> SEQ ID NO 92
<211> LENGTH: 108
<212> TYPE: PRT
<213> ORGANISM: Artificial Sequence
<220> FEATURE:
<223> OTHER INFORMATION: clone 0494 VL

<400> SEQUENCE: 92

Lys Ile Val Met Thr Gln Ser Pro Lys Ser Met Ser Met Ser Val Gly
1               5                   10                  15

Glu Arg Val Thr Leu Asn Cys Arg Ala Ser Glu Ser Val Asp Thr Tyr
            20                  25                  30

Val Ser Trp Tyr Gln Gln Lys Pro Glu Gln Ser Pro Glu Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Thr Tyr Asn Tyr Pro Leu
                85                  90                  95

Thr Phe Gly Ala Gly Thr Lys Leu Glu Leu Lys Arg
            100                 105

<210> SEQ ID NO 93
<211> LENGTH: 118
<212> TYPE: PRT
<213> ORGANISM: Artificial Sequence
<220> FEATURE:
<223> OTHER INFORMATION: clone 0495 VH

<400> SEQUENCE: 93

Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Ser Phe Pro Ser Tyr
            20                  25                  30

Val Val His Trp Val Lys Gln Lys Pro Gly Gln Gly Leu Glu Trp Ile
        35                  40                  45

Gly Tyr Ile Asn Pro Tyr Thr Asp Gly Thr Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Phe Tyr Tyr Tyr Ser Met Asp Tyr Trp Gly Gln Gly Thr
            100                 105                 110

Ser Val Thr Val Ser Ser
            115

<210> SEQ ID NO 94
<211> LENGTH: 107
<212> TYPE: PRT
<213> ORGANISM: Artificial Sequence
<220> FEATURE:
<223> OTHER INFORMATION: clone 0495 VL

<400> SEQUENCE: 94

```
Gln Ile Val Leu Thr Gln Ser Pro Ala Ile Met Ser Ala Ser Pro Gly
1               5                   10                  15

Glu Lys Val Thr Leu Thr Cys Ser Ala Asn Ser Ser Ile Arg Asn Met
            20                  25                  30

His Trp Tyr Gln Gln Lys Thr Gly Thr Ser Pro Lys Arg Trp Ile Tyr
        35                  40                  45

Asp Thr Ser Asn Leu Ala Ser Gly Val Pro Ser Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Phe Pro Tyr Thr
                85                  90                  95

Phe Gly Gly Gly Thr Lys Leu Glu Ile Lys Arg
            100                 105
```

<210> SEQ ID NO 95
<211> LENGTH: 124
<212> TYPE: PRT
<213> ORGANISM: Artificial Sequence
<220> FEATURE:
<223> OTHER INFORMATION: clone 0496 VH

<400> SEQUENCE: 95

```
Gln Val Gln Leu Ile Gln Ser Gly Ala Glu Leu Val Arg Pro Gly Ala
1               5                   10                  15

Ser Val Asn Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Asp Ile Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Pro Pro His Tyr Val Gly Asn Arg Tyr Tyr Ala Leu Asp
            100                 105                 110

Tyr Trp Gly Gln Gly Thr Ser Val Thr Val Ser Ser
        115                 120
```

<210> SEQ ID NO 96
<211> LENGTH: 108
<212> TYPE: PRT
<213> ORGANISM: Artificial Sequence
<220> FEATURE:
<223> OTHER INFORMATION: clone 0496 VL

<400> SEQUENCE: 96

```
Asp Ile Gln Met Thr Gln Ser Ser Ser Phe Ser Val Ser Leu Gly
1               5                   10                  15

Asp Arg Val Thr Val Thr Cys Lys Thr Thr Glu Asp Ile Tyr Asn Arg
            20                  25                  30

Leu Ala Trp Tyr Gln His Lys Pro Gly Asn Ala Pro Arg Leu Leu Ile
        35                  40                  45

Ser Gly Ala Thr Gly Leu Glu Thr Gly Val Pro Ser Arg Phe Ser Gly
    50                  55                  60

Ser Gly Ser Gly Lys Asp Tyr Thr Leu Thr Ile Thr Ser Leu Gln Thr
```

```
                65                  70                  75                  80
Glu Asp Val Ala Thr Tyr Tyr Cys Leu Gln Tyr Trp Ser Thr Pro Tyr
                    85                  90                  95

Thr Phe Gly Gly Gly Thr Lys Leu Glu Ile Lys Arg
                100                 105
```

<210> SEQ ID NO 97
<211> LENGTH: 123
<212> TYPE: PRT
<213> ORGANISM: Artificial Sequence
<220> FEATURE:
<223> OTHER INFORMATION: clone 0497 VH

<400> SEQUENCE: 97

```
Gln Val Gln Leu Gln Gln Pro Gly Ala Glu Phe Val Lys Pro Gly Ala
1               5                   10                  15

Ser Val Lys Met Ser Cys Lys Ala Ser Gly Tyr Thr Phe Thr Ser Tyr
                20                  25                  30

Trp Ile Thr Trp Val Lys Gln Arg Pro Gly Gln Gly Leu Glu Trp Ile
            35                  40                  45

Gly Asp Ile Tyr Pro Gly Ser Gly Ser Asn Lys Tyr Asn Glu Lys Phe
        50                  55                  60

Lys Ser Lys Ala Thr Leu Thr Val Asp Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Glu Arg Pro Thr Tyr Tyr Gly Ser Ser Ala Trp Phe Asp Tyr
                100                 105                 110

Trp Gly Gln Gly Thr Leu Val Thr Val Ser Ala
        115                 120
```

<210> SEQ ID NO 98
<211> LENGTH: 108
<212> TYPE: PRT
<213> ORGANISM: Artificial Sequence
<220> FEATURE:
<223> OTHER INFORMATION: clone 0497 VL

<400> SEQUENCE: 98

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Asn Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg
                100                 105
```

<210> SEQ ID NO 99
<211> LENGTH: 916
<212> TYPE: PRT
<213> ORGANISM: Artificial Sequence
<220> FEATURE:

<223> OTHER INFORMATION: huTfR-Fc(kih)-Avi

<400> SEQUENCE: 99

```
Met Gly Trp Ser Cys Ile Ile Leu Phe Leu Val Ala Thr Ala Thr Gly
1               5                   10                  15
Val His Ser Gly Leu Asn Asp Ile Phe Glu Ala Gln Lys Ile Glu Trp
            20                  25                  30
His Glu Asp Lys Thr His Thr Cys Pro Pro Cys Pro Ala Pro Glu Leu
        35                  40                  45
Leu Gly Gly Pro Ser Val Phe Leu Phe Pro Pro Lys Pro Lys Asp Thr
    50                  55                  60
Leu Met Ile Ser Arg Thr Pro Glu Val Thr Cys Val Val Val Asp Val
65                  70                  75                  80
Ser His Glu Asp Pro Glu Val Lys Phe Asn Trp Tyr Val Asp Gly Val
                85                  90                  95
Glu Val His Asn Ala Lys Thr Lys Pro Arg Glu Glu Gln Tyr Asn Ser
            100                 105                 110
Thr Tyr Arg Val Val Ser Val Leu Thr Val Leu His Gln Asp Trp Leu
        115                 120                 125
Asn Gly Lys Glu Tyr Lys Cys Lys Val Ser Asn Lys Ala Leu Pro Ala
    130                 135                 140
Pro Ile Glu Lys Thr Ile Ser Lys Ala Lys Gly Gln Pro Arg Glu Pro
145                 150                 155                 160
Gln Val Cys Thr Leu Pro Pro Ser Arg Asp Glu Leu Thr Lys Asn Gln
                165                 170                 175
Val Ser Leu Ser Cys Ala Val Lys Gly Phe Tyr Pro Ser Asp Ile Ala
            180                 185                 190
Val Glu Trp Glu Ser Asn Gly Gln Pro Glu Asn Asn Tyr Lys Thr Thr
        195                 200                 205
Pro Pro Val Leu Asp Ser Asp Gly Ser Phe Phe Leu Val Ser Lys Leu
    210                 215                 220
Thr Val Asp Lys Ser Arg Trp Gln Gln Gly Asn Val Phe Ser Cys Ser
225                 230                 235                 240
Val Met His Glu Ala Leu His Asn His Tyr Thr Gln Lys Ser Leu Ser
                245                 250                 255
Leu Ser Pro Gly Gly Gly Gly Ser Gly Gly Gly Ser Gly Ser
            260                 265                 270
Gly Gly Gly Gly Ser Leu Tyr Trp Asp Asp Leu Lys Arg Lys Leu Ser
        275                 280                 285
Glu Lys Leu Asp Ser Thr Asp Phe Thr Gly Thr Ile Lys Leu Leu Asn
    290                 295                 300
Glu Asn Ser Tyr Val Pro Arg Glu Ala Gly Ser Gln Lys Asp Glu Asn
305                 310                 315                 320
Leu Ala Leu Tyr Val Glu Asn Gln Phe Arg Glu Phe Lys Leu Ser Lys
                325                 330                 335
Val Trp Arg Asp Gln His Phe Val Lys Ile Gln Val Lys Asp Ser Ala
            340                 345                 350
Gln Asn Ser Val Ile Ile Val Asp Lys Asn Gly Arg Leu Val Tyr Leu
        355                 360                 365
Val Glu Asn Pro Gly Gly Tyr Val Ala Tyr Ser Lys Ala Ala Thr Val
    370                 375                 380
Thr Gly Lys Leu Val His Ala Asn Phe Gly Thr Lys Lys Asp Phe Glu
385                 390                 395                 400
```

-continued

Asp Leu Tyr Thr Pro Val Asn Gly Ser Ile Val Val Arg Ala Gly
            405                 410                 415

Lys Ile Thr Phe Ala Glu Lys Val Ala Asn Ala Glu Ser Leu Asn Ala
            420                 425                 430

Ile Gly Val Leu Ile Tyr Met Asp Gln Thr Lys Phe Pro Ile Val Asn
            435                 440                 445

Ala Glu Leu Ser Phe Phe Gly His Ala His Leu Gly Thr Gly Asp Pro
    450                 455                 460

Tyr Thr Pro Gly Phe Pro Ser Phe Asn His Thr Gln Phe Pro Pro Ser
465                 470                 475                 480

Arg Ser Ser Gly Leu Pro Asn Ile Pro Val Gln Thr Ile Ser Arg Ala
                485                 490                 495

Ala Ala Glu Lys Leu Phe Gly Asn Met Glu Gly Asp Cys Pro Ser Asp
            500                 505                 510

Trp Lys Thr Asp Ser Thr Cys Arg Met Val Thr Ser Glu Ser Lys Asn
            515                 520                 525

Val Lys Leu Thr Val Ser Asn Val Leu Lys Glu Ile Lys Ile Leu Asn
            530                 535                 540

Ile Phe Gly Val Ile Lys Gly Phe Val Glu Pro Asp His Tyr Val Val
545                 550                 555                 560

Val Gly Ala Gln Arg Asp Ala Trp Gly Pro Gly Ala Ala Lys Ser Gly
                565                 570                 575

Val Gly Thr Ala Leu Leu Leu Lys Leu Ala Gln Met Phe Ser Asp Met
            580                 585                 590

Val Leu Lys Asp Gly Phe Gln Pro Ser Arg Ser Ile Ile Phe Ala Ser
            595                 600                 605

Trp Ser Ala Gly Asp Phe Gly Ser Val Gly Ala Thr Glu Trp Leu Glu
    610                 615                 620

Gly Tyr Leu Ser Ser Leu His Leu Lys Ala Phe Thr Tyr Ile Asn Leu
625                 630                 635                 640

Asp Lys Ala Val Leu Gly Thr Ser Asn Phe Lys Val Ser Ala Ser Pro
                645                 650                 655

Leu Leu Tyr Thr Leu Ile Glu Lys Thr Met Gln Asn Val Lys His Pro
            660                 665                 670

Val Thr Gly Gln Phe Leu Tyr Gln Asp Ser Asn Trp Ala Ser Lys Val
            675                 680                 685

Glu Lys Leu Thr Leu Asp Asn Ala Ala Phe Pro Phe Leu Ala Tyr Ser
    690                 695                 700

Gly Ile Pro Ala Val Ser Phe Cys Phe Cys Glu Asp Thr Asp Tyr Pro
705                 710                 715                 720

Tyr Leu Gly Thr Thr Met Asp Thr Tyr Lys Glu Leu Ile Glu Arg Ile
                725                 730                 735

Pro Glu Leu Asn Lys Val Ala Arg Ala Ala Glu Val Ala Gly Gln
            740                 745                 750

Phe Val Ile Lys Leu Thr His Asp Val Glu Leu Asn Leu Asp Tyr Glu
            755                 760                 765

Arg Tyr Asn Ser Gln Leu Leu Ser Phe Val Arg Asp Leu Asn Gln Tyr
    770                 775                 780

Arg Ala Asp Ile Lys Glu Met Gly Leu Ser Leu Gln Trp Leu Tyr Ser
785                 790                 795                 800

Ala Arg Gly Asp Phe Phe Arg Ala Thr Ser Arg Leu Thr Thr Asp Phe
                805                 810                 815

Gly Asn Ala Glu Lys Thr Asp Arg Phe Val Met Lys Lys Leu Asn Asp

```
            820                 825                 830
Arg Val Met Arg Val Glu Tyr His Phe Leu Ser Pro Tyr Val Ser Pro
            835                 840                 845

Lys Glu Ser Pro Phe Arg His Val Phe Trp Gly Ser Gly Ser His Thr
850                 855                 860

Leu Pro Ala Leu Leu Glu Asn Leu Lys Leu Arg Lys Gln Asn Asn Gly
865                 870                 875                 880

Ala Phe Asn Glu Thr Leu Phe Arg Asn Gln Leu Ala Leu Ala Thr Trp
                885                 890                 895

Thr Ile Gln Gly Ala Ala Asn Ala Leu Ser Gly Asp Val Trp Asp Ile
                900                 905                 910

Asp Asn Glu Phe
            915

<210> SEQ ID NO 100
<211> LENGTH: 916
<212> TYPE: PRT
<213> ORGANISM: Artificial Sequence
<220> FEATURE:
<223> OTHER INFORMATION: cyTfR-Fc(kih)-Avi

<400> SEQUENCE: 100

Met Gly Trp Ser Cys Ile Ile Leu Phe Leu Val Ala Thr Ala Thr Gly
1               5                   10                  15

Val His Ser Gly Leu Asn Asp Ile Phe Glu Ala Gln Lys Ile Glu Trp
                20                  25                  30

His Glu Asp Lys Thr His Thr Cys Pro Pro Cys Pro Ala Pro Glu Leu
            35                  40                  45

Leu Gly Gly Pro Ser Val Phe Leu Phe Pro Pro Lys Pro Lys Asp Thr
        50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Cys Thr Leu Pro Pro Ser Arg Asp Glu Leu Thr Lys Asn Gln
                165                 170                 175

Val Ser Leu Ser Cys Ala Val Lys Gly Phe Tyr Pro Ser Asp Ile Ala
            180                 185                 190

Val Glu Trp Glu Ser Asn Gly Gln Pro Glu Asn Tyr Lys Thr Thr
        195                 200                 205

Pro Pro Val Leu Asp Ser Asp Gly Ser Phe Phe Leu Val Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Gly Gly Gly Ser Gly Gly Gly Gly Ser Gly Ser
```

```
            260                 265                 270
Gly Gly Gly Gly Ser Leu Tyr Trp Asp Asp Leu Lys Arg Lys Leu Ser
            275                 280                 285

Glu Lys Leu Asp Thr Thr Asp Phe Thr Ser Thr Ile Lys Leu Leu Asn
            290                 295                 300

Glu Asn Leu Tyr Val Pro Arg Glu Ala Gly Ser Gln Lys Asp Glu Asn
305                 310                 315                 320

Leu Ala Leu Tyr Ile Glu Asn Gln Phe Arg Glu Phe Lys Leu Ser Lys
            325                 330                 335

Val Trp Arg Asp Gln His Phe Val Lys Ile Gln Val Lys Asp Ser Ala
            340                 345                 350

Gln Asn Ser Val Ile Ile Val Asp Lys Asn Gly Gly Leu Val Tyr Leu
            355                 360                 365

Val Glu Asn Pro Gly Gly Tyr Val Ala Tyr Ser Lys Ala Ala Thr Val
            370                 375                 380

Thr Gly Lys Leu Val His Ala Asn Phe Gly Thr Lys Lys Asp Phe Glu
385                 390                 395                 400

Asp Leu Asp Ser Pro Val Asn Gly Ser Ile Val Ile Val Arg Ala Gly
            405                 410                 415

Lys Ile Thr Phe Ala Glu Lys Val Ala Asn Ala Glu Ser Leu Asn Ala
            420                 425                 430

Ile Gly Val Leu Ile Tyr Met Asp Gln Thr Lys Phe Pro Ile Val Lys
            435                 440                 445

Ala Asp Leu Ser Phe Phe Gly His Ala His Leu Gly Thr Gly Asp Pro
450                 455                 460

Tyr Thr Pro Gly Phe Pro Ser Phe Asn His Thr Gln Phe Pro Pro Ser
465                 470                 475                 480

Gln Ser Ser Gly Leu Pro Asn Ile Pro Val Gln Thr Ile Ser Arg Ala
            485                 490                 495

Ala Ala Glu Lys Leu Phe Gly Asn Met Glu Gly Asp Cys Pro Ser Asp
            500                 505                 510

Trp Lys Thr Asp Ser Thr Cys Lys Met Val Thr Ser Glu Asn Lys Ser
            515                 520                 525

Val Lys Leu Thr Val Thr Asn Val Leu Lys Glu Thr Lys Ile Leu Asn
            530                 535                 540

Ile Phe Gly Val Ile Lys Gly Phe Val Glu Pro Asp His Tyr Val Val
545                 550                 555                 560

Val Gly Ala Gln Arg Asp Ala Trp Gly Pro Gly Ala Ala Lys Ser Ser
            565                 570                 575

Val Gly Thr Ala Leu Leu Leu Lys Leu Ala Gln Met Phe Ser Asp Met
            580                 585                 590

Val Leu Lys Asp Gly Phe Gln Pro Ser Arg Ser Ile Ile Phe Ala Ser
            595                 600                 605

Trp Ser Ala Gly Asp Phe Gly Ser Val Gly Ala Thr Glu Trp Leu Glu
            610                 615                 620

Gly Tyr Leu Ser Ser Leu His Leu Lys Ala Phe Thr Tyr Ile Asn Leu
625                 630                 635                 640

Asp Lys Ala Val Leu Gly Thr Ser Asn Phe Lys Val Ser Ala Ser Pro
            645                 650                 655

Leu Leu Tyr Thr Leu Ile Glu Lys Thr Met Gln Asp Val Lys His Pro
            660                 665                 670

Val Thr Gly Arg Ser Leu Tyr Gln Asp Ser Asn Trp Ala Ser Lys Val
            675                 680                 685
```

```
Glu Lys Leu Thr Leu Asp Asn Ala Ala Phe Pro Phe Leu Ala Tyr Ser
    690             695                 700
Gly Ile Pro Ala Val Ser Phe Cys Phe Cys Glu Asp Thr Asp Tyr Pro
705             710                 715                 720
Tyr Leu Gly Thr Thr Met Asp Thr Tyr Lys Glu Leu Val Glu Arg Ile
                725                 730                 735
Pro Glu Leu Asn Lys Val Ala Arg Ala Ala Glu Val Ala Gly Gln
            740                 745                 750
Phe Val Ile Lys Leu Thr His Asp Thr Glu Leu Asn Leu Asp Tyr Glu
            755                 760                 765
Arg Tyr Asn Ser Gln Leu Leu Leu Phe Leu Arg Asp Leu Asn Gln Tyr
    770                 775                 780
Arg Ala Asp Val Lys Glu Met Gly Leu Ser Leu Gln Trp Leu Tyr Ser
785                 790                 795                 800
Ala Arg Gly Asp Phe Phe Arg Ala Thr Ser Arg Leu Thr Thr Asp Phe
                805                 810                 815
Arg Asn Ala Glu Lys Arg Asp Lys Phe Val Met Lys Lys Leu Asn Asp
            820                 825                 830
Arg Val Met Arg Val Glu Tyr Tyr Phe Leu Ser Pro Tyr Val Ser Pro
            835                 840                 845
Lys Glu Ser Pro Phe Arg His Val Phe Trp Gly Ser Gly Ser His Thr
850                 855                 860
Leu Ser Ala Leu Leu Glu Ser Leu Lys Leu Arg Arg Gln Asn Asn Ser
865                 870                 875                 880
Ala Phe Asn Glu Thr Leu Phe Arg Asn Gln Leu Ala Leu Ala Thr Trp
                885                 890                 895
Thr Ile Gln Gly Ala Ala Asn Ala Leu Ser Gly Asp Val Trp Asp Ile
            900                 905                 910
Asp Asn Glu Phe
        915

<210> SEQ ID NO 101
<211> LENGTH: 954
<212> TYPE: PRT
<213> ORGANISM: Artificial Sequence
<220> FEATURE:
<223> OTHER INFORMATION: huTfR-SNAP tag

<400> SEQUENCE: 101

Met Met Asp Gln Ala Arg Ser Ala Phe Ser Asn Leu Phe Gly Gly Glu
1               5                   10                  15
Pro Leu Ser Tyr Thr Arg Phe Ser Leu Ala Arg Gln Val Asp Gly Asp
            20                  25                  30
Asn Ser His Val Glu Met Lys Leu Ala Val Asp Glu Glu Asn Ala
            35                  40                  45
Asp Asn Asn Thr Lys Ala Asn Val Thr Lys Pro Lys Arg Cys Ser Gly
        50                  55                  60
Ser Ile Cys Tyr Gly Thr Ile Ala Val Ile Val Phe Phe Leu Ile Gly
65              70                  75                  80
Phe Met Ile Gly Tyr Leu Gly Tyr Cys Lys Gly Val Glu Pro Lys Thr
                85                  90                  95
Glu Cys Glu Arg Leu Ala Gly Thr Glu Ser Pro Val Arg Glu Glu Pro
            100                 105                 110
Gly Glu Asp Phe Pro Ala Ala Arg Arg Leu Tyr Trp Asp Asp Leu Lys
        115                 120                 125
```

-continued

```
Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540
```

```
Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe Thr Arg Tyr Pro Tyr Asp Val Pro
        755                 760                 765

Asp Tyr Ala Ser Gly Asp Lys Asp Cys Glu Met Lys Arg Thr Thr Leu
770                 775                 780

Asp Ser Pro Leu Gly Lys Leu Glu Leu Ser Gly Cys Glu Gln Gly Leu
785                 790                 795                 800

His Glu Ile Lys Leu Leu Gly Ser Gly Thr Ser Ala Ala Asp Ala Val
                805                 810                 815

Glu Val Pro Ala Pro Ala Ala Val Leu Gly Gly Pro Glu Pro Leu Met
            820                 825                 830

Gln Ala Thr Ala Trp Leu Asn Ala Tyr Phe His Gln Pro Glu Ala Ile
        835                 840                 845

Glu Glu Phe Pro Val Pro Ala Leu His His Pro Val Phe Gln Gln Glu
850                 855                 860

Ser Phe Thr Arg Gln Val Leu Trp Lys Leu Leu Lys Val Val Lys Phe
865                 870                 875                 880

Gly Glu Val Ile Ser Tyr Gln Gln Leu Ala Ala Leu Ala Gly Asn Pro
                885                 890                 895

Ala Ala Thr Ala Ala Val Lys Thr Ala Leu Ser Gly Asn Pro Val Pro
            900                 905                 910

Ile Leu Ile Pro Cys His Arg Val Val Ser Ser Ser Gly Ala Val Gly
        915                 920                 925

Gly Tyr Glu Gly Gly Leu Ala Val Lys Glu Trp Leu Leu Ala His Glu
930                 935                 940

Gly His Arg Leu Gly Lys Pro Gly Leu Gly
945                 950
```

<210> SEQ ID NO 102
<211> LENGTH: 954
<212> TYPE: PRT
<213> ORGANISM: Artificial Sequence
<220> FEATURE:
<223> OTHER INFORMATION: cyTfR-SNAP tag

<400> SEQUENCE: 102

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Gly Val Asp Glu Glu Asn Thr
        35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Pro
        100                 105                 110

Glu Glu Asp Phe Pro Ala Ala Pro Arg Leu Tyr Trp Asp Asp Leu Lys
    115                 120                 125

Arg Lys Leu Ser Glu Lys Leu Asp Thr Thr Asp Phe Thr Ser Thr Ile
130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Lys Ala Asp Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
        355                 360                 365

Glu Asn Lys Ser Val Lys Leu Thr Val Thr Asn Val Leu Lys Glu Thr
```

```
              370                 375                 380
Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
                405                 410                 415

Ala Lys Ser Ser Val Gly Thr Ala Leu Leu Lys Leu Ala Gln Met
                420                 425                 430

Phe Ser Asp Met Val Leu Lys Asp Gly Phe Gln Pro Ser Arg Ser Ile
                435                 440                 445

Ile Phe Ala Ser Trp Ser Ala Gly Asp Phe Gly Ser Val Gly Ala Thr
                450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
                500                 505                 510

Val Lys His Pro Val Thr Gly Arg Ser Leu Tyr Gln Asp Ser Asn Trp
                515                 520                 525

Ala Ser Lys Val Glu Lys Leu Thr Leu Asp Asn Ala Ala Phe Pro Phe
                530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Ala Arg Ala Ala Ala Glu
                580                 585                 590

Val Ala Gly Gln Phe Val Ile Lys Leu Thr His Asp Thr Glu Leu Asn
                595                 600                 605

Leu Asp Tyr Glu Arg Tyr Asn Ser Gln Leu Leu Leu Phe Leu Arg Asp
                610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
                660                 665                 670

Lys Leu Asn Asp Arg Val Met Arg Val Glu Tyr Tyr Phe Leu Ser Pro
                675                 680                 685

Tyr Val Ser Pro Lys Glu Ser Pro Phe Arg His Val Phe Trp Gly Ser
                690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
                740                 745                 750

Val Trp Asp Ile Asp Asn Glu Phe Thr Arg Tyr Pro Tyr Asp Val Pro
                755                 760                 765

Asp Tyr Ala Ser Gly Asp Lys Asp Cys Glu Met Lys Arg Thr Thr Leu
                770                 775                 780

Asp Ser Pro Leu Gly Lys Leu Glu Leu Ser Gly Cys Glu Gln Gly Leu
785                 790                 795                 800
```

```
His Glu Ile Lys Leu Leu Gly Ser Gly Thr Ser Ala Ala Asp Ala Val
                805                 810                 815
Glu Val Pro Ala Pro Ala Ala Val Leu Gly Gly Pro Glu Pro Leu Met
            820                 825                 830
Gln Ala Thr Ala Trp Leu Asn Ala Tyr Phe His Gln Pro Glu Ala Ile
        835                 840                 845
Glu Glu Phe Pro Val Pro Ala Leu His His Pro Val Phe Gln Gln Glu
    850                 855                 860
Ser Phe Thr Arg Gln Val Leu Trp Lys Leu Leu Lys Val Val Lys Phe
865                 870                 875                 880
Gly Glu Val Ile Ser Tyr Gln Gln Leu Ala Ala Leu Ala Gly Asn Pro
                885                 890                 895
Ala Ala Thr Ala Ala Val Lys Thr Ala Leu Ser Gly Asn Pro Val Pro
            900                 905                 910
Ile Leu Ile Pro Cys His Arg Val Val Ser Ser Ser Gly Ala Val Gly
        915                 920                 925
Gly Tyr Glu Gly Gly Leu Ala Val Lys Glu Trp Leu Leu Ala His Glu
    930                 935                 940
Gly His Arg Leu Gly Lys Pro Gly Leu Gly
945                 950
```

<210> SEQ ID NO 103
<211> LENGTH: 37
<212> TYPE: DNA
<213> ORGANISM: Artificial Sequence
<220> FEATURE:
<223> OTHER INFORMATION: rbHC.up

<400> SEQUENCE: 103
aagcttgcca ccatggagac tgggctgcgc tggcttc       37

<210> SEQ ID NO 104
<211> LENGTH: 21
<212> TYPE: DNA
<213> ORGANISM: Artificial Sequence
<220> FEATURE:
<223> OTHER INFORMATION: rbHCf.do

<400> SEQUENCE: 104
ccattggtga gggtgcccga g       21

<210> SEQ ID NO 105
<211> LENGTH: 34
<212> TYPE: DNA
<213> ORGANISM: Artificial Sequence
<220> FEATURE:
<223> OTHER INFORMATION: rbLC.up

<400> SEQUENCE: 105
aagcttgcca ccatggacay gagggccccc actc       34

<210> SEQ ID NO 106
<211> LENGTH: 26
<212> TYPE: DNA
<213> ORGANISM: Artificial Sequence
<220> FEATURE:
<223> OTHER INFORMATION: rbLC.do

<400> SEQUENCE: 106
cagagtrctg ctgaggttgt aggtac       26

<210> SEQ ID NO 107
<211> LENGTH: 20
<212> TYPE: DNA
<213> ORGANISM: Artificial Sequence
<220> FEATURE:
<223> OTHER INFORMATION: BcPCR_FHLC_leader.fw

<400> SEQUENCE: 107
atggacatga gggtccccgc                                           20

<210> SEQ ID NO 108
<211> LENGTH: 24
<212> TYPE: DNA
<213> ORGANISM: Artificial Sequence
<220> FEATURE:
<223> OTHER INFORMATION: BcPCR_huCkappa.rev

<400> SEQUENCE: 108
gatttcaact gctcatcaga tggc                                      24

<210> SEQ ID NO 109
<211> LENGTH: 6
<212> TYPE: PRT
<213> ORGANISM: Artificial Sequence
<220> FEATURE:
<223> OTHER INFORMATION: clone 299 HVR-H1

<400> SEQUENCE: 109

Phe Ser Leu Ser Ser Tyr
1               5

<210> SEQ ID NO 110
<211> LENGTH: 2
<212> TYPE: PRT
<213> ORGANISM: Artificial Sequence
<220> FEATURE:
<223> OTHER INFORMATION: clone 299 HVR-H2s

<400> SEQUENCE: 110

Trp Ser
1

<210> SEQ ID NO 111
<211> LENGTH: 15
<212> TYPE: PRT
<213> ORGANISM: Artificial Sequence
<220> FEATURE:
<223> OTHER INFORMATION: clone 299 HVR-H2

<400> SEQUENCE: 111

Tyr Ile Trp Trp Ser Gly Gly Ser Thr Asp Tyr Ala Ser Trp Ala
1               5                   10                  15

<210> SEQ ID NO 112
<211> LENGTH: 14
<212> TYPE: PRT
<213> ORGANISM: Artificial Sequence
<220> FEATURE:
<223> OTHER INFORMATION: clone 299 HVR-H3

<400> SEQUENCE: 112

Gly Thr Ser Tyr Pro Asp Tyr Gly Asp Ala Asn Gly Phe Asp
1               5                   10

<210> SEQ ID NO 113
<211> LENGTH: 7

```
<212> TYPE: PRT
<213> ORGANISM: Artificial Sequence
<220> FEATURE:
<223> OTHER INFORMATION: clone 299 HVR-L1

<400> SEQUENCE: 113

Ser Gln Ser Ile Ser Ser Tyr
1               5

<210> SEQ ID NO 114
<211> LENGTH: 3
<212> TYPE: PRT
<213> ORGANISM: Artificial Sequence
<220> FEATURE:
<223> OTHER INFORMATION: clone 299 HVR-L2

<400> SEQUENCE: 114

Arg Ala Ser
1

<210> SEQ ID NO 115
<211> LENGTH: 9
<212> TYPE: PRT
<213> ORGANISM: Artificial Sequence
<220> FEATURE:
<223> OTHER INFORMATION: clone 299 HVR-L3

<400> SEQUENCE: 115

Cys Tyr Ser Ser Ser Asn Val Asp Asn
1               5

<210> SEQ ID NO 116
<211> LENGTH: 7
<212> TYPE: PRT
<213> ORGANISM: Artificial Sequence
<220> FEATURE:
<223> OTHER INFORMATION: clone 494 HVR-H1

<400> SEQUENCE: 116

Gly Phe Asn Ile Lys Asp Thr
1               5

<210> SEQ ID NO 117
<211> LENGTH: 3
<212> TYPE: PRT
<213> ORGANISM: Artificial Sequence
<220> FEATURE:
<223> OTHER INFORMATION: clone 494 HVR-H2s

<400> SEQUENCE: 117

Ala Asn Gly
1

<210> SEQ ID NO 118
<211> LENGTH: 17
<212> TYPE: PRT
<213> ORGANISM: Artificial Sequence
<220> FEATURE:
<223> OTHER INFORMATION: clone 494 HVR-H2

<400> SEQUENCE: 118

Arg Ile Asp Pro Ala Asn Gly Asp Thr Lys Cys Asp Pro Lys Phe Gln
1               5                   10                  15

Val

<210> SEQ ID NO 119
```

```
<211> LENGTH: 8
<212> TYPE: PRT
<213> ORGANISM: Artificial Sequence
<220> FEATURE:
<223> OTHER INFORMATION: clone 494 HVR-H3

<400> SEQUENCE: 119

Tyr Leu Tyr Pro Tyr Tyr Phe Asp
1               5

<210> SEQ ID NO 120
<211> LENGTH: 7
<212> TYPE: PRT
<213> ORGANISM: Artificial Sequence
<220> FEATURE:
<223> OTHER INFORMATION: clone 494 HVR-L1

<400> SEQUENCE: 120

Ser Glu Ser Val Asp Thr Tyr
1               5

<210> SEQ ID NO 121
<211> LENGTH: 3
<212> TYPE: PRT
<213> ORGANISM: Artificial Sequence
<220> FEATURE:
<223> OTHER INFORMATION: clone 494 HVR-L2

<400> SEQUENCE: 121

Gly Ala Ser
1

<210> SEQ ID NO 122
<211> LENGTH: 6
<212> TYPE: PRT
<213> ORGANISM: Artificial Sequence
<220> FEATURE:
<223> OTHER INFORMATION: clone 494 HVR-L3

<400> SEQUENCE: 122

Thr Tyr Asn Tyr Pro Leu
1               5
```

MONOVALENT BLOOD BRAIN BARRIER SHUTTLE MODULES

CROSS REFERENCE TO RELATED APPLICATIONS

This application is a continuation of International Application No. PCT/EP2014/079353, having an international filing date of Dec. 29, 2014, the entire contents of which are incorporated herein by reference, and which claims benefit to International Application No. PCT/CN2014/070183, filed Jan. 6, 2014.

SEQUENCE LISTING

This application hereby incorporates by reference the material of the electronic Sequence Listing filed concurrently herewith. The material in the electronic Sequence Listing is submitted as a text (.txt) file entitled "P31922-US_Sequence_Listing_ST25" created on Jun. 5, 2016, which has a file size of 135 kilo bytes, and is herein incorporated by reference in its entirety.

FIELD OF THE INVENTION

The present invention relates to a blood brain barrier shuttle module that has one binding specificity that specifically binds to a blood brain barrier receptor (BBBR) and which is monovalent with respect to this binding specificity and methods of using this construct as blood barrier shuttle and in the treatment of neurological disorders.

BACKGROUND

Brain penetration of neurological disorder drugs such alls e.g. large biotherapeutic drugs or small molecule drugs having a low brain penetration, is strictly limited by the extensive and impermeable blood brain barrier (BBB) together with the other cell component in the neurovascular unit (NVU). Many strategies to overcome this obstacle have been tested and one is to utilize transcytosis pathways mediated by endogenous receptors expressed on the brain capillary endothelium (blood brain barrier receptor). Recombinant proteins such as monoclonal antibodies or peptides have been designed against these receptors to enable receptor-mediated delivery of biotherapeutics to the brain. However, strategies to maximize brain uptake while minimizing miss-sorting within the brain endothelial cells (BECs), and the extent of accumulation within certain organelles (especially organelles that lead to degradation of the biotherapeutic) in BECs, remain unexplored.

Monoclonal antibodies and other biotherapeutics have huge therapeutic potential for treatment of pathology in the central nervous system (CNS). However, their route into the brain is prevented by the BBB. Previous studies have illustrated that a very small percentage (approximately 0.1%) of an IgG injected in the bloodstream is able to penetrate into the CNS compartment (Felgenhauer, Klin. Wschr. 52 (1974) 1158-1164). This will certainly limit any pharmacological effect due to the low concentration within CNS of the antibody.

Therefore, there is a need for delivery systems of neurological disorder drugs across the BBB to shuttle the drugs into the brain efficiently.

In WO 2014/033074 a blood brain barrier shuttle is reported.

Mouse 8D3 anti-transferrin antibody and variable light chain domain (VL) variant (L596V and L598I) thereof is reported by Boado, R. J., et al. (Biotechnol. Bioeng. 102 (2009) 1251-1258).

SUMMARY

One aspect of the current invention is a blood brain barrier shuttle module comprising a brain effector entity, a linker and one monovalent binding entity which binds to a blood brain barrier receptor, wherein the linker couples the effector entity to the monovalent binding entity, which binds to the blood brain barrier receptor, wherein the monovalent binding entity does not comprise the variable domains of the anti-transferrin receptor antibody 8D3 (SEQ ID NO: 01 and SEQ ID NO: 02) or of the variant anti-transferrin receptor antibody 8D3v (SEQ ID NO: 01 and SEQ ID NO: 03).

The anti-transferrin receptor antibody 8D3 has a heavy chain variable domain with the following amino acid sequence:

```
                                        (SEQ ID NO: 01)
   EVQLVESGGG LVQPGNSLTL SCVASGFTFS NYGMHWIRQA

PKKGLEWIAM IYYDSSKMNY ADTVKGRFTI SRDNSKNTLY

LEMNSLRSED TAMYYCAVPT SHYVVDVWGQ GVSVTVSS.
```

The anti-transferrin receptor antibody 8D3 has a light chain variable domain with the following amino acid sequence:

```
                                        (SEQ ID NO: 02)
   DIQMTQSPAS LSASLEEIVT ITCQASQDIG NWLAWYQQKP

GKSPQLLIYG ATSLADGVPS RFSGSRSGTQ FSLKISRVQV

EDIGIYYCLQ AYNTPWTFGG GTKLELK.
```

The variant anti-transferrin receptor antibody 8D3v has the same heavy chain variable domain as antibody 8D3 and a light chain variable domain with mutants L104V and L106I that has the following amino acid sequence:

```
                                        (SEQ ID NO: 03)
   DIQMTQSPAS LSASLEEIVT ITCQASQDIG NWLAWYQQKP

GKSPQLLIYG ATSLADGVPS RFSGSRSGTQ FSLKISRVQV

EDIGIYYCLQ AYNTPWTFGG GTKVEIK.
```

In one embodiment of the blood brain barrier shuttle module the monovalent binding entity which binds to the blood brain barrier receptor is a polypeptide.

In one embodiment of the blood brain barrier shuttle module the monovalent binding entity which binds to the blood brain barrier receptor comprises a molecule selected from the group consisting of a blood brain barrier receptor ligand, a full length antibody, a scFv, an Fv, a scFab, and a VHH.

In one embodiment of the blood brain barrier shuttle module the blood brain receptor is selected from the group consisting of transferrin receptor, insulin receptor, insulin-like growth factor receptor, low density lipoprotein receptor-related protein 8, low density lipoprotein receptor-related protein 1 and heparin-binding epidermal growth factor-like growth factor. In one embodiment the blood brain receptor is the transferrin receptor.

In one embodiment the monovalent binding entity specifically binds to human transferrin receptor and to cynomolgus transferrin receptor.

In one embodiment of the blood brain barrier shuttle module the monovalent binding entity which binds to the blood brain barrier receptor comprises one scFab directed to the transferrin receptor, more particularly, a scFab that specifically binds to an epitope in the transferrin receptor comprised within the amino acid sequence of SEQ ID NOs: 04, 05, or 06.

In one embodiment of the blood brain barrier shuttle module the monovalent binding entity which binds to the blood brain barrier receptor comprises one scFv directed to the transferrin receptor, more particularly, a scFv recognizing an epitope in the transferrin receptor comprised within the amino acid sequence of SEQ ID NOs: 04, 05, or 06.

In one embodiment of the blood brain barrier shuttle module the brain effector entity is selected from the group consisting of neurological disorder drugs, neurotrophic factors, growth factors, enzymes, cytotoxic agents, antibodies directed to a brain target, monoclonal antibodies directed to a brain target, peptides directed to a brain target.

In one embodiment of the blood brain barrier shuttle module the brain target is selected from the group consisting of β-secretase 1, Aβ (Abeta), epidermal growth factor, epidermal growth factor receptor 2, tau, phosphorylated tau, phosphorylated tau(pS422), apolipoprotein E4, alpha synuclein, oligomeric fragments of alpha synuclein, CD20, huntingtin, prion protein, leucine rich repeat kinase 2, parkin, presenilin 2, gamma secretase, death receptor 6, amyloid precursor protein, p75 neurotrophin receptor and caspase 6.

In a particular embodiment of the blood brain barrier shuttle module the brain effector entity is a polypeptide.

In one embodiment of the blood brain barrier shuttle module the monovalent binding entity which binds to the blood brain receptor is a polypeptide and the monovalent binding entity is conjugated to the C-terminal end of the brain effector entity either directly or via a linker.

In one embodiment of the blood brain barrier shuttle module the brain effector entity comprises a full length antibody directed to a brain target. In one embodiment the full length antibody is an IgG.

In one preferred embodiment of the blood brain barrier shuttle module the blood brain barrier shuttle comprises a full length IgG antibody as brain effector entity, a linker and one scFab as the monovalent binding entity which binds the blood brain barrier receptor, wherein the scFab is conjugated to the C-terminal end of the Fc-region of one of the heavy chains of the IgG antibody via the linker.

In one embodiment of the blood brain barrier shuttle module the first heavy chain of the antibody of the blood brain barrier shuttle directed to a brain target comprises a first dimerization module and the second heavy chain of the antibody of the blood brain barrier shuttle to a brain target comprises a second dimerization module allowing heterodimerization of the two heavy chains.

In one embodiment of the blood brain barrier shuttle module the first dimerization module of the first heavy chain of the antibody of the blood brain barrier shuttle directed to the brain target comprises knobs and the dimerization module of the second heavy chain of the antibody of the blood brain barrier shuttle directed to the brain target comprises holes according to the knobs-into-holes strategy.

In one embodiment of the blood brain barrier shuttle module the linker is a peptidic linker. In one embodiment the peptidic linker has an amino acid sequence with a length of at least 25 amino acids. In one embodiment the peptidic linker has an amino acid sequence with a length of 30 to 50 amino acids. In one embodiment the peptidic linker is (G4S)6G2 (SEQ ID NO: 07) or (G4S)4 (SEQ ID NO: 08).

The following three embodiments are directed to a blood brain barrier shuttle module wherein the brain effector entity is a polypeptide with the proviso that the brain effector entity is not a full length antibody, in particular not a full length IgG.

In one embodiment of the blood brain barrier shuttle module the monovalent binding entity which binds to the blood brain barrier receptor comprises a CH2-CH3 Ig entity and one scFab (comprising a first linker), which binds to the blood brain barrier receptor, wherein the scFab is coupled to a C-terminal end of the CH2-CH3 Ig entity by a second linker.

In one embodiment of the blood brain barrier shuttle module the blood brain barrier shuttle comprises a brain effector entity, a linker, a CH2-CH3 Ig domain, a second linker and one scFab, which binds to the blood brain barrier receptor, wherein the brain effector entity is conjugated by a first linker to an N-terminal end of the CH2-CH3 Ig domain and the scFab is conjugated to a C-terminal end of the CH2-CH3 Ig domain by a second linker.

In one embodiment of the blood brain barrier shuttle module the CH2-CH3 Ig entity is a CH2-CH3 IgG entity.

Further aspects of the current invention are an (isolated) nucleic acid encoding the blood brain barrier shuttle module as reported herein, a host cell comprising the (isolated) nucleic acid encoding the blood brain barrier shuttle module, and a pharmaceutical formulation comprising the blood brain barrier shuttle module.

The blood brain barrier shuttle module as reported herein can be used as a medicament, in particular it can be used for the treatment of a neurological disorder such as e.g. Alzheimer's disease.

The blood brain barrier shuttle module as reported herein can be used to transport the brain effector entity across the blood brain barrier.

In a particular embodiment, the heavy chain of the IgG antibody of the blood brain barrier shuttle module as reported herein conjugated at its C-terminal end of the Fc-region to the scFab as monovalent binding entity, which binds to the blood brain barrier receptor, has the following structure:

IgG heavy chain,
linker conjugating the C-terminal end of the Fc-region of the IgG heavy chain to the N-terminal end of the VL domain of the scFab,
variable light chain domain (VL) and C-kappa light chain domain of the scFab,
linker conjugating the C-terminal end of the C-kappa light chain domain of the scFab to the N-terminal end of the VH domain of the scFab,
variable heavy chain domain (VH) of the scFab antibody and IgG CH1 heavy chain domain.

One aspect as reported herein is a fusion polypeptide to transport a brain effector entity across the blood brain barrier comprising a CH2-CH3 Ig entity, a linker and one scFab that specifically binds to a blood brain barrier receptor, wherein the scFab is conjugated to a C-terminal end of the CH2-CH3 Ig entity by the linker, wherein scFab does not comprise the variable domains of the anti-transferrin receptor antibody 8D3 (SEQ ID NO: 01 and SEQ ID NO: 02) or of the variant anti-transferrin receptor antibody 8D3v (SEQ ID NO: 01 and SEQ ID NO: 03).

One aspect as reported herein is a fusion polypeptide to transport a brain effector entity across the blood brain barrier comprising a CH2-CH3 Ig entity, a linker and one scFv that specifically binds to a blood brain barrier receptor, wherein the scFv is conjugated to a C-terminal end of the CH2-CH3 Ig entity by the linker, wherein scFv does not comprise the variable domains of the anti-transferrin receptor antibody 8D3 (SEQ ID NO: 01 and SEQ ID NO: 02) or of the variant anti-transferrin receptor antibody 8D3v (SEQ ID NO: 01 and SEQ ID NO: 03).

In one embodiment the fusion polypeptide further comprises a linker at the N-terminal end of the CH2-CH3 Ig entity to conjugate the brain effector entity to the N-terminal end of the CH2-CH3 Ig entity.

In one embodiment of the fusion polypeptide the brain effector entity is selected from the group consisting of neurological disorder drugs, neurotrophic factors, growth factors, enzymes, cytotoxic agents, antibody fragments or peptides directed to a brain target selected from the group consisting of scFv, Fv, scFab, Fab, VHH, F(ab')2.

In one embodiment of the fusion polypeptide the scFab or the scFv that specifically binds to the blood brain barrier receptor specifically binds to the transferrin receptor. In one embodiment the scFab or the scFv specifically binds to an epitope of the transferrin receptor comprised within the amino acid sequence of SEQ ID NO: 04, 05 or 06.

In embodiment of the fusion polypeptide the linker is a peptidic linker. In one embodiment the peptidic linker has an amino acid sequence with a length of at least 15 amino acids. In one embodiment the peptidic linker has a length of 20 to 50 amino acids. In one embodiment the peptidic linker has the amino acid sequence (G4S)6G2, (SEQ ID NO: 07) or (G4S)4 (SEQ ID NO: 08).

In one embodiment of the fusion polypeptide the CH2-CH3 Ig entity is a CH2-CH3 IgG entity.

Further aspects of the current invention are an isolated nucleic acid encoding the fusion polypeptide as reported herein and a host cell comprising the nucleic acid encoding the fusion polypeptide as reported herein.

One aspect as reported herein is a conjugate comprising a fusion polypeptide as reported herein and a brain effector entity conjugated to an N-terminal end of the CH2-CH3 Ig entity of the fusion polypeptide as reported herein via a linker.

In one embodiment of the conjugate the brain effector entity is a neurotrophic factor and the linker conjugating the neurotrophic factor to the N-terminal end of the CH2-CH3 Ig entity is a peptidic linker.

Further aspects as reported herein are a pharmaceutical formulation comprising the conjugate as reported herein and a pharmaceutical carrier, the use of the conjugate as reported herein, in particular the use of the conjugate for the treatment of a neurodegenerative disorder in particular Alzheimer's disease.

The monovalent binding entity that specifically binds to a blood brain barrier receptor can be conjugated to any terminus of the light or heavy chain of the antibody either directly or via a peptidic linker. In one embodiment the monovalent binding entity is conjugated to a C-terminus of the heavy chain.

The C-terminus of a heavy chain of an antibody can be a complete C-terminus ending with the amino acid residues PGK. The C-terminus of the heavy chain can be a shortened C-terminus in which one or two of the C-terminal amino acid residues have been removed. In one embodiment the C-terminus of the heavy chain is a shortened C-terminus ending with the amino acid residues PG.

The monovalent binding entity can be conjugated to the respective antibody chain either directly or via a peptidic linker. In one embodiment the peptidic linker has the amino acid sequence GGSGGGGSGGGGSGGGGS (SEQ ID NO: 09).

The monovalent binding entity can be an antibody scFv fragment. In one embodiment the monovalent binding entity is a scFv comprising in N- to C-terminal order a light chain variable domain-a light chain constant domain-a peptidic linker-a heavy chain variable domain-the heavy chain constant domain 1.

In one embodiment the monovalent binding entity is a scFv fragment of an anti-transferrin receptor-antibody with a (G4S)6 peptidic linker (SEQ ID NO: 10).

In one embodiment the blood-brain-barrier receptor is selected from the group consisting of transferrin receptor, insulin receptor, insulin-like growth factor receptor, low density lipoprotein receptor-related protein 8, low density lipoprotein receptor-related protein 1 and heparin-binding epidermal growth factor-like growth factor. In one embodiment blood-brain-barrier receptor is a human blood-brain-barrier receptor. In one embodiment the blood-brain-barrier receptor is the transferrin receptor and the antibody does not inhibit the binding of the transferrin receptor to transferrin. In one embodiment the blood-brain-barrier receptor is the human transferrin receptor.

In one embodiment the peptidic linker conjugating the monovalent binding entity to the brain effector entity is an amino acid sequence with a length of at least 15 amino acids. In one embodiment the peptidic linker has a length of 18 to 25 amino acids.

In one embodiment, the brain effector entity is a full length antibody. In one embodiment the brain effector entity is a full length antibody of the subclass IgG1 or IgG4.

In one embodiment the monovalent binding entity is an anti-blood brain barrier receptor antibody or a blood brain barrier receptor binding fragment thereof. In one embodiment, the anti-blood brain barrier receptor antibody or fragment thereof does not impair the binding of the blood brain barrier receptor to one or more of its native ligands. In another embodiment, the anti-blood brain barrier receptor antibody specifically binds to human transferrin receptor in such a manner that it does not inhibit binding of the human transferrin receptor to human transferrin.

In one embodiment the blood brain barrier shuttle module is effector silent.

In one embodiment the brain effector entity is a full length antibody comprising an Fc-region, wherein in case the Fc-region is of the human subclass IgG1 the Fc-region comprises the mutations L234A, L235A and P329G (numbering according to the EU index of Kabat), or in case the Fc-region is of the human subclass IgG4 the Fc-region comprises the mutations S228P, L235E and P329G (numbering according to the EU index of Kabat).

BRIEF DESCRIPTION OF DRAWING

FIG. 1 depicts the assay scheme for the assay used in the transcytosis screening.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include (a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);

(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The term "blood-brain barrier" (BBB) denotes the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal cord barrier within the spinal cord, and the blood-retinal barrier within the retina are contiguous capillary barriers within the CNS, and are herein collectively referred to as the blood-brain barrier or BBB. The BBB also encompasses the blood-CSF barrier (choroid plexus) where the barrier is comprised of ependymal cells rather than capillary endothelial cells.

The term "central nervous system" (CNS) denotes the complex of nerve tissues that control bodily function, and includes the brain and spinal cord.

The term "blood-brain barrier receptor" (BBBR) denotes an extracellular membrane-linked receptor protein expressed on brain endothelial cells which is capable of transporting molecules across the BBB or be used to transport exogenous administrated molecules. Examples of BBBR include but are not limited to transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). An exemplary BBBR is the transferrin receptor (TfR).

The term "brain effector entity" denotes a molecule that is to be transported to the brain across the BBB. The effector entity typically has a characteristic therapeutic activity that is desired to be delivered to the brain. Effector entities include neurological disorder drugs and cytotoxic agents such as e.g. polypeptides and antibodies, in particular monoclonal antibodies or fragments thereof directed to a brain target.

The term "monovalent binding entity" denotes a molecule able to bind specifically and in a monovalent binding mode to a BBBR. The blood brain shuttle module and/or conjugate as reported herein are characterized by the presence of a single unit of a monovalent binding entity i.e. the blood brain shuttle module and/or conjugate of the present invention comprise exactly one unit of the monovalent binding entity. The monovalent binding entity includes but is not limited to polypeptides, full length antibodies, antibody fragments including Fab, Fab', Fv fragments, single-chain antibody molecules such as e.g. single chain Fab, scFv. The monovalent binding entity can be, for example, a scaffold protein engineered using state of the art technologies like phage display or immunization. The monovalent binding entity can also be a polypeptide. In certain embodiments, the monovalent binding entity comprises a CH2-CH3 Ig domain and a single chain Fab (scFab) directed to a blood brain barrier receptor. The scFab is coupled to the C-terminal end of the CH2-CH3 Ig domain by a linker. In certain embodiments, the scFab is directed to the transferrin receptor.

The term "monovalent binding mode" denotes a specific binding to the BBBR where the interaction between the monovalent binding entity and the BBBR takes place through one single epitope. The monovalent binding mode prevents any dimerization/multimerization of the BBBR due to a single epitope interaction point. The monovalent binding mode prevents that the intracellular sorting of the BBBR is altered.

The term "epitope" denotes any polypeptide determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "transferrin receptor" (TfR) is a transmembrane glycoprotein (with a molecular weight of about 180,000 Da which is composed of two disulfide-bonded sub-units (each of apparent molecular weight of about 90,000 Da) and is involved in iron uptake in vertebrates. In one embodiment, the TfR herein is human TfR comprising the amino acid sequence as reported in Schneider et al. (Nature 311 (1984) 675-678).

The term "neurological disorder" denotes a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS and/or brain, including brain metastases resulting from cancer elsewhere in the body).

The term "neurological disorder drug" denotes a drug or therapeutic agent that treats one or more neurological disorder(s). Neurological disorder drugs include, but are not limited to, small molecule compounds, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs are described herein and include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and the corresponding disorders they may be used to treat: Brain-derived neurotrophic factor (BDNF), Chronic brain injury (Neurogenesis), Fibroblast growth factor 2 (FGF-2), Anti-Epidermal Growth Factor Receptor Brain cancer, (EGFR)-antibody, glial cell-line derived neural factor Parkinson's disease, (GDNF), Brain-derived neurotrophic factor (BDNF) Amyotrophic lateral sclerosis, depression, Lysosomal enzyme Lysosomal storage disorders of the brain, Ciliary neurotrophic factor (CNTF) Amyotrophic lateral sclerosis, Neuregulin-1 Schizophrenia, Anti-HER2 antibody (e.g. trastuzumab) Brain metastasis from HER2-positive cancer.

The term "imaging agent" denotes a compound that has one or more properties that permit its presence and/or location to be detected directly or indirectly. Examples of such imaging agents include proteins and small molecule compounds incorporating a labeled entity that permits detection.

The terms "CNS antigen" and "brain target" denote an antigen and/or molecule expressed in the CNS, including the brain, which can be targeted with an antibody or small molecule. Examples of such antigen and/or molecule include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

The term "that specifically binds" denotes an antibody selectively or preferentially binding to an antigen. The binding affinity is generally determined using a standard assay, such as Scatchard analysis, or surface plasmon resonance technique (e.g. using BIACORE®).

The term "CH2-CH3 Ig entity" as used herein refers to a protein entity derived from immunoglobulin CH2 or CH3 domains. The "CH2-CH3 Ig entity" comprises two "CH2-CH3" polypeptides forming a dimer. The immunoglobulin can be IgG, IgA, IgD, IgE or IgM. In one embodiment, the CH2-CH3 Ig entity derived from an IgG immunoglobulin and is referred to herein as "CH2-CH3 IgG entity". The term includes native sequence of CH2-CH3 domains and variant CH2-CH3 domains. In one embodiment, the "CH2-CH3 Ig entity" derives from human heavy chain CH2-CH3 IgG domain which extends from Cys226, or from Pro230, to the carboxyl-terminus of the heavy chain. However, the C-terminal lysine (Lys447) of the Fc region may or may not be present. Unless otherwise specified herein, numbering of amino acid residues in the CH2-CH3 domain region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "conjugate" is fusion protein of the present invention conjugated to one or more heterologous molecule(s), including but not limited to a label, neurological disorder drug or cytotoxic agent.

The term "linker" denotes a chemical linker or a single chain peptidic linker that covalently connects different entities of the blood brain barrier shuttle module and/or the fusion polypeptide and/or the conjugate as reported herein. The linker connects for example the brain effector entity to the monovalent binding entity. For example, if the monovalent binding entity comprises a CH2-CH3 Ig entity and a scFab directed to the blood brain barrier receptor, then the linker conjugates the scFab to the C-terminal end of the CH3-CH2 Ig entity. The linker conjugating the brain effector entity to the monovalent binding entity (first linker) and the linker connecting the scFab to the C-terminal end of the CH2-CH3 Ig domain (second linker) can be the same or different.

Single chain peptidic linkers, comprising of from one to twenty amino acid residues joined by peptide bonds, can be used. In certain embodiments, the amino acids are selected from the twenty naturally-occurring amino acids. In certain other embodiments, one or more of the amino acids are selected from glycine, alanine, proline, asparagine, glutamine and lysine. In other embodiments, the linker is a chemical linker. In certain embodiments, the linker is a single chain peptidic linker with an amino acid sequence with a length of at least 25 amino acid residues, in one preferred embodiment with a length of 32 to 50 amino acid residues. In one embodiment the peptidic linker is a (GxS)n linker with G=glycine, S=serine, (x=3, n=8, 9 or 10) or (x=4 and n=6, 7 or 8), in one embodiment with x=4, n=6 or 7, in one preferred embodiment with x=4, n=7. In one embodiment the linker is (G4S)4 (SEQ ID NO: 08). In one embodiment the linker is (G4S)6G2 (SEQ ID NO: 07).

Conjugation may be performed using a variety of chemical linkers. For example, the monovalent binding entity or the fusion polypeptide and the brain effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

Covalent conjugation can either be direct or via a linker. In certain embodiments, direct conjugation is by construction of a polypeptide fusion (i.e. by genetic fusion of the two genes encoding the monovalent binding entity towards the BBBR and effector entity and expressed as a single polypeptide (chain)). In certain embodiments, direct conjugation is by formation of a covalent bond between a reactive group on one of the two portions of the monovalent binding entity against the BBBR and a corresponding group or acceptor on the brain effector entity. In certain embodiments, direct conjugation is by modification (i.e. genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e. an amino acid) with a desired reactive group (i.e. a cysteine residue) may be introduced into, e.g., the monovalent binding entity towards the BBBR antibody and a disulfide bond formed with the neurological drug. Methods for covalent conjugation of nucleic acids to proteins are also known in the art (i.e., photocrosslinking, see, e.g., Zatsepin et al. Russ. Chem. Rev. 74 (2005) 77-95). Conjugation may also be performed using a variety of linkers. For example, a monovalent binding entity and a effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptidic linkers, comprised of from one to twenty amino acid residues joined by peptide bonds, may also be used. In certain such embodiments, the amino acid residues are selected from the twenty naturally-occurring amino acids. In certain other such embodiments, one or more of the amino acid residues are selected from glycine, alanine, proline, asparagine, glutamine and lysine. The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52 (1992) 127-131; U.S. Pat. No. 5,208,020) may be used.

II. Compositions and Methods

In one aspect, the invention is based, in part, on the finding that the blood brain barrier shuttle modules as reported herein can be used to deliver a brain effector entity across the blood brain barrier into the brain. In certain embodiments, the blood brain barrier shuttle module comprises a monovalent binding entity that specifically binds to a blood brain barrier receptor, such as the transferrin receptor. The blood brain barrier shuttle modules as reported herein are useful, e.g., for the diagnosis or treatment of neurological disorders, such as Alzheimer's disease, Parkinson's Disease and Alzheimer's Disease with Parkinson's Disease co-morbidity.

A. Exemplary Anti-Blood Brain Barrier Receptor Antibodies

Monovalent binding entities that specifically bind to a blood brain barrier receptor can be characterized with respect to their binding and transcytosis properties:
 - efficient cell binding of BBBR expressing cells as monovalent binding entity,
 - efficient in vitro transcytosis as monovalent binding entity,
 - human-cynomolgus cross-reactivity (e.g. in BIAcore and FACS experiments).

The transcytosis screening was performed in an hCMEC/D3 based assay. The assay was performed in a pulse-chase mode. The hCMEC/D3 brain endothelial cells were incubated with the monovalent binding entity for 1 hour, washed thereafter and the following parameters were determined 0 hours and 4 hours post washing:
 i) amount of monovalent binding entity taken up into the cells during the loading phase,
 ii) basolateral amount of monovalent binding entity 4 hours post loading and washing;
 iii) apical amount of monovalent binding entity 4 hours post loading and washing;
 iv) amount of monovalent binding entity in the cells (by cell lysis) 0 hours and 4 hours after loading and washing;
 v) total amount of monovalent binding entity 0 hours and 4 hours after loading and washing.

In order to be eligible as monovalent binding entity in a blood brain barrier shuttle module as reported herein the monovalent binding entity has to be i) taken up by the hCMEC/D3 cells (endocytosis), ii) transported outside the hCMEC/D3 cells (exocytosis), and iii) stable inside the hCMEC/D3 cells (no or low transport to the endosome for degradation).

Thus, in one embodiment the monovalent binding entity is characterized in a hCMEC/D3 based assay by i) an (substantial) uptake into the hCMEC/D3 cells during a one-hour loading period, ii) a release into the apical and/or basolateral compartment after the loading period and a washing step within 4 hours after the washing, and iii) a low (intracellular) degradation rate.

In one embodiment the loading is at a concentration of about 2.67 µg/mL monovalent binding entity for one hour.

It has been found that a monovalent binding entity in order to be eligible as monovalent binding entity of a blood brain barrier shuttle module as reported herein has to show in the above described hCMEC/D3 based assay the following threshold values:
  i) an amount of monovalent binding entity taken up into the cells during the loading phase of 400 pg or more,
  ii) basolateral amount of monovalent binding entity 4 hours post loading and washing of 100 pg or more, and
  iii) apical amount of monovalent binding entity 4 hours post loading and washing of 150 pg or more.

The mouse anti-human transferrin-receptor antibody 128.1 (for variable region sequences see WO 93/10819 and SEQ ID NO: 11 and 12) can be taken as reference. In this case the monovalent binding entity in order to be eligible as monovalent binding entity of a blood brain barrier shuttle module as reported herein has to show in the above described hCMEC/D3 based assay the following threshold values:
  i) an amount of monovalent binding entity taken up into the cells during the loading phase of 20% or more of the loading of antibody 128.1,
  ii) basolateral amount of monovalent binding entity 4 hours post loading and washing of 15% or more of the basolateral amount of antibody 128.1; and
  iii) apical amount of monovalent binding entity 4 hours post loading and washing of 15% or more of the apical amount of antibody 128.1.

The hCMEC/D3 based assay was performed as follows (this is one embodiment of all aspects as reported herein):

Medium and supplements for hCMEC/D3 (see WO 2006/056879 and Weksler, B. B., et al., FASEB J. 19 (2005) 1872-1874) can be obtained from Lonza. hCMEC/D3 cells (passages 26-29) are/can be cultured to confluence on collagen-coated coverslips (microscopy) or flasks in EBM2 medium containing 2.5% FBS, a quarter of the supplied growth factors and fully complemented with supplied hydrocortisone, gentamycin and ascorbic acid.

For all transcytosis assays, high density pore ($1\times10^8$ pores/cm$^2$) PET membrane filter inserts (0.4 µm pore size, 12 mm diameter) are/can be used in 12-well cell culture plates. Media volumes are calculated to be 400 µL and 1600 µL for apical and basolateral chambers, respectively. Apical chambers of filter inserts are/can be coated with rat tail collagen I (7.5 µg/cm$^2$) followed by fibronectin (5 µg/mL), each incubation lasting for 1 h at RT. hCMEC/D3 cells are/can be grown to confluent monolayers (~$2\times10^5$ cells/cm$^2$) for 10-12 days in EBM2 medium. Empty filters are/can be blocked in PBS containing 1% BSA for 1 hour or overnight (o/n) before assay and then calibrated for at least 1 hour in EBM2 before the assay.

The assay (for assay scheme see FIG. 1) was performed in serum-free EBM2 medium which was otherwise reconstituted as described herein. On day of the assay, cells are serum-starved for 60 min. to deplete the natural ligand of the blood brain barrier receptor in question. Filter inserts with or without (but blocked overnight in complete medium) cells were incubated apically with monoclonal antibodies in question (monovalent binding entity) for 1 hour at 37° C. The monolayers were washed at room temperature (RT) in serum-free medium apically (400 µL) and basolaterally (1600 µL) three times for 3-5 min. each. Pre-warmed medium was added to the apical chamber and the filters transferred to a fresh 12 well plate (blocked overnight with PBS containing 1% BSA) containing 1600 µL pre-warmed medium. At this point, filters with or without cells were lysed in 500 µL RIPA buffer in order to determine specific antibody (monovalent binding entity) uptake. The remaining filters were incubated at 37° C. or at 4° C. and samples were collected at various time points to determine apical and/or basolateral release of the antibody (monovalent binding entity). The content of antibody in the samples can be quantified using a highly sensitive IgG ELISA (see Example 10). For each time point, data should be generated from two empty filters and three filter cell cultures.

The results for 69 anti-transferrin receptor antibodies are shown in the Table below. Antibody 128.1 was used as reference.

| values of reference antibody 128.1 for set | transcytosis loading 0 h [pg] | total basolateral 4 h [pg] | total apical 4 h [pg] |
|---|---|---|---|
| 1 | 2072 | 896 | 1547 |
| 2 | 2951 | 797 | 1690 |
| 3 | 3448 | 1034 | 1843 |
| 4 | 864 | 274 | 375 |
| 5 | 3027 | 957 | 1679 |
| 6 | 2133 | 638 | 1187 |
| 7 | 3490 | 1138 | 1966 |

| clone | transcytosis loading 0 h [pg] | total basolateral 4 h [pg] | total apical 4 h [pg] | set | relative loading to reference [%] | relative basolateral of reference [%] | relative apical of reference [%] |
|---|---|---|---|---|---|---|---|
| No. 0116 | 872 | 70 | 203 | 1 | 42 | 8 | 13 |
| No. 0127 | 293 | 56 | 160 | 1 | 10 | 7 | 9 |
| No. 0128 | 1155 | 231 | 746 | 3 | 33 | 22 | 40 |
| No. 0134 | 151 | 18 | 154 | 3 | 4 | 2 | 8 |

-continued

| | | | | | | | |
|---|---|---|---|---|---|---|---|
| No. 0143 | 651 | 156 | 475 | 2 | 22 | 20 | 28 |
| No. 0146 | 1623 | 357 | 748 | 2 | 55 | 45 | 44 |
| No. 0150 | 298 | 36 | 205 | 3 | 9 | 3 | 11 |
| No. 0279 | 768 | 77 | 131 | 4 | 89 | 28 | 35 |
| No. 0280 | 221 | 42 | 133 | 4 | 26 | 15 | 35 |
| No. 0281 | 34 | 3 | 16 | 4 | 4 | 1 | 4 |
| No. 0282 | 574 | 14 | 45 | 4 | 66 | 5 | 12 |
| No. 0283 | 112 | 24 | 52 | 4 | 13 | 9 | 14 |
| No. 0284 | 32 | 0 | 24 | 4 | 4 | 0 | 6 |
| No. 0285 | 21 | 0 | 18 | 4 | 2 | 0 | 5 |
| No. 0286 | 130 | 29 | 93 | 4 | 15 | 11 | 25 |
| No. 0291 | 419 | 61 | 96 | 4 | 48 | 22 | 26 |
| No. 0292 | 118 | 27 | 95 | 4 | 14 | 10 | 25 |
| No. 0293 | 354 | 28 | 88 | 4 | 41 | 10 | 23 |
| No. 0294 | 25 | 0 | 12 | 4 | 3 | 0 | 3 |
| No. 0295 | 101 | 21 | 75 | 4 | 12 | 8 | 20 |
| No. 0297 | 95 | 17 | 64 | 4 | 11 | 6 | 17 |
| No. 0298 | 195 | 10 | 59 | 4 | 23 | 4 | 16 |
| No. 0299 | 705 | 170 | 294 | 4 | 82 | 64 | 79 |
| No. 0300 | 632 | 103 | 86 | 4 | 73 | 38 | 23 |
| No. 0301 | 61 | 10 | 41 | 4 | 7 | 4 | 11 |
| No. 0302 | 420 | 118 | 217 | 4 | 49 | 43 | 58 |
| No. 0304 | 665 | 157 | 282 | 4 | 77 | 58 | 75 |
| No. 0305 | 154 | 33 | 111 | 4 | 18 | 12 | 30 |
| No. 0313 | 175 | 36 | 132 | 5 | 6 | 4 | 8 |
| No. 0316 | 84 | 0 | 72 | 5 | 3 | 0 | 4 |
| No. 0318 | 130 | 21 | 82 | 5 | 4 | 2 | 5 |
| No. 0319 | 406 | 104 | 343 | 5 | 13 | 11 | 20 |
| No. 0322 | 172 | 84 | 96 | 5 | 6 | 9 | 6 |
| No. 0323 | 794 | 175 | 478 | 5 | 26 | 18 | 28 |
| No. 0324 | 193 | 32 | 144 | 5 | 6 | 3 | 9 |
| No. 0325 | 664 | 166 | 483 | 5 | 22 | 17 | 29 |
| No. 0329 | 744 | 192 | 449 | 6 | 35 | 30 | 38 |
| No. 0335 | 601 | 0 | 45 | 6 | 28 | 0 | 4 |
| No. 0339 | 967 | 227 | 580 | 6 | 45 | 36 | 49 |
| No. 0343 | 883 | 195 | 574 | 6 | 41 | 34 | 48 |
| No. 0346 | 1684 | 424 | 832 | 6 | 79 | 67 | 70 |
| No. 0348 | 838 | 205 | 626 | 6 | 39 | 32 | 53 |
| No. 0349 | 1538 | 181 | 396 | 6 | 72 | 28 | 33 |
| No. 0350 | 940 | 257 | 637 | 6 | 44 | 40 | 54 |
| No. 0411 | 1655 | 512 | 955 | 6 | 78 | 80 | 80 |
| No. 0431 | 1738 | 511 | 493 | 6 | 81 | 80 | 42 |
| No. 0432 | 890 | 265 | 421 | 6 | 42 | 41 | 35 |
| No. 0433 | 957 | 274 | 370 | 6 | 45 | 43 | 31 |
| No. 0434 | 1033 | 264 | 403 | 6 | 48 | 41 | 34 |
| No. 0435 | 1356 | 351 | 503 | 6 | 64 | 55 | 42 |
| No. 0441 | 1256 | 158 | 383 | 6 | 59 | 25 | 32 |
| No. 0445 | 758 | 133 | 196 | 6 | 36 | 21 | 17 |
| No. 0447 | 451 | 133 | 320 | 6 | 21 | 21 | 18 |
| No. 0449 | 728 | 214 | 377 | 6 | 34 | 34 | 32 |
| No. 0451 | 797 | 174 | 442 | 6 | 37 | 27 | 37 |
| No. 0452 | 822 | 291 | 490 | 6 | 39 | 46 | 41 |
| No. 0453 | 720 | 220 | 500 | 6 | 34 | 34 | 42 |
| No. 0486 | 1434 | 454 | 503 | 7 | 41 | 40 | 26 |
| No. 0487 | 4583 | 685 | 1364 | 7 | 131 | 60 | 69 |
| No. 0488 | 991 | 176 | 658 | 7 | 28 | 15 | 33 |
| No. 0489 | 2124 | 370 | 1179 | 7 | 61 | 33 | 60 |
| No. 0490 | 4011 | 581 | 1388 | 7 | 115 | 51 | 71 |
| No. 0491 | 1310 | 244 | 762 | 7 | 38 | 21 | 39 |
| No. 0492 | 2962 | 516 | 1052 | 7 | 85 | 45 | 54 |
| No. 0493 | 1006 | 215 | 885 | 7 | 29 | 19 | 45 |
| No. 0494 | 3510 | 748 | 1503 | 7 | 101 | 66 | 76 |
| No. 0495 | 1236 | 184 | 617 | 7 | 35 | 16 | 31 |
| No. 0496 | 2178 | 539 | 1402 | 7 | 64 | 47 | 71 |
| No. 0497 | 2984 | 725 | 1809 | 7 | 85 | 64 | 92 |

Antibody 299 shows a transcytosis loading of 705 pg, whereof after 4 hours 170 pg (=24% of loading) can be found in the basolateral compartment and 294 pg (=42% of loading) can be found in the apical compartment.

Antibody 494 shows a transcytosis loading of 3510 pg, whereof after 4 hours 748 pg (=21% of loading) can be found in the basolateral compartment and 1503 pg (=43% of loading) can be found in the apical compartment.

The antibodies fulfilling the criteria as outlined above are embodiments of the current invention.

Thus, one aspect as reported herein is an anti-transferrin receptor antibody or transferrin receptor binding fragment thereof comprising (1) a heavy chain variable domain that has the amino acid sequence of SEQ ID NO: 13 and a light chain variable domain that has the amino acid sequence of SEQ ID NO: 14, or (2) a heavy chain variable domain that has the amino acid sequence of SEQ ID NO: 15 and a light chain variable domain that has the amino acid sequence of SEQ ID NO: 16, or (3) a heavy chain variable domain that has the amino acid sequence of SEQ ID NO: 17 and a light chain variable domain that has the amino acid sequence of SEQ ID NO: 18, or (4) a heavy chain variable domain that has the amino acid sequence of SEQ ID NO: 19 and a light chain variable domain that has the amino acid sequence of SEQ ID NO: 20, or (5) a heavy chain variable domain that has the amino acid sequence of SEQ ID NO: 21 and a light chain variable domain that has the amino acid sequence of SEQ ID NO: 22, or (6) a heavy chain variable domain that has the amino acid sequence of SEQ ID NO: 23 and a light chain variable domain that has the amino acid sequence of SEQ ID NO: 24, or (7) a heavy chain variable domain that has the amino acid sequence of SEQ ID NO: 25 and a light chain variable domain that has the amino acid sequence of SEQ ID NO: 26, or (8) a heavy chain variable domain that has the amino acid sequence of SEQ ID NO: 27 and a light chain variable domain that has the amino acid sequence of SEQ ID NO: 28, or (9) a heavy chain variable domain that has the amino acid sequence of SEQ ID NO: 29 and a light chain variable domain that has the amino acid sequence of SEQ ID NO: 30, or

(10) a heavy chain variable domain that has the amino acid sequence of SEQ ID NO: 31 and a light chain variable domain that has the amino acid sequence of SEQ ID NO: 32, or

(11) a heavy chain variable domain that has the amino acid sequence of SEQ ID NO: 33 and a light chain variable domain that has the amino acid sequence of SEQ ID NO: 34, or

(12) a heavy chain variable domain that has the amino acid sequence of SEQ ID NO: 35 and a light chain variable domain that has the amino acid sequence of SEQ ID NO: 36, or

(13) a heavy chain variable domain that has the amino acid sequence of SEQ ID NO: 37 and a light chain variable domain that has the amino acid sequence of SEQ ID NO: 38, or

(14) a heavy chain variable domain that has the amino acid sequence of SEQ ID NO: 39 and a light chain variable domain that has the amino acid sequence of SEQ ID NO: 40, or

(15) a heavy chain variable domain that has the amino acid sequence of SEQ ID NO: 41 and a light chain variable domain that has the amino acid sequence of SEQ ID NO: 42, or

(16) a heavy chain variable domain that has the amino acid sequence of SEQ ID NO: 43 and a light chain variable domain that has the amino acid sequence of SEQ ID NO: 44, or

(17) a heavy chain variable domain that has the amino acid sequence of SEQ ID NO: 45 and a light chain variable domain that has the amino acid sequence of SEQ ID NO: 46, or

(18) a heavy chain variable domain that has the amino acid sequence of SEQ ID NO: 47 and a light chain variable domain that has the amino acid sequence of SEQ ID NO: 48, or

(19) a heavy chain variable domain that has the amino acid sequence of SEQ ID NO: 49 and a light chain variable domain that has the amino acid sequence of SEQ ID NO: 50, or

(20) a heavy chain variable domain that has the amino acid sequence of SEQ ID NO: 51 and a light chain variable domain that has the amino acid sequence of SEQ ID NO: 52, or

(21) a heavy chain variable domain that has the amino acid sequence of SEQ ID NO: 53 and a light chain variable domain that has the amino acid sequence of SEQ ID NO: 54, or

(22) a heavy chain variable domain that has the amino acid sequence of SEQ ID NO: 55 and a light chain variable domain that has the amino acid sequence of SEQ ID NO: 56, or

(23) a heavy chain variable domain that has the amino acid sequence of SEQ ID NO: 57 and a light chain variable domain that has the amino acid sequence of SEQ ID NO: 58, or

(24) a heavy chain variable domain that has the amino acid sequence of SEQ ID NO: 59 and a light chain variable domain that has the amino acid sequence of SEQ ID NO: 60, or

(25) a heavy chain variable domain that has the amino acid sequence of SEQ ID NO: 61 and a light chain variable domain that has the amino acid sequence of SEQ ID NO: 62, or

(26) a heavy chain variable domain that has the amino acid sequence of SEQ ID NO: 63 and a light chain variable domain that has the amino acid sequence of SEQ ID NO: 64, or

(27) a heavy chain variable domain that has the amino acid sequence of SEQ ID NO: 65 and a light chain variable domain that has the amino acid sequence of SEQ ID NO: 66, or

(28) a heavy chain variable domain that has the amino acid sequence of SEQ ID NO: 67 and a light chain variable domain that has the amino acid sequence of SEQ ID NO: 68, or

(29) a heavy chain variable domain that has the amino acid sequence of SEQ ID NO: 69 and a light chain variable domain that has the amino acid sequence of SEQ ID NO: 70, or

(30) a heavy chain variable domain that has the amino acid sequence of SEQ ID NO: 71 and a light chain variable domain that has the amino acid sequence of SEQ ID NO: 72, or

(31) a heavy chain variable domain that has the amino acid sequence of SEQ ID NO: 73 and a light chain variable domain that has the amino acid sequence of SEQ ID NO: 74, or

(32) a heavy chain variable domain that has the amino acid sequence of SEQ ID NO: 75 and a light chain variable domain that has the amino acid sequence of SEQ ID NO: 76, or

(33) a heavy chain variable domain that has the amino acid sequence of SEQ ID NO: 77 and a light chain variable domain that has the amino acid sequence of SEQ ID NO: 78, or

(34) a heavy chain variable domain that has the amino acid sequence of SEQ ID NO: 79 and a light chain variable domain that has the amino acid sequence of SEQ ID NO: 80, or

(35) a heavy chain variable domain that has the amino acid sequence of SEQ ID NO: 81 and a light chain variable domain that has the amino acid sequence of SEQ ID NO: 82, or

(36) a heavy chain variable domain that has the amino acid sequence of SEQ ID NO: 83 and a light chain variable domain that has the amino acid sequence of SEQ ID NO: 84, or

(37) a heavy chain variable domain that has the amino acid sequence of SEQ ID NO: 85 and a light chain variable domain that has the amino acid sequence of SEQ ID NO: 86, or

(38) a heavy chain variable domain that has the amino acid sequence of SEQ ID NO: 87 and a light chain variable domain that has the amino acid sequence of SEQ ID NO: 88, or

(39) a humanized heavy chain variable domain derived from the heavy chain variable domain that has the amino acid sequence of SEQ ID NO: 89 and a light chain variable domain that has the amino acid sequence of SEQ ID NO: 90, or

(40) a heavy chain variable domain that has the amino acid sequence of SEQ ID NO: 91 and a light chain variable domain that has the amino acid sequence of SEQ ID NO: 92,

(41) a heavy chain variable domain that has the amino acid sequence of SEQ ID NO: 93 and a light chain variable domain that has the amino acid sequence of SEQ ID NO: 94, or

(42) a heavy chain variable domain that has the amino acid sequence of SEQ ID NO: 95 and a light chain variable domain that has the amino acid sequence of SEQ ID NO: 96, or

(43) a heavy chain variable domain that has the amino acid sequence of SEQ ID NO: 97 and a light chain variable domain that has the amino acid sequence of SEQ ID NO: 98.

One preferred aspect as reported herein is an anti-transferrin receptor antibody or transferrin receptor binding fragment thereof comprising a heavy chain variable domain that has the amino acid sequence of SEQ ID NO: 23 and a light chain variable domain that has the amino acid sequence of SEQ ID NO: 24.

One preferred aspect as reported herein is an anti-transferrin receptor antibody or transferrin receptor binding fragment thereof comprising a heavy chain variable domain that has the amino acid sequence of SEQ ID NO: 91 and a light chain variable domain that has the amino acid sequence of SEQ ID NO: 92.

The respective amino acid sequences are depicted in the following Table.

| clone | heavy chain variable domain amino acid sequence (SEQ ID NO:) | light chain variable domain amino acid sequence (SEQ ID NO:) |
|---|---|---|
| No. 0128 | QSVEESGGRLVTPGTPLTLTCTVSGIDLSSYYMSWVR QAPGKGLEWIGIIYPSGYAYYTSWAKGRFTISKTSTT VDLKMTSLTTEDTATYFCARDVGDGGGTFDIWGQGTM VTVSS (13) | DIQMTQSPSSLSASVGDRVTITCRASQSISNYLNW YQQKPGKAPKLLIYDASSLESGVPSRFSGSGSGTD FTLTISSLQPEDFATYYCQQSGSTPYTFGQGTKLE IKR (14) |
| No. 0143 | GVQCQSLEESGGRLVTPGGSLTLTCTVSGIDLSTYSM GWVRQSPGKGLEYIGIISSSDNTYYTSWAKGRFTISK TSTTVDLKITSPTTEDTATYFCARGYNGGWKTPMDVW GQRTTVTVSS (15) | DIQMTQSPSSLSVSVGDRVTITCRASQGISNYLAW YQQKPGKAPELLIYAASILQGGVPSRFSGSGSGTD FTLTISSLQPEDVATYYCQQYNTYPPTFGQGTKLE IKR (16) |
| No. 0146 | GVQCEVQLVESGGGLVQPGGSLRLSCAASGFTFGDFA MNWVRQAPGKGLEWVSGISASGVSTYYADSVKGRVTI SRDNSKNTLNLQMNSLRAEDTAVYYCARDPCDASNDY GYCKLDVWGQGTTVTVSS (17) | DIQMTQSPSSLSASVGDRVTITCRASQSISSYLNW YQQKPGKAPKLLIYSASSLQSGVPSRFSGSRSGTE FTLTISSLQPEDFATYYCQQSYNTPLTFGGGTKVE IKR (18) |
| No. 0279 | QSVEESGGRLVTPGTPLTLTCTVSGIDLSSYAMGWVR QAPGKGLEWIGYIWSGGSADYASWAKGRFTISKTSTT VDLKIPSPTMEDTATYFCARGDAEYGDANGFAIWGPG TLVTVSL (19) | AYDMTQTPASVEVAVGGTVTIKCQASQSISNYLAW YQQKPGQPPKLLIYRASTLASGVSSRFKGSGSGTD FTLTISGVGCADAATYYCQQTLSTINIDNTFGGGT EVVVKR (20) |
| No. 0291 | QSVEESGGRLVTPGTPLTLTCTVSGFSLSSGAMTWVR QAPGKGLEWIGYIWSGGSTDYASWAKGRFTISKTSTT VDLKITSPTTEDTATYFCARGYGADYPDFGDANGFDP WGPGTLVTVSS (21) | AYDMTQTPASVEVAVGGTVTIKCQASQSISSYLAW YQQKPGQPPKLLIYRASTLASGVSSRFKGSGSGTQ FTLTISDLECADAATYYCQQGLSTINVDNTFGGGT EVVVKR (22) |
| No. 0299 | QSMEESGGRLVTPGTPLTLTCTVSGFSLSSYAMSWVR QAPGKGLEWIGYIWSGGSTDYASWAKGRFTISKTSTT VDLKITSPTTEDTATYFCARRYGTSYPDYGDANGFDP WGPGTLVTVSS (23) | AYDMTQTPASVEVAVGGTVTIKCQASQSISSYLSW YQQKPGQRPKLLIYRASTLASGVSSRFKGSGSGTQ FTLTISGVECADAATYYCQCYSSSNVDNTFGGGT EVVVKR (24) |
| No. 0300 | QSVEESGGRLVTPGTPLTLTCTASEFSLSNYYMSWVR QAPGKGLEYIGFIHTDGSTNYASWVNGRFTISRTSTT VDLKTTSLTTEDTATYFCCRYLVSGGTIAFDLWGPGT LVTVSS (25) | ADVVMTQTPASVEAAVGGTVTIKCQASQSISSYFA WYQQKPGQPPKLLIYRASKLATGVPSRFKGSGSGT EFTLTISDLECADAATYYCQTCGSISTYGGAFGGG TEVVVKR (26) |
| No. 0302 | QSLEESGGRLVTPGGSLTLTCTVSGFSLSTYAMTWVR QAPGKGLEWIGIIYAGTDITWYASWAKGRFTISKTST TVDLSITSPTTEDTATYFCAKVPYTGVSDYLYYFDLW GPGTLVTVSS (27) | AFEMTQTPSSVSEPVGGTVTIKCQASENIYSFLAW YQQKPGQPPKLLIYDASDLASGVPSRFKGSGSGTQ FTLTISDLECADAATYYCQQGYSGNVILNAFGGGT EVVVKR (28) |
| No. 0304 | QSMEESGGRLVTPGTPLTLTCTVSGFSLSSYAMSWVR QAPGKGLEWIGYIWSGGSTDYASWAKGRFTISKTSTT VDLKITSPTTEDTATYFCARRYGTSYPDYGDANGFDP WGPGTLVTVSS (29) | AYDMTQTPASVEVAVGGTVTIKCQASQSISSYLSW YQQKPGQRPKLLIYRASTLASGVSSRFKGSGSGTQ FTLTISGVECADAATYYCQCYSSSNVDNTFGGGT EVVVKR (30) |

-continued

| clone | heavy chain variable domain amino acid sequence (SEQ ID NO:) | light chain variable domain amino acid sequence (SEQ ID NO:) |
|---|---|---|
| No. 0323 | QSVEESGGRLVTPGTPLPLTCTVSGFSLSNYAMGWFR QAPGKGLEWIGYIWSGGSTDYASWAKGRFTISKTSTT VDLKMTSLTTEDTATYFCARADTVYRDDYGWSLWGPG TLVTVSS (31) | AYDMTQTPASVEVAVGGTVTIKCQASQSISIYLAW YQQKPGQPPKLLIYKASTLASGVPSRFKGSGSGTE FTLTISDLECADAATYYCQQAYSYSNVDNVFGGGT EVVVKR (32) |
| No. 0325 | QSVEESGGRLVTPGTPLTLTCTVSGFSLSNYNMGWVR QAPGKGLEWIGIISDAGSAWYASWVKGRFTISKTSTT VDLKITSPTTEDAATYFCARGDAAAYTTGTEFFSLWG PGTLVTVSS (33) | AYDMTQTPASVEVAVGGTVTIKCQASEDIESYLAW YQQKPGQRPKLLIYAVSTLASGVSSRFKGSGSGTE YTLTISGVQCADAATYYCQQGYSSSNLDNAFGGGT EVVVRR (34) |
| No. 0329 | GVQCQSLEESGGGLVKPGGTLTLTCTVSGFSLNSYSM TWVRQAPGKGLEWIGYIWSGGSADYANWAKGRFTISK TSTTVDLKMTSLTAEDTATYFCGRGYDTTDNGFNLWG PGTLVTVSS (35) | AYDMTQTPASVEAAVGGTVTIKCQASQSITSYLAW YQQKPGQPPKLLIYRASTLASGVSSRFKGSGSGTQ FTLTISGVECADAATYYCQQTYRYMNVDNVFGGGT EVVVKR (36) |
| No. 0339 | GVQCQSVEESGGRLVTPGTPLTLTCTVSGIDLSSHAM TWVRQAPGKGLEWIGYIWSGGSADYASWAKGRFTISK TSSTTVDLKIPSPTTEDTATYFCARGADEYGDANGFN IWGPGTLVTVSL (37) | AYDMTQTPSSVEAAVGGTVTIKCQASQSISNYLAW YQQKPGQPPELLIYRASTLASGVSSRFRGSGSGTD FTLTISGVGCADAATYYCQQGLSSSYVDNTFGGGT EVVVKR (38) |
| No. 0343 | GVQCQEQLKESGGGLVTPGTPLTLTCTASGFSLSIYY MSWVRQAPGKGLDWIGFIYVDSSSAHYASWAKGRFTI SKTSTTVDLKITSPTTEDTATYFCARDVDSSYFWGFN LWGPGTLVTVSS (39) | ADVVMTQTPSPVSGAVGGTVTIKCQASQSIDSYLS WYQQKPGQPPKLLIYSASTLASGVSSRFKGSGSGT QFTLTISDLECADAATYYCQCTYYDSSSIGGFGGG TEVVVKR (40) |
| No. 0346 | GVQCQSVEESGGRLVTPGTPLTLTCTVSGFSLSSNAI NWVRQAPGKGLEWIGYIYTDGNTYYASWAKGRFTISK TSTTVDLKITSPTTEDTATYFCARGVGYSDLWGPGTL VTVSS (41) | DVVMTQTPSSVSEPVGGTVTINCQASENIYSSLDW YQQKPGQPPKLLIYSASNLASGVSSRFKGSRSGTE YTLTISDLECADAATYYCQCIDGGNRGKPFGGGTE VVVKR (42) |
| No. 0348 | GVQCQSVEESGGRLVTPGTPLTLTCTASGFSLNSVYM SWVRQAPGKGLEWIGIIYASGSIYYASWAKGRFTISR TSSTTVDLKMTSLTTEDTATYFCVRSADYDSGMPFDL WGPGTLVTVSS (43) | AQVLTQTASSVSAAVGGTVTISCQSSQSVWNNNFL SWYQQKPGQPPKLLIYLASTLASGVPSRFKGSGSG TQFTLTISDLECDDAATYYCAGVYSDNIFAFGGGT EVVVKR (44) |
| No. 0349 | GVQCQSVEESGGRLVTPGTPLTLTCTVSGFSLSSSYM AWVRQAPGKGLEYIGFIHTDGSTYYATWVNGRFTISR TSTTVTLKMTSLTTEDTATYFCARYLVGSGAVAFDL WGPGTLVTVSS (45) | ADVVMTQTPASVEAAVGGTVTIKCQASQSISSYFA WYQQKPGQPPKLLIYRASNLATGVPSRFKGSGSGT EFTLTISDLECADAATYYCQSCGSISTYGGAFGGG TEVVVKR (46) |
| No. 0350 | GVQCQSVEESGGRLVTPGTPLTLTCTVSGFSLSSYAM GWVRQAPGKGLEWIGYIWSGGSTDYATWAKGRFTISK TSTTVDLSITSPTTEDTAAYFCVRSAGSGDAMGFNLW GPGTLVTVSS (47) | AYDMTQTPASVSEPVGGTVTIKCQASQSISSYLSW YQQKPGQPPKLLIYRASTLESGVPSRFKGSGSGTE FTLTISDLECADAATYYCQQGLSVIHVDNTFGGGT EVVVKR (48) |
| No. 0411 | QSVEESGGRLVTPGTPLTLTCTVSGFSLSNYAMTWVR QAPGKGLEWIGYIWSGGSTDYATWAKGRFTISKTSTT VDLKITSPTTEDTATYFCARGYGAGYPDYGDANGFDP WGPGTLVTVSS (49) | AYDMTQTPASVSAAVGGTVSINCQASQSISGYLSW YQQKPGQRPKLLIYRASTLASGVSSRFKGSGSGTQ FTLTISGVECADAATYYCQQGYSIINVDNTFGGGT EVVVKR (50) |
| No. 0431 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREESSYISGFDYWG QGTLVTVSS (51) | SSELTQDPAVSVALGQTVRITCQGDSLRSYYASWY QQKPGQAPVLVIYGKNNRPSGIPDRFSGSSSGNTA SLTITGAQAEDEADYYCNSRDDYGDGVFGGGTKLT VL (52) |
| No. 0432 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREESWWLSGLDYWG QGTLVTVSS (53) | SSELTQDPAVSVALGQTVRITCQGDSLRSYYASWY QQKPGQAPVLVIYGKNNRPSGIPDRFSGSSSGNTA SLTITGAQAEDEADYYCNSMTESMNYVFGGGTKLT VL (54) |
| No. 0433 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREESTWFSGFDYWG QGTLVTVSS (55) | SSELTQDPAVSVALGQTVRITCQGDSLRSYYASWY QQKPGQAPVLVIYGKNNRPSGIPDRFSGSSSGNTA SLTITGAQAEDEADYYCNSIDSSGNHDVFGGGTKL TVL (56) |
| No. 0434 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREYPWYIWSYDYWG QGTLVTVSS (57) | SSELTQDPAVSVALGQTVRITCQGDSLRSYYASWY QQKPGQAPVLVIYGKNNRPSGIPDRFSGSSSGNTA SLTITGAQAEDEADYYCNSPDSIAYGVVFGGGTKL TVL (58) |
| No. 0435 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARESYFLSGFDYWGQ GTIVTVSS (59) | SSELTQDPAVSVALGQTVRITCQGDSLRSYYASWY QQKPGQAPVLVIYGKNNRPSGIPDRFSGSSSGNTA SLTITGAQAEDEADYYCNSEDSESNLVFGGGTKLT VL (60) |

| clone | heavy chain variable domain amino acid sequence (SEQ ID NO:) | light chain variable domain amino acid sequence (SEQ ID NO:) |
|---|---|---|
| No. 0441 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARSWFGEWMDYWGQG TLVTVSS (61) | SSELTQDPAVSVALGQTVRITCQGDSLRSYYASWY QQKPGQAPVLVIYGKNNRPSGIPDRFSGSSSGNTA SLTITGAQAEDEADYYCNSIDSALDHVFGGGTKLT VL (62) |
| No. 0445 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARDSWYGWAFDYWGQ GTLVTVSS (63) | SSELTQDPAVSVALGQTVRITCQGDSLRSYYASWY QQKPGQAPVLVIYGKNNRPSGIPDRFSGSSSGNTA SLTITGAQAEDEADYYCNSRDMSLNVVFGGGTKLT VL (64) |
| No. 0447 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARESFYGWAFDYWGQ GTLVTVSS (65) | SSELTQDPAVSVALGQTVRITCQGDSLRSYYASWY QQKPGQAPVLVIYGKNNRPSGIPDRFSGSSSGNTA SLTITGAQAEDEADYYCNSRDSTLIVVVFGGGTKL TVL (66) |
| No. 0449 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARETWGWVAFDYWGQ GTLVTVSS (67) | SSELTQDPAVSVALGQTVRITCQGDSLRSYYASWY QQKPGQAPVLVIYGKNNRPSGIPDRFSGSSSGNTA SLTITGAQAEDEADYYCNSPDSSVNYMVFGGGTKL TVL (68) |
| No. 0451 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREEYYYLSGFDYWG QGTLVTVSS (69) | SSELTQDPAVSVALGQTVRITCQGDSLRSYYASWY QQKPGQAPVLVIYGKNNRPSGIPDRFSGSSSGNTA SITITGAQAEDEADYYCNSRDIIGDAVFGGGTKLT VL (70) |
| No. 0452 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCAREAWDYLSSMDYWG QGTLVTVSS (71) | SSELTQDPAVSVALGQTVRITCQGDSLRSYYASWY QQKPGQAPVLVIYGKNNRPSGIPDRFSGSSSGNTA SLTITGAQAEDEADYYCNSIDSEGNDIVFGGGTKL TVL (72) |
| No. 0453 | QVQLVQSGAEVKKPGASVKVSCKASGYTFTSYYMHWV RQAPGQGLEWMGIINPSGGSTSYAQKFQGRVTMTRDT STSTVYMELSSLRSEDTAVYYCARDVYGHLDYWGQGT LVTVSS (73) | SSELTQDPAVSVALGQTVRITCQGDSLRSYYASWY QQKPGQAPVLVIYGKNNRPSGIPDRFSGSSSGNTA SLTITGAQAEDEADYYCNSIDLSMDIVFGGGTKLT VL (74) |
| No. 0486 | DVLMTQTPLSLPVSLGDQASISCRSTQSFTGYNMNWV KQSNGERLEWIGSIDPFYGGTTYNQKFKDKATLTVDK PSSTAYMQLTSLTAEDSAVYYCAREGGNYYGPWFAYW GQGTLVTVSA (75) | EVQLQQSGPELEKPGASVKISCKASGYSVVHSDGI THLEWYLQKPGQSPKLLIYKVFNRFYGVPDRFSGS GSGTDFTLKISRVEAEDLGVYYCFQGSHVPWTFGG GTKLEIKR (76) |
| No. 0487 | DVQLVESGGGLVQPGGSRKLSCAASGFTFSSFGMHWV RQAPEKGLEWVAYISSGSGTIYYADTVKGRFTISRDN PKNTLFLQMTTLRSEDTAMYYCARSYYSDFGHAMDYW GQGTSVTVSS (77) | DVVMTQTPLTLSVTIGQPASISCKSSQSLLYTIGK TYLNWLLQRPGQSPKRLIYLVSKLDSGVPDRFSGS GSGTDFTLKISRVEAEDLGVYYCFQSTHFPLTFGA GTKLELRR (78) |
| No. 0488 | DVQLVESGGGLVQPGGSRKLSCAASGFTFSTFGMHWV RQTPERGLEWVAYISSGGTNIYYADPVKGRFTISRDN PKKTLFLQMTGLRSEDTAIYYCARDGFGNYWFAYWGQ GTLVTVSA (79) | DIQMTQSPASLSATVGETVTITCRTSGNIHNYLAW YQQKQGKSPQLLVYNGQTLAEGVPSKFSGSGSGTQ YSLKINSLQPEDFGSYFCHQYFYFPLTFGTGTKLE IKR (80) |
| No. 0489 | EVQLQQSGTELVRPGALVRLSCKASDFNIKDYYLHWV KQRPEQGLEWVGWIDPETLNTIYGPKFQGKASITADT SSNTAYLQLSGLTSEDIAVYYCTSSTVISYWHFDVWG AGTSVTVSS (81) | DIVMTQSHKFMSTSVGDRVTFTCKASQDVRSAVAW YQQKAGQSPKLLIYSASYRYTGVPDRFTGSGSGTD FTFTISSVQAEDLSVYYCQQHYTTPLTFGAGTKLE LKR (82) |
| No. 0490 | DVQLVESGGGLVQPGGSRKLSCAASGFTFSSFGMHWV RQAPEKGLEWVAYISSGSGTIYYADTMKGRFTISRDN PKNTLFLQMTTLRSEDTAMYYCARSYYSDFGHAMDYW GQGTSVTVSS (83) | DVVMTQTPLTLSVTIGQPASISCKSSQSLLYTIGK TYLNWLLQRPGQSPKRLIYLVSKLDSGVPDRFSGS GSGTDFTLKISRVEAEDLGVYYCFQSTHFPLTFGA GTKLELRR (84) |
| No. 0491 | DVQLVESGGGLVQPGGSRKLSCAASGFTFSTFGMHWV RQTPERGLEWVAYISSGSTNIYYADPVKGRFTISRDN PKKTLFLQMTGLRSEDTAMYYCARDGFGNYWFAYWGQ GTLVTVSA (85) | DIQMTQSPASLSATVGETVTITCRTSGNIHNYLAW YQQKQGKSPQLLVYNGQTLAEGVPSKFSGSGSGTQ YSLKINSLQPEDFGSYFCHQYFYFPLTFGTGTKLE IKR (86) |
| No. 0492 | DVQLVESGGGLVQPGGSRKLSCAASGFTFSSFGMHWV RQAPEKGLEWVAYISSGSSTIYYADTVKGRFTISRDN PKNTLFLQMASLRSEDTAMYYCARSYYGNFGFAMDYW GQGTSVTVSS (87) | DVVMTQTPLTLSVTIGQPASISCKSSQSLLYTQGK TYLNWLLQRPGQSPKRLIYLVSKLDSGVPDRFSGS GSGTDFTLKISRVEAEDLGVYYCLQSTHFPLTFGA GTKLELKR (88) |
| No. 0493 | DVQLVESGGGLVQPGGSRKLSCAASGFTFSTFGMHWV RQTPERGLEWVAYISSDSSNIYYADPVKGRFTISRDN PKKTLFLQMTGLRSEDTAIYYCARDGFGNYWFAYWGQ GTLVTVSA (89) | DIQMTQSPASLSATVGETVTITCRTSGNIHNYLAW YQQKQGKSPQLLVYNGQTLAEGVPSKFSGSGSGTQ YSLKINSLQPEDFGSYFCHQYFYFPLTFGTGTKLE IKR (90) |

-continued

| clone | heavy chain variable domain amino acid sequence (SEQ ID NO:) | light chain variable domain amino acid sequence (SEQ ID NO:) |
|---|---|---|
| No. 0494 | EVQLQQSGAVLVKPGASVKLSCPASGFNIKDTYIHWV IQRPEQGLEWIGRIDPANGDTKCDPKFQVKATITADT SSNTAYLQLSSLTSEDTAVYFCVRDYLYPYYFDFWGQ GTTLTVSS (91) | KIVMTQSPKSMSMSVGERVTLNCRASESVDTYVSW YQQKPEQSPELLIYGASNRYTGVPDRFTGSGSATD FTLTISSVQAEDLADYYCGQTYNYPLTFGAGTKLE LKR (92) |
| No. 0495 | EVQLQQSGPELVKPGASVKMSCRASGYSFPSYVVHWV KQKPGQGLEWIGYINPYTDGTEYNEKFKGKATLTSDK SSSTAYMELSSLTSEDSAVYYCARGFYYYSMDYWGQG TSVTVSS (93) | QIVLTQSPAIMSASPGEKVTLTCSANSSIRNMHWY QQKTGTSPKRWIYDTSNLASGVPSRFSGSGSGTSY SLTISSMEAEDAATYYCHQRSSFPYTFGGGTKLEI KR (94) |
| No. 0496 | QVQLIQSGAELVRPGASVNLSCKASGYTFTDYYINWV KQRPGQGLEWIARIYPGSDITYYNEKFKGKATLTAEK SSSTAYMQLSSLTSEDSAVYFCARSPPHYVGNRYYAL DYWGQGTSVTVSS (95) | DIQMTQSSSSFSVSLGDRVTVTCKTTEDIYNRLAW YQHKPGNAPRLLISGATGLETGVPSRFSGSGSGKD YTLTITSLQTEDVATYYCLQYWSTPYTFGGGTKLE IKR (96) |
| No. 0497 | QVQLQQPGAEFVKPGASVKMSCKASGYTFTSYWITWV KQRPGQGLEWIGDIYPGSGSNKYNEKFKSKATLTVDT SSSTAYMHLSSLTSEDSAVYYCARERPTYYGSSAWFD YWGQGTLVTVSA (97) | DIKMTQSPSSMYASLGERVTITCKASQDINSYLNW FQQKPGKSPKTLIYRANRLVDGVPSRFSGSGSGQD YSLTISSLDYEDMGIYYCLQYDEFPYTFGGGTKLE IKR (98) |

One aspect as reported herein is a humanized anti-transferrin receptor antibody or transferrin receptor binding fragment thereof comprising (1) a humanized heavy chain variable domain derived from the heavy chain variable domain that has the amino acid sequence of SEQ ID NO: 13 and a humanized light chain variable domain derived from the light chain variable domain that has the amino acid sequence of SEQ ID NO: 14, or (2) a humanized heavy chain variable domain derived from the heavy chain variable domain that has the amino acid sequence of SEQ ID NO: 15 and a humanized light chain variable domain derived from the light chain variable domain that has the amino acid sequence of SEQ ID NO: 16, or (3) a humanized heavy chain variable domain derived from the heavy chain variable domain that has the amino acid sequence of SEQ ID NO: 17 and a humanized light chain variable domain derived from the light chain variable domain that has the amino acid sequence of SEQ ID NO: 18, or (4) a humanized heavy chain variable domain derived from the heavy chain variable domain that has the amino acid sequence of SEQ ID NO: 19 and a humanized light chain variable domain derived from the light chain variable domain that has the amino acid sequence of SEQ ID NO: 20, or (5) a humanized heavy chain variable domain derived from the heavy chain variable domain that has the amino acid sequence of SEQ ID NO: 21 and a humanized light chain variable domain derived from the light chain variable domain that has the amino acid sequence of SEQ ID NO: 22, or (6) a humanized heavy chain variable domain derived from the heavy chain variable domain that has the amino acid sequence of SEQ ID NO: 23 and a humanized light chain variable domain derived from the light chain variable domain that has the amino acid sequence of SEQ ID NO: 24, or (7) a humanized heavy chain variable domain derived from the heavy chain variable domain that has the amino acid sequence of SEQ ID NO: 25 and a humanized light chain variable domain derived from the light chain variable domain that has the amino acid sequence of SEQ ID NO: 26, or (8) a humanized heavy chain variable domain derived from the heavy chain variable domain that has the amino acid sequence of SEQ ID NO: 27 and a humanized light chain variable domain derived from the light chain variable domain that has the amino acid sequence of SEQ ID NO: 28, or (9) a humanized heavy chain variable domain derived from the heavy chain variable domain that has the amino acid sequence of SEQ ID NO: 29 and a humanized light chain variable domain derived from the light chain variable domain that has the amino acid sequence of SEQ ID NO: 30, or

(10) a humanized heavy chain variable domain derived from the heavy chain variable domain that has the amino acid sequence of SEQ ID NO: 31 and a humanized light chain variable domain derived from the light chain variable domain that has the amino acid sequence of SEQ ID NO: 32, or

(11) a humanized heavy chain variable domain derived from the heavy chain variable domain that has the amino acid sequence of SEQ ID NO: 33 and a humanized light chain variable domain derived from the light chain variable domain that has the amino acid sequence of SEQ ID NO: 34, or

(12) a humanized heavy chain variable domain derived from the heavy chain variable domain that has the amino acid sequence of SEQ ID NO: 35 and a humanized light chain variable domain derived from the light chain variable domain that has the amino acid sequence of SEQ ID NO: 36, or

(13) a humanized heavy chain variable domain derived from the heavy chain variable domain that has the amino acid sequence of SEQ ID NO: 37 and a humanized light chain variable domain derived from the light chain variable domain that has the amino acid sequence of SEQ ID NO: 38, or

(14) a humanized heavy chain variable domain derived from the heavy chain variable domain that has the amino acid sequence of SEQ ID NO: 39 and a humanized light chain variable domain derived from the light chain variable domain that has the amino acid sequence of SEQ ID NO: 40, or

(15) a humanized heavy chain variable domain derived from the heavy chain variable domain that has the amino acid sequence of SEQ ID NO: 41 and a humanized light chain variable domain derived from the light chain variable domain that has the amino acid sequence of SEQ ID NO: 42, or

(16) a humanized heavy chain variable domain derived from the heavy chain variable domain that has the amino acid sequence of SEQ ID NO: 43 and a humanized light chain variable domain derived from the light chain variable domain that has the amino acid sequence of SEQ ID NO: 44, or

(17) a humanized heavy chain variable domain derived from the heavy chain variable domain that has the amino acid sequence of SEQ ID NO: 45 and a humanized light chain variable domain derived from the light chain variable domain that has the amino acid sequence of SEQ ID NO: 46, or

(18) a humanized heavy chain variable domain derived from the heavy chain variable domain that has the amino acid sequence of SEQ ID NO: 47 and a humanized light chain variable domain derived from the light chain variable domain that has the amino acid sequence of SEQ ID NO: 48, or

(19) a humanized heavy chain variable domain derived from the heavy chain variable domain that has the amino acid sequence of SEQ ID NO: 49 and a humanized light chain variable domain derived from the light chain variable domain that has the amino acid sequence of SEQ ID NO: 50, or

(20) a humanized heavy chain variable domain derived from the heavy chain variable domain that has the amino acid sequence of SEQ ID NO: 51 and a humanized light chain variable domain derived from the light chain variable domain that has the amino acid sequence of SEQ ID NO: 52, or

(21) a humanized heavy chain variable domain derived from the heavy chain variable domain that has the amino acid sequence of SEQ ID NO: 53 and a humanized light chain variable domain derived from the light chain variable domain that has the amino acid sequence of SEQ ID NO: 54, or

(22) a humanized heavy chain variable domain derived from the heavy chain variable domain that has the amino acid sequence of SEQ ID NO: 55 and a humanized light chain variable domain derived from the light chain variable domain that has the amino acid sequence of SEQ ID NO: 56, or

(23) a humanized heavy chain variable domain derived from the heavy chain variable domain that has the amino acid sequence of SEQ ID NO: 57 and a humanized light chain variable domain derived from the light chain variable domain that has the amino acid sequence of SEQ ID NO: 58, or

(24) a humanized heavy chain variable domain derived from the heavy chain variable domain that has the amino acid sequence of SEQ ID NO: 59 and a humanized light chain variable domain derived from the light chain variable domain that has the amino acid sequence of SEQ ID NO: 60, or

(25) a humanized heavy chain variable domain derived from the heavy chain variable domain that has the amino acid sequence of SEQ ID NO: 61 and a humanized light chain variable domain derived from the light chain variable domain that has the amino acid sequence of SEQ ID NO: 62, or

(26) a humanized heavy chain variable domain derived from the heavy chain variable domain that has the amino acid sequence of SEQ ID NO: 63 and a humanized light chain variable domain derived from the light chain variable domain that has the amino acid sequence of SEQ ID NO: 64, or

(27) a humanized heavy chain variable domain derived from the heavy chain variable domain that has the amino acid sequence of SEQ ID NO: 65 and a humanized light chain variable domain derived from the light chain variable domain that has the amino acid sequence of SEQ ID NO: 66, or

(28) a humanized heavy chain variable domain derived from the heavy chain variable domain that has the amino acid sequence of SEQ ID NO: 67 and a humanized light chain variable domain derived from the light chain variable domain that has the amino acid sequence of SEQ ID NO: 68, or

(29) a humanized heavy chain variable domain derived from the heavy chain variable domain that has the amino acid sequence of SEQ ID NO: 69 and a humanized light chain variable domain derived from the light chain variable domain that has the amino acid sequence of SEQ ID NO: 70, or

(30) a humanized heavy chain variable domain derived from the heavy chain variable domain that has the amino acid sequence of SEQ ID NO: 71 and a humanized light chain variable domain derived from the light chain variable domain that has the amino acid sequence of SEQ ID NO: 72, or

(31) a humanized heavy chain variable domain derived from the heavy chain variable domain that has the amino acid sequence of SEQ ID NO: 73 and a humanized light chain variable domain derived from the light chain variable domain that has the amino acid sequence of SEQ ID NO: 74, or

(32) a humanized heavy chain variable domain derived from the heavy chain variable domain that has the amino acid sequence of SEQ ID NO: 75 and a humanized light chain variable domain derived from the light chain variable domain that has the amino acid sequence of SEQ ID NO: 76, or

(33) a humanized heavy chain variable domain derived from the heavy chain variable domain that has the amino acid sequence of SEQ ID NO: 77 and a humanized light chain variable domain derived from the light chain variable domain that has the amino acid sequence of SEQ ID NO: 78, or

(34) a humanized heavy chain variable domain derived from the heavy chain variable domain that has the amino acid sequence of SEQ ID NO: 79 and a humanized light chain variable domain derived from the light chain variable domain that has the amino acid sequence of SEQ ID NO: 80, or

(35) a humanized heavy chain variable domain derived from the heavy chain variable domain that has the amino acid sequence of SEQ ID NO: 81 and a humanized light chain variable domain derived from the light chain variable domain that has the amino acid sequence of SEQ ID NO: 82, or

(36) a humanized heavy chain variable domain derived from the heavy chain variable domain that has the amino acid sequence of SEQ ID NO: 83 and a humanized light chain variable domain derived from the light chain variable domain that has the amino acid sequence of SEQ ID NO: 84, or

(37) a humanized heavy chain variable domain derived from the heavy chain variable domain that has the amino acid sequence of SEQ ID NO: 85 and a humanized light chain variable domain derived from the light chain variable domain that has the amino acid sequence of SEQ ID NO: 86, or

(38) a humanized heavy chain variable domain derived from the heavy chain variable domain that has the amino acid sequence of SEQ ID NO: 87 and a humanized light chain variable domain derived from the light chain variable domain that has the amino acid sequence of SEQ ID NO: 88, or

(39) a humanized heavy chain variable domain derived from the heavy chain variable domain that has the amino acid sequence of SEQ ID NO: 89 and a humanized light chain variable domain derived from the light chain variable domain that has the amino acid sequence of SEQ ID NO: 90, or

(40) a humanized heavy chain variable domain derived from the heavy chain variable domain that has the amino acid sequence of SEQ ID NO: 91 and a humanized light chain variable domain derived from the light chain variable domain that has the amino acid sequence of SEQ ID NO: 92.

(41) a humanized heavy chain variable domain derived from the heavy chain variable domain that has the amino acid sequence of SEQ ID NO: 93 and a humanized light chain variable domain derived from the light chain variable domain that has the amino acid sequence of SEQ ID NO: 94, or

(42) a humanized heavy chain variable domain derived from the heavy chain variable domain that has the amino acid sequence of SEQ ID NO: 95 and a humanized light chain variable domain derived from the light chain variable domain that has the amino acid sequence of SEQ ID NO: 96, or

(43) a humanized heavy chain variable domain derived from the heavy chain variable domain that has the amino acid sequence of SEQ ID NO: 97 and a humanized light chain variable domain derived from the light chain variable domain that has the amino acid sequence of SEQ ID NO: 98.

One preferred aspect as reported herein is a humanized anti-transferrin receptor antibody or transferrin receptor binding fragment thereof comprising a humanized heavy chain variable domain derived from the heavy chain variable domain that has the amino acid sequence of SEQ ID NO: 23 and a humanized light chain variable domain derived from the light chain variable domain that has the amino acid sequence of SEQ ID NO: 24.

One aspect as reported herein is a humanized anti-human transferrin receptor antibody comprising (a) a HVR-H1 comprising the amino acid sequence of SEQ ID NO: 109; (b) a HVR-H2 comprising the amino acid sequence of SEQ ID NO: 110; and (c) a HVR-H3 comprising the amino acid sequence of SEQ ID NO: 112. In one embodiment the antibody further comprises (d) a HVR-L1 comprising the amino acid sequence of SEQ ID NO: 113; (e) a HVR-L2 comprising the amino acid sequence of SEQ ID NO: 114; and (f) a HVR-L3 comprising the amino acid sequence of SEQ ID NO: 115.

One aspect as reported herein is a humanized anti-human transferrin receptor antibody comprising (a) a HVR-H1 comprising the amino acid sequence of SEQ ID NO: 109; (b) a HVR-H2 comprising the amino acid sequence of SEQ ID NO: 111; and (c) a HVR-H3 comprising the amino acid sequence of SEQ ID NO: 112. In one embodiment the antibody further comprises (d) a HVR-L1 comprising the amino acid sequence of SEQ ID NO: 113; (e) a HVR-L2 comprising the amino acid sequence of SEQ ID NO: 114; and (f) a HVR-L3 comprising the amino acid sequence of SEQ ID NO: 115.

In one aspect, the invention provides an anti-transferrin receptor antibody comprising at least one, two, three, four, five, or six HVRs selected from (a) a HVR-H1 comprising the amino acid sequence of SEQ ID NO: 109; (b) a HVR-H2 comprising the amino acid sequence of SEQ ID NO: 110; (c) a HVR-H3 comprising the amino acid sequence of SEQ ID NO: 112; (d) a HVR-L1 comprising the amino acid sequence of SEQ ID NO: 113; (e) a HVR-L2 comprising the amino acid sequence of SEQ ID NO: 114; and (f) a HVR-L3 comprising the amino acid sequence of SEQ ID NO: 115.

In one aspect, the invention provides an antibody comprising at least one, at least two, or all three VH HVR sequences selected from (a) a HVR-H1 comprising the amino acid sequence of SEQ ID NO: 109; (b) a HVR-H2 comprising the amino acid sequence of SEQ ID NO: 110; and (c) a HVR-H3 comprising the amino acid sequence of SEQ ID NO: 112. In one embodiment, the antibody comprises a HVR-H3 comprising the amino acid sequence of SEQ ID NO: 112. In another embodiment, the antibody comprises a HVR-H3 comprising the amino acid sequence of SEQ ID NO: 112 and a HVR-L3 comprising the amino acid sequence of SEQ ID NO: 115. In a further embodiment, the antibody comprises a HVR-H3 comprising the amino acid sequence of SEQ ID NO: 112, a HVR-L3 comprising the amino acid sequence of SEQ ID NO: 115, and a HVR-H2 comprising the amino acid sequence of SEQ ID NO: 111. In a further embodiment, the antibody comprises (a) a HVR-H1 comprising the amino acid sequence of SEQ ID NO: 109; (b) a HVR-H2 comprising the amino acid sequence of SEQ ID NO: 111; and (c) a HVR-H3 comprising the amino acid sequence of SEQ ID NO: 112.

In another aspect, the invention provides an antibody comprising at least one, at least two, or all three VL HVR sequences selected from (a) a HVR-L1 comprising the amino acid sequence of SEQ ID NO: 113; (b) a HVR-L2 comprising the amino acid sequence of SEQ ID NO: 114; and (c) a HVR-L3 comprising the amino acid sequence of SEQ ID NO: 115. In one embodiment, the antibody comprises (a) a HVR-L1 comprising the amino acid sequence of SEQ ID NO: 113; (b) a HVR-L2 comprising the amino acid sequence of SEQ ID NO: 114; and (c) a HVR-L3 comprising the amino acid sequence of SEQ ID NO: 115.

In another aspect, an antibody of the invention comprises (a) a VH domain comprising at least one, at least two, or all three VH HVR sequences selected from (i) a HVR-H1 comprising the amino acid sequence of SEQ ID NO: 109, (ii) a HVR-H2 comprising the amino acid sequence of SEQ ID NO: 110, and (iii) a HVR-H3 comprising an amino acid sequence selected from SEQ ID NO: 112; and (b) a VL domain comprising at least one, at least two, or all three VL HVR sequences selected from (i) a HVR-L1 comprising the amino acid sequence of SEQ ID NO: 113, (ii) a HVR-L2 comprising the amino acid sequence of SEQ ID NO: 114, and (c) a HVR-L3 comprising the amino acid sequence of SEQ ID NO: 115.

In another aspect, the invention provides an antibody comprising (a) a HVR-H1 comprising the amino acid sequence of SEQ ID NO: 109; (b) a HVR-H2 comprising the amino acid sequence of SEQ ID NO: 110; (c) a HVR-H3 comprising the amino acid sequence of SEQ ID NO: 112; (d) a HVR-L1 comprising the amino acid sequence of SEQ ID NO: 113; (e) a HVR-L2 comprising the amino acid sequence of SEQ ID NO: 114; and (f) a HVR-L3 comprising an amino acid sequence selected from SEQ ID NO: 115.

One preferred aspect as reported herein is a humanized anti-transferrin receptor antibody or transferrin receptor binding fragment thereof comprising a humanized heavy chain variable domain derived from the heavy chain variable domain that has the amino acid sequence of SEQ ID NO: 91 and a humanized light chain variable domain derived from the light chain variable domain that has the amino acid sequence of SEQ ID NO: 92.

One aspect as reported herein is a humanized anti-human transferrin receptor antibody comprising (a) a HVR-H1 comprising the amino acid sequence of SEQ ID NO: 116; (b) a HVR-H2 comprising the amino acid sequence of SEQ ID NO: 117; and (c) a HVR-H3 comprising the amino acid sequence of SEQ ID NO: 119. In one embodiment the antibody further comprises (d) a HVR-L1 comprising the amino acid sequence of SEQ ID NO: 120; (e) a HVR-L2 comprising the amino acid sequence of SEQ ID NO: 121; and (f) a HVR-L3 comprising the amino acid sequence of SEQ ID NO: 122.

One aspect as reported herein is a humanized anti-human transferrin receptor antibody comprising (a) a HVR-H1 comprising the amino acid sequence of SEQ ID NO: 116; (b) a HVR-H2 comprising the amino acid sequence of SEQ ID NO: 118; and (c) a HVR-H3 comprising the amino acid sequence of SEQ ID NO: 119. In one embodiment the antibody further comprises (d) a HVR-L1 comprising the amino acid sequence of SEQ ID NO: 120; (e) a HVR-L2 comprising the amino acid sequence of SEQ ID NO: 121; and (f) a HVR-L3 comprising the amino acid sequence of SEQ ID NO: 122.

In one aspect, the invention provides an anti-transferrin receptor antibody comprising at least one, two, three, four, five, or six HVRs selected from (a) a HVR-H1 comprising the amino acid sequence of SEQ ID NO: 116; (b) a HVR-H2 comprising the amino acid sequence of SEQ ID NO: 117; (c) a HVR-H3 comprising the amino acid sequence of SEQ ID NO: 119; (d) a HVR-L1 comprising the amino acid sequence of SEQ ID NO: 120; (e) a HVR-L2 comprising the amino acid sequence of SEQ ID NO: 121; and (f) a HVR-L3 comprising the amino acid sequence of SEQ ID NO: 122.

In one aspect, the invention provides an antibody comprising at least one, at least two, or all three VH HVR sequences selected from (a) a HVR-H1 comprising the amino acid sequence of SEQ ID NO: 116; (b) a HVR-H2 comprising the amino acid sequence of SEQ ID NO: 117; and (c) a HVR-H3 comprising the amino acid sequence of SEQ ID NO: 119. In one embodiment, the antibody comprises a HVR-H3 comprising the amino acid sequence of SEQ ID NO: 119. In another embodiment, the antibody comprises a HVR-H3 comprising the amino acid sequence of SEQ ID NO: 119 and a HVR-L3 comprising the amino acid sequence of SEQ ID NO: 122. In a further embodiment, the antibody comprises a HVR-H3 comprising the amino acid sequence of SEQ ID NO: 119, a HVR-L3 comprising the amino acid sequence of SEQ ID NO: 122, and a HVR-H2 comprising the amino acid sequence of SEQ ID NO: 118. In a further embodiment, the antibody comprises (a) a HVR-H1 comprising the amino acid sequence of SEQ ID NO: 116; (b) a HVR-H2 comprising the amino acid sequence of SEQ ID NO: 118; and (c) a HVR-H3 comprising the amino acid sequence of SEQ ID NO: 119.

In another aspect, the invention provides an antibody comprising at least one, at least two, or all three VL HVR sequences selected from (a) a HVR-L1 comprising the amino acid sequence of SEQ ID NO: 120; (b) a HVR-L2 comprising the amino acid sequence of SEQ ID NO: 121; and (c) a HVR-L3 comprising the amino acid sequence of SEQ ID NO: 122. In one embodiment, the antibody comprises (a) a HVR-L1 comprising the amino acid sequence of SEQ ID NO: 120; (b) a HVR-L2 comprising the amino acid sequence of SEQ ID NO: 121; and (c) a HVR-L3 comprising the amino acid sequence of SEQ ID NO: 122.

In another aspect, an antibody of the invention comprises (a) a VH domain comprising at least one, at least two, or all three VH HVR sequences selected from (i) a HVR-H1 comprising the amino acid sequence of SEQ ID NO: 116, (ii) a HVR-H2 comprising the amino acid sequence of SEQ ID NO: 117, and (iii) a HVR-H3 comprising an amino acid sequence selected from SEQ ID NO: 119; and (b) a VL domain comprising at least one, at least two, or all three VL HVR sequences selected from (i) a HVR-L1 comprising the amino acid sequence of SEQ ID NO: 120, (ii) a HVR-L2 comprising the amino acid sequence of SEQ ID NO: 121, and (c) a HVR-L3 comprising the amino acid sequence of SEQ ID NO: 122.

In another aspect, the invention provides an antibody comprising (a) a HVR-H1 comprising the amino acid sequence of SEQ ID NO: 116; (b) a HVR-H2 comprising the amino acid sequence of SEQ ID NO: 117; (c) a HVR-H3 comprising the amino acid sequence of SEQ ID NO: 119; (d) a HVR-L1 comprising the amino acid sequence of SEQ ID NO: 120; (e) a HVR-L2 comprising the amino acid sequence of SEQ ID NO: 121; and (f) a HVR-L3 comprising an amino acid sequence selected from SEQ ID NO: 122.

One aspect as reported herein is a transferrin shuttle module comprising a full length IgG antibody as brain effector entity, a linker and one scFab as the monovalent binding entity, which binds the transferrin receptor, wherein the scFab is conjugated to the C-terminal end of the Fc-region of one of the heavy chains of the IgG antibody via the linker.

One aspect as reported herein is a transferrin shuttle module comprising a full length IgG antibody as brain effector entity, a linker and one scFv as the monovalent binding entity, which binds the transferrin barrier receptor, wherein the scFv is conjugated to the C-terminal end of the Fc-region of one of the heavy chains of the IgG antibody via the linker.

In one preferred embodiment the monovalent binding entity comprises the HVRs of SEQ ID NOs: 109, 110, 112, 113, 114, and 115, or of SEQ ID NOs: 116, 117, 119, 120, 121, and 122.

In a further aspect, an anti-transferrin receptor antibody according to any of the above embodiments may incorporate any of the features, singly or in combination, as described in Sections 1-6 below:

1. Antibody Affinity

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 µg/mL of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µL/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/mL (~0.2 µM) before injection at a flow rate of 5 µL/minute to achieve approximately 10 response units (RU) of coupled protein. Following the injection of antigen, 1 M ethanolamine is injected to block non-reacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. No. 5,571,894 and U.S. Pat. No. 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. No. 5,821,337, U.S. Pat. No. 7,527,791, U.S. Pat. No. 6,982,321, and U.S. Pat. No. 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front.

Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

5. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for the transferrin receptor and the other is for any other antigen. Bispecific antibodies may also be used to localize cytotoxic agents to cells which express the transferrin receptor. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies", are also included herein (see, e.g. US 2006/0025576).

The antibody or fragment herein also includes a "Dual Acting Fab" or "DAF" comprising an antigen binding site that binds to the transferrin receptor as well as another, different antigen (see, US 2008/0069820, for example).

The antibody or fragment herein also includes multispecific antibodies described in WO 2009/080251, WO 2009/080252, WO 2009/080253, WO 2009/080254, WO2010/112193, WO2010/115589, WO2010/136172, WO2010/145792, and WO 2010/145793.

In one embodiment of all aspects as reported herein the anti-transferrin receptor antibody is a bispecific antibody.

One aspect as reported herein is a bivalent, bispecific antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other, wherein the first antigen or the second antigen is human transferrin receptor.

The antibody under a) does not contain a modification as reported under b) and the heavy chain and the light chain under a) are isolated chains.

In the antibody under b) within the light chain
the variable light chain domain VL is replaced by the variable heavy chain domain VH of said antibody,
and
within the heavy chain, the variable heavy chain domain VH is replaced by the variable light chain domain VL of said antibody.

In one embodiment i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid, or ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In one preferred embodiment i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one embodiment in the constant domain CL of the second heavy chain the amino acids at position 124 and 123 are substituted by K (numbering according to Kabat EU index).

In one embodiment in the constant domain CH1 of the second light chain the amino acids at position 147 and 213 are substituted by E (numbering according to EU index of Kabat).

In one preferred embodiment in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one embodiment in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

One aspect as reported herein is a bivalent, bispecific antibody comprising
 a) a first light chain and a first heavy chain of an antibody specifically binding to a first antigen, and
 b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other,
wherein the first antigen or the second antigen is human transferrin receptor.

The antibody under a) does not contain a modification as reported under b) and the heavy chain and the light chain under a) are isolated chains.

In the antibody under b) within the light chain
the variable light chain domain VL is replaced by the variable heavy chain domain VH of said antibody, and the constant light chain domain CL is replaced by the constant heavy chain domain CH1 of said antibody;

and
within the heavy chain, the variable heavy chain domain VH is replaced by the variable light chain domain VL of said antibody, and the constant heavy chain domain CH1 is replaced by the constant light chain domain CL of said antibody.

One aspect as reported herein is a bivalent, bispecific antibody comprising
 a) a first light chain and a first heavy chain of an antibody specifically binding to a first antigen, and
 b) a second light chain and a second heavy chain of an antibody specifically binding to a second antigen, wherein the constant domains CL and CH1 of the second light chain and the second heavy chain are replaced by each other,
wherein the first antigen or the second antigen is human transferrin receptor.

The antibody under a) does not contain a modification as reported under b) and the heavy chain and the light chain under a) are isolated chains.

In the antibody under b)
 within the light chain the constant light chain domain CL is replaced by the constant heavy chain domain CH1 of said antibody;
 and within the heavy chain, the constant heavy chain domain CH1 is replaced by the constant light chain domain CL of said antibody.

One aspect as reported herein is a multispecific antibody comprising
 a) a full length antibody specifically binding to a first antigen and consisting of two antibody heavy chains and two antibody light chains, and
 b) one, two, three or four single chain Fab fragments specifically binding to one to four further antigens (i.e. a second and/or third and/or fourth and/or fifth antigen, preferably specifically binding to one further antigen, i.e. a second antigen),
wherein said single chain Fab fragments under b) are fused to said full length antibody under a) via a peptidic linker at the C- or N-terminus of the heavy or light chain of said full length antibody,
wherein the first antigen or one of the further antigens is human transferrin receptor.

In one embodiment one or two identical single chain Fab fragments binding to a second antigen are fused to said full length antibody via a peptidic linker at the C-terminus of the heavy or light chains of said full length antibody.

In one embodiment one or two identical single chain Fab fragments binding to a second antigen are fused to said full length antibody via a peptidic linker at the C-terminus of the heavy chains of said full length antibody.

In one embodiment one or two identical single chain Fab fragments binding to a second antigen are fused to said full length antibody via a peptidic linker at the C-terminus of the light chains of said full length antibody.

In one embodiment two identical single chain Fab fragments binding to a second antigen are fused to said full length antibody via a peptidic linker at the C-terminus of each heavy or light chain of said full length antibody.

In one embodiment two identical single chain Fab fragments binding to a second antigen are fused to said full length antibody via a peptidic linker at the C-terminus of each heavy chain of said full length antibody.

In one embodiment two identical single chain Fab fragments binding to a second antigen are fused to said full length antibody via a peptidic linker at the C-terminus of each light chain of said full length antibody.

One aspect as reported herein is a trivalent, bispecific antibody comprising
- a) a full length antibody specifically binding to a first antigen and consisting of two antibody heavy chains and two antibody light chains,
- b) a first polypeptide consisting of
  - ba) an antibody heavy chain variable domain (VH), or
  - bb) an antibody heavy chain variable domain (VH) and an antibody constant domain 1 (CH1),
  - wherein said first polypeptide is fused with the N-terminus of its VH domain via a peptidic linker to the C-terminus of one of the two heavy chains of said full length antibody,
- c) a second polypeptide consisting of
  - ca) an antibody light chain variable domain (VL), or
  - cb) an antibody light chain variable domain (VL) and an antibody light chain constant domain (CL),
  - wherein said second polypeptide is fused with the N-terminus of the VL domain via a peptidic linker to the C-terminus of the other of the two heavy chains of said full length antibody,
  and
- wherein the antibody heavy chain variable domain (VH) of the first polypeptide and the antibody light chain variable domain (VL) of the second polypeptide together form an antigen-binding site specifically binding to a second antigen,
  and
- wherein the first antigen or the second antigen is human transferrin receptor.

In one embodiment the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
- i) heavy chain variable domain position 44 to light chain variable domain position 100, or
- ii) heavy chain variable domain position 105 to light chain variable domain position 43, or
- iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-59; Kobayashi, H., et al., Nuclear Medicine & Biology, Vol. 25, (1998) 387-393; or Schmidt, M., et al., Oncogene (1999) 18 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to EU index of Kabat). In one embodiment a trivalent, bispecific antibody without said optional disulfide stabilization between the variable domains VH and VL of the single chain Fab fragments is preferred.

One aspect as reported herein is a trispecific or tetraspecific antibody, comprising
- a) a first light chain and a first heavy chain of a full length antibody which specifically binds to a first antigen, and
- b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
- c) wherein one to four antigen binding peptides which specifically bind to one or two further antigens (i.e. to a third and/or fourth antigen) are fused via a peptidic linker to the C- or N-terminus of the light chains or heavy chains of a) and/or b), wherein the first antigen or the second antigen or one of the further antigens is human transferrin receptor.

The antibody under a) does not contain a modification as reported under b) and the heavy chain and the light chain under a) are isolated chains.

In one embodiment the trispecific or tetraspecific antibody comprises under c) one or two antigen binding peptides which specifically bind to one or two further antigens.

In one embodiment the antigen binding peptides are selected from the group of a scFv fragment and a scFab fragment.

In one embodiment the antigen binding peptides are scFv fragments.

In one embodiment the antigen binding peptides are scFab fragments.

In one embodiment the antigen binding peptides are fused to the C-terminus of the heavy chains of a) and/or b).

In one embodiment the trispecific or tetraspecific antibody comprises under c) one or two antigen binding peptides which specifically bind to one further antigen.

In one embodiment the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one embodiment the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

One aspect as reported herein is a bispecific, tetravalent antibody comprising
- a) two light chains and two heavy chains of an antibody, which specifically bind to a first antigen (and comprise two Fab fragments),
- b) two additional Fab fragments of an antibody, which specifically bind to a second antigen, wherein said additional Fab fragments are fused both via a peptidic linker either to the C- or N-termini of the heavy chains of a),
and
wherein in the Fab fragments the following modifications were performed
  - i) in both Fab fragments of a), or in both Fab fragments of b), the variable domains VL and VH are replaced by each other, and/or the constant domains CL and CH1 are replaced by each other, or
ii) in both Fab fragments of a) the variable domains VL and VH are replaced by each other, and the constant domains CL and CH1 are replaced by each other, and
in both Fab fragments of b) the variable domains VL and VH are replaced by each other, or the constant domains CL and CH1 are replaced by each other,
or
iii) in both Fab fragments of a) the variable domains VL and VH are replaced by each other, or the constant domains CL and CH1 are replaced by each other, and
in both Fab fragments of b) the variable domains VL and VH are replaced by each other, and the constant domains CL and CH1 are replaced by each other,
or
iv) in both Fab fragments of a) the variable domains VL and VH are replaced by each other, and in both Fab fragments of b) the constant domains CL and CH1 are replaced by each other,
or
v) in both Fab fragments of a) the constant domains CL and CH1 are replaced by each other, and in both Fab fragments of b) the variable domains VL and VH are replaced by each other,
wherein the first antigen or the second antigen is human transferrin receptor.

In one embodiment said additional Fab fragments are fused both via a peptidic linker either to the C-termini of the heavy chains of a), or to the N-termini of the heavy chains of a).

In one embodiment said additional Fab fragments are fused both via a peptidic linker either to the C-termini of the heavy chains of a).

In one embodiment said additional Fab fragments are fused both via a peptide connector to the N-termini of the heavy chains of a).

In one embodiment in the Fab fragments the following modifications are performed:
i) in both Fab fragments of a), or in both Fab fragments of b), the variable domains VL and VH are replaced by each other, and/or the constant domains CL and CH1 are replaced by each other.

In one embodiment in the Fab fragments the following modifications are performed:
i) in both Fab fragments of a) the variable domains VL and VH are replaced by each other, and/or
the constant domains CL and CH1 are replaced by each other.

In one embodiment in the Fab fragments the following modifications are performed:
i) in both Fab fragments of a) the constant domains CL and CH1 are replaced by each other.

In one embodiment in the Fab fragments the following modifications are performed:
i) in both Fab fragments of b) the variable domains VL and VH are replaced by each other, and/or
the constant domains CL and CH1 are replaced by each other.

In one embodiment in the Fab fragments the following modifications are performed:
i) in both Fab fragments of b) the constant domains CL and CH1 are replaced by each other.

One aspect as reported herein is a bispecific, tetravalent antibody comprising:
a) a (modified) heavy chain of a first antibody, which specifically binds to a first antigen and comprises a first VH-CH1 domain pair, wherein to the C-terminus of said heavy chain the N-terminus of a second VH-CH1 domain pair of said first antibody is fused via a peptidic linker,
b) two light chains of said first antibody of a),
c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
d) two (modified) light chains of said second antibody of c), each comprising a CL-CH1 domain pair,
wherein the first antigen or the second antigen is human transferrin receptor.

One aspect as reported herein is a bispecific antibody comprising
a) the heavy chain and the light chain of a first full length antibody that specifically binds to a first antigen, and
b) the heavy chain and the light chain of a second full length antibody that specifically binds to a second antigen, wherein the N-terminus of the heavy chain is connected to the C-terminus of the light chain via a peptidic linker,
wherein the first antigen or the second antigen is human transferrin receptor.

The antibody under a) does not contain a modification as reported under b) and the heavy chain and the light chain are isolated chains.

One aspect as reported herein is a bispecific antibody comprising
a) a full length antibody specifically binding to a first antigen and consisting of two antibody heavy chains and two antibody light chains, and
b) an Fv fragment specifically binding to a second antigen comprising a $VH^2$ domain and a $VL^2$ domain, wherein both domains are connected to each other via a disulfide bridge,
wherein only either the $VH^2$ domain or the $VL^2$ domain is fused via a peptidic linker to the heavy or light chain of the full length antibody specifically binding to a first antigen,
wherein the first antigen or the second antigen is human transferrin receptor.

In the bispecific the heavy chains and the light chains under a) are isolated chains.

In one embodiment the other of the $VH^2$ domain or the $VL^2$ domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one embodiment of all aspects the antibody as reported herein is a multispecific antibody, which requires heterodimerization of at least two heavy chain polypeptides, and wherein the antibody specifically binds to human transferrin receptor and a second non-human transferrin receptor antigen.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment of the invention, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in a multispecific antibody according to the invention, which comprises a "non-crossed Fab region" derived from a first antibody, which specifically binds to a first antigen, and a "crossed Fab region" derived from a second antibody, which specifically binds to a second antigen, in combination with the particular amino acid substitutions described above for the invention.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

But also other knobs-in-holes technologies as described by EP 1 870 459A1, can be used alternatively or additionally. In one embodiment the multispecific antibody as reported herein comprises the R409D and K370E mutations in the CH3 domain of the "knobs chain" and the D399K and E357K mutations in the CH3 domain of the "hole-chain" (numbering according to Kabat EU index).

In one embodiment the multispecific antibody as reported herein comprises a T366W mutation in the CH3 domain of the "knobs chain" and the T366S, L368A and Y407V mutations in the CH3 domain of the "hole chain" and additionally the R409D and K370E mutations in the CH3 domain of the "knobs chain" and the D399K and E357K mutations in the CH3 domain of the "hole chain" (numbering according to the Kabat EU index).

In one embodiment the multispecific antibody as reported herein comprises the Y349C and T366W mutations in one of the two CH3 domains and the S354C, T366S, L368A and Y407V mutations in the other of the two CH3 domains, or the multispecific antibody as reported herein comprises the Y349C and T366W mutations in one of the two CH3 domains and the S354C, T366S, L368A and Y407V mutations in the other of the two CH3 domains and additionally the R409D and K370E mutations in the CH3 domain of the "knobs chain" and the D399K and E357K mutations in the CH3 domain of the "hole chain" (numbering according to the Kabat EU index).

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a multispecific antibody as reported herein.

In one embodiment of a multispecific antibody as reported herein the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, this embodiment relates to a multispecific antibody as reported herein, wherein in the tertiary structure of the antibody the CH3 domain of the first heavy chain and the CH3 domain of the second heavy chain form an interface that is located between the respective antibody CH3 domains, wherein the respective amino acid sequences of the CH3 domain of the first heavy chain and the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The multispecific antibody according to this embodiment is herein also referred to as "CH3(+/−)-engineered multispecific antibody" (wherein the abbreviation "+/−" stands for the oppositely charged amino acids that were introduced in the respective CH3 domains).

In one embodiment of said CH3(+/−)-engineered multi-specific antibody as reported herein the positively charged amino acid is selected from K, R and H, and the negatively charged amino acid is selected from E or D.

In one embodiment of said CH3(+/−)-engineered multi-specific antibody as reported herein the positively charged amino acid is selected from K and R, and the negatively charged amino acid is selected from E or D.

In one embodiment of said CH3(+/−)-engineered multi-specific antibody as reported herein the positively charged amino acid is K, and the negatively charged amino acid is E.

In one embodiment of said CH3(+/−)-engineered multi-specific antibody as reported herein in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one embodiment of a multispecific antibody as reported herein the approach described in WO2013/157953 is used to support heterodimerization of the first heavy chain and the second heavy chain of the multispecific antibody. In one embodiment of said multispecific antibody as reported herein, in the CH3 domain of one heavy chain the amino acid T at position 366 is substituted by K, and in the CH3 domain of the other heavy chain the amino acid L at position 351 is substituted by D (numbering according to Kabat EU index). In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another embodiment of said multispecific antibody as reported herein, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one embodiment of a multispecific antibody as reported herein the approach described in WO2012/058768 is used to support heterodimerization of the first heavy chain and the second heavy chain of the multispecific antibody. In one embodiment of said multispecific antibody as reported herein, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:

substituting the amino acid T at position 411 by an amino acid selected from N, R, Q, K, D, E and W (numbering according to Kabat EU index), substituting the amino acid D at position 399 by an amino acid selected from R, W, Y, and K (numbering according to Kabat EU index), substituting the amino acid S at position 400 by an amino acid selected from E, D, R and K (numbering according to Kabat EU index), substituting the amino acid F at position 405 by an amino acid selected from I, M, T, S, V and W (numbering according to Kabat EU index;

substituting the amino acid N at position 390 by an amino acid selected from R, K and D (numbering according to Kabat EU index; and substituting the amino acid K at position 392 by an amino acid selected from V, M, R, L, F and E (numbering according to Kabat EU index).

In another embodiment of said multispecific antibody as reported herein (engineered according to WO2012/058768), in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of said multispecific antibody as reported herein, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In said last aforementioned embodiment, in the CH3 domain of said other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one embodiment of a multispecific antibody as reported herein the approach described in WO 2011/143545 is used to support heterodimerization of the first heavy chain and the second heavy chain of the multispecific antibody. In one embodiment of said multispecific antibody as reported herein, amino acid modifications in the CH3 domains of both heavy chains are introduced at positions 368 and/or 409 (numbering according to Kabat EU index).

In one embodiment of a multispecific antibody as reported herein the approach described in WO 2011/090762 is used to support heterodimerization of the first heavy chain and the second heavy chain of the multispecific antibody. WO 2011/090762 relates to amino acid modifications according to the "knob-into-hole" technology. In one embodiment of said CH3(KiH)-engineered multispecific antibody as reported herein, in the CH3 domain of one heavy chain the amino acid T at position 366 is substituted by W, and in the CH3 domain of the other heavy chain the amino acid Y at position 407 is substituted by A (numbering according to Kabat EU index). In another embodiment of said CH3 (KiH)-engineered multispecific antibody as reported herein, in the CH3 domain of one heavy chain the amino acid T at position 366 is substituted by Y, and in the CH3 domain of the other heavy chain the amino acid Y at position 407 is substituted by T (numbering according to Kabat EU index).

In one embodiment of a multispecific antibody as reported herein, which is of IgG2 isotype, the approach described in WO 2011/090762 is used to support heterodimerization of the first heavy chain and the second heavy chain of the multispecific antibody.

In one embodiment of a multispecific antibody as reported herein, the approach described in WO 2009/089004 is used to support heterodimerization of the first heavy chain and the second heavy chain of the multispecific antibody. In one embodiment of said multispecific antibody as reported herein, in the CH3 domain of one heavy chain the amino acid K or N at position 392 is substituted by a negatively charged amino acid (in one preferred embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one preferred embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one preferred embodiment by E or D, in one preferred embodiment by D) (numbering according to Kabat EU index). In one even further embodiment, in addition to or alternatively to the aforementioned substitutions, in the CH3 domain of the one heavy chain the amino acid K at position 439 and/or the amino acid K at position 370 is substituted independently from each other by a negatively charged amino acid (in one preferred embodiment by E or D, in one preferred embodiment by D) (numbering according to Kabat EU index).

In one embodiment of a multispecific antibody as reported herein, the approach described in WO 2007/147901 is used to support heterodimerization of the first heavy chain and the second heavy chain of the multispecific antibody. In one embodiment of said multispecific antibody as reported herein, in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

In one embodiment of a multispecific antibody as reported herein, the approach described in WO 2007/110205 is used to support heterodimerization of the first heavy chain and the second heavy chain of the multispecific antibody In one embodiment of all aspects and embodiments as reported herein the multispecific antibody is a bispecific antibody or a trispecific antibody. In one preferred embodiment of the invention the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibody variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006) 1759-1769).

Antibodies with reduced effector function include those with substitution of one or more of Fc-region residues 238, 265, 269, 270, 297, 327, and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371, 826).

See also Duncan, A. R. and Winter, G., Nature 322 (1988) 738-740; U.S. Pat. No. 5,648,260; U.S. Pat. No. 5,624,821; and WO 94/29351 concerning other examples of Fc-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or non-branched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-transferrin receptor antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-transferrin receptor antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-transferrin receptor antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-transferrin receptor antibodies provided herein may be identified, screened for, or characterized for their physical/chemical properties and/or biological activities by various assays known in the art.

1. Binding Assay

In one aspect, an antibody of the invention is tested for its antigen binding activity, e.g., by known methods such as ELISA, alphaLISA, Western blot, antibody or reverse phase array, etc.

In an exemplary ELISA or alphaLISA assay, transferrin receptor in solution (cell supernatant, cell or tissue lysates, body fluids etc.) is bound by a capture antibody, which specifically binds to a first epitope on the transferrin receptor, or transferrin receptor in a certain conformation and a detection antibody coupled to a detection entity, which specifically binds to a second epitope or conformation of the transferrin receptor. The readout is based on the detection entity (chemiluminescence, fluorescence, energy transfer induced luminescence etc.).

In the case of antibody array, antibodies are spotted onto glass or nitrocellulose chips. The slides are blocked and incubated with transferrin receptor containing solution, washed to remove unbound antibodies and bound antibodies are detected with a fluorescently labeled corresponding secondary antibody. The fluorescence signal is measured by a fluorescence slide scanner. Similarly, for a reverse phase array, recombinant transferrin receptor, cell supernatant, cell or tissue lysates, body fluids etc. are spotted onto glass or nitrocellulose chips. The slides are blocked and individual arrays are incubated with an antibody against a specific epitope on the transferrin receptor. Unbound antibodies are washed off and bound antibodies are detected with a fluorescently labeled corresponding secondary antibody. The fluorescence signal is measured by a fluorescence slide scanner (Dernick, G., et al., J. Lipid Res. 52 (2011) 2323-2331).

D. Methods and Compositions for Diagnostics and Detection

In certain embodiments, any of the anti-transferrin receptor antibodies provided herein is useful for detecting the presence of human transferrin receptor in a biological sample. The term "detecting" as used herein encompasses quantitative or qualitative detection.

In certain embodiments, a biological sample comprises a cell or tissue, such as brain tissue.

In one embodiment, an anti-transferrin receptor antibody for use in a method of diagnosis or detection is provided. In a further aspect, a method of detecting the presence of the transferrin receptor in a biological sample is provided. In certain embodiments, the method comprises contacting the biological sample with an anti-transferrin receptor antibody as described herein under conditions permissive for binding of the anti-transferrin receptor antibody to the transferrin receptor, and detecting whether a complex is formed between the anti-transferrin receptor antibody and the transferrin receptor. Such method may be an in vitro or in vivo method. In one embodiment, an anti-transferrin receptor antibody is used to select subjects eligible for therapy with an anti-transferrin receptor antibody, e.g. where the transferrin receptor is a biomarker for selection of patients.

Exemplary disorders that may be diagnosed using an antibody of the invention include neurodegeneration with brain iron accumulation type 1 (NBIA1), pure autonomic failure, Down's syndrome, complex of Guam, and several Lewy body disorders, such as diffuse Lewy body disease (DLBD), the Lewy body variant of Alzheimer's disease (LBVAD), certain forms of Gaucher's disease, and Parkinson's Disease dementia (PDD).

In certain embodiments, labeled anti-transferrin receptor antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-transferrin receptor antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone);

amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-transferrin receptor antibody.

VI. Examples

The following are examples of methods and compositions of the invention. It is understood that various other embodiments may be practiced, given the general description provided above.

Materials and Methods
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Example 1

Immunization of Rabbits and Mice

Immunization of Mice

NMRI mice were immunized genetically, using a plasmid expression vector coding for full-length human or cynomolgus TfR by intradermal application of 100 µg vector DNA, followed by electroporation (2 square pulses of 1000 V/cm, duration 0.1 ms, interval 0.125 s; followed by 4 square pulses of 287.5 V/cm, duration 10 ms, interval 0.125 s. Mice received either 6 or 7 consecutive immunizations at days 0, 14, 28, 42, 56, 70, and 84. The fourth and sixth immunizations were performed with vector coding for cynomolgus TfR; vector coding for human TfR was used for all other immunizations. Blood was taken at days 36, 78 and 92 and serum prepared, which was used for titer determination by ELISA (see below). Animals with highest titers were selected for boosting at day 96, by intravenous injection of either $10^6$ human TF-1 cells or 50 μg of recombinant human soluble TfR lacking the helical domain (extracellular domain of the human TfR beginning at Leu122, ending at Asn608, expressed in HEK293F cells as an N-terminal fusion to human Fc-region and purified by protein A affinity chromatography and size exclusion chromatography, and monoclonal antibodies were isolated by hybridoma technology, based on their ability to bind human and cynomolgus transferrin receptor expressed on the surface of stably transfected CHO-K1 cells (see Example 4).

Immunization of Rabbits

New Zealand White rabbits or transgenic rabbits expressing a humanized antibody repertoire were immunized genetically, using a plasmid expression vector coding for full-length human or cynomolgus TfR, by intradermal application of 400 μg vector DNA, followed by electroporation (5 square pulses of 750 V/cm, duration 10 ms, interval 1 s.). Rabbits received 6 consecutive immunizations at days 0, 14, 28, 56, 84 and 112. The fourth and sixth immunizations were performed with vector coding for cynomolgus TfR; vector coding for human TfR was used for all other immunizations. Blood (10% of estimated total blood volume) was taken at days 35, 63, 91 and 119. Serum was prepared, which was used for titer determination by ELISA (see below), and peripheral mononuclear cells were isolated, which were used as a source of antigen-specific B cells in the B cell cloning process (see Example 2).

Determination of Serum Titers (ELISA)

Human recombinant soluble TfR (R&D Systems Cat. No. 2474-TR) was immobilized on a 96-well NUNC Maxisorb plate at 3 μg/mL, 100 μL/well, in PBS, followed by: blocking of the plate with 2% CroteinC in PBS, 200 μL/well; application of serial dilutions of antisera, in duplicates, in 0.5% CroteinC in PBS, 100 μL/well; detection with (1) HRP-conjugated goat anti-mouse antibody (Jackson Immunoresearch/Dianova 115-036-071; 1/16 000) for all mouse sera, (2) HRP-conjugated donkey anti-rabbit IgG antibody (Jackson Immunoresearch/Dianova 711-036-152; 1/16 000) for all rabbit sera, (3) rabbit anti-human IgG antibody (Pierce/Thermo Scientific 31423; 1/5000) for sera from transgenic rabbits only, (4) biotinylated goat anti-human kappa antibody (Southern Biotech/Biozol 2063-08, 1/5 000) and streptavidin-HRP for sera from transgenic rabbits only; diluted in 0.5% CroteinC in PBS, 100 μL/well. For all steps, plates were incubated for 1 h at 37° C. Between all steps, plates were washed 3 times with 0.05% Tween 20 in PBS. Signal was developed by addition of BM Blue POD Substrate soluble (Roche), 100 μL/well; and stopped by addition of 1 M HCl, 100 μL/well. Absorbance was read out at 450 nm, against 690 nm as reference. Titer was defined as dilution of antisera resulting in half-maximal signal.

Example 2

B-Cell Cloning from Rabbits

Isolation of Rabbit Peripheral Blood Mononuclear Cells (PBMC)

Blood samples were taken of in summary 6 animals (2 wild-type (wt) rabbits and 4 transgenic (tg) rabbits). These rabbits derived from 2 different immunization campaigns: first campaign with 2 wt and 2 tg rabbits and second campaign with 2 tg rabbits (see also the example "Immunization of rabbits"). EDTA containing whole blood was diluted twofold with 1×PBS (PAA, Pasching, Austria) before density centrifugation using lymphocyte mammal (Cedarlane Laboratories, Burlington, Ontario, Canada) according to the specifications of the manufacturer. The PBMCs were washed twice with 1×PBS.

EL-4 B5 Medium

RPMI 1640 (Pan Biotech, Aidenbach, Germany) supplemented with 10% FCS (Hyclone, Logan, Utah, USA), 2 mM glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland)

Depletion of Cells

First immunization campaign: Sterile 6-well plates (cell culture grade) covered with a confluent monolayer of CHO cells were used to deplete macrophages/monocytes through unspecific adhesion as well as non-specifically binding lymphocytes.

Second immunization campaign: The depletion step using wells covered with CHO cells was omitted since we could not exclude those B-cells producing antibodies that are cross-reactive to hamster transferrin receptor antibodies would be depleted. Therefore, blank sterile 6-well plates (cell culture grade) were used to deplete macrophages and monocytes through unspecific adhesion enabling potential B-lymphocytes producing hamster cross-reactive (and possibly mouse cross-reactive) surface antibodies to reach the next step in the workflow.

For each immunization campaign: each well was filled at maximum with 4 mL medium and up to $6 \times 10^6$ PBMCs from the immunized rabbit and allowed to bind for 1 h at 37° C. in the incubator. The cells in the supernatant (peripheral blood lymphocytes (PBLs)) were used for the antigen panning step.

Enrichment of B-Cells on the Human Transferrin Receptor 6-well tissue culture plates covered with a monolayer of human transferrin receptor-positive CHO cells were seeded with up to $6 \times 10^6$ PBLs per 4 mL medium and allowed to bind for 1 h at 37° C. in the incubator. Non-adherent cells were removed by carefully washing the wells 1-2 times with 1×PBS. The remaining sticky cells were detached by trypsin for 10 min. at 37° C. in the incubator. Trypsination was stopped with EL-4 B5 medium. The cells were kept on ice until the immune fluorescence staining.

Immune Fluorescence Staining and Flow Cytometry

The anti-IgG FITC (AbD Serotec, Düsseldorf, Germany) was used for single cell sorting. For surface staining, cells from the depletion and enrichment step were incubated with the anti-IgG FITC antibody in PBS and incubated for 45 min. in the dark at 4° C. After staining the PBMCs were washed two fold with ice cold PBS. Finally, the PBMCs were resuspended in ice cold PBS and immediately subjected to the FACS analyses. Propidium iodide in a concentration of 5 μg/mL (BD Pharmingen, San Diego, Calif., USA) was added prior to the FACS analyses to discriminate between dead and live cells.

A Becton Dickinson FACSAria equipped with a computer and the FACSDiva software (BD Biosciences, USA) were used for single cell sort.

B-Cell Cultivation

The cultivation of the rabbit B-cells was prepared by a method similar to that described by Zubler et al. (1985). Briefly, single sorted rabbit B-cells were incubated in 96-well plates with 200 μL/well EL-4 B5 medium containing Pansorbin Cells (1:100000) (Calbiochem (Merck), Darmstadt, Deutschland), 5% rabbit thymocyte supernatant (charge TSN-M13 (10242), MicroCoat, Bernried, Germany) and gamma-irradiated murine EL-4-B5 thymoma cells ($2.5 \times 10^4$/well) for 7 days at 37° C. in an atmosphere of 5% $CO_2$ in the incubator. The supernatants of the B-cell cultivation were removed for screening and the remaining cells were harvested immediately and were frozen at −80° C. in 100 µL RLT buffer (Qiagen, Hilden, Germany).

Example 3

Phage Display for Selection and Production of Monovalent Anti-TfR IgGs

Selection by Phage Display

Generation of antibodies binding to human and cynomolgus TfR was carried out by phage display using standard protocols (Silacci et al, *Proteomics*, 5 (2005) 2340-2350). A synthesized gene for hTfR-Fc(KiH)-Avi (KiH=knobs-into-holes, Avi=AviTag) antigen was cloned by connecting the hTfR ECD to the N-terminal hinge of a human hole Fc-region, which carried a C-terminal Avi-tag (SEQ ID NO: 99), and ligation into a mammalian expression vector. All our mammalian expression vectors carry a MPSV promoter for initiation of transcription and translation, where transcription is terminated by a synthetic polyA signal sequence located downstream of the ORF. In addition, the vector contains an EBV oriP sequence for autonomous replication in EBV-EBNA expressing cell lines. The correct ORF was verified by sequencing. This vector was used for expression in HEK293 EBNA suspension cells, by co-expression with an empty knob-Fc-region and the BirA protein, and adding 1 mM of biotin to the culture medium. The resulting biotinylated protein was purified by protein A affinity chromatography, followed by size exclusion chromatography. The cyTfR-Fc(KiH)-Avi antigen was produced respectively (SEQ ID NO: 100).

The library used was a fully synthetic library using human frameworks of the VH1, 3, 4, and 5 families, as well as V-kappa1, -2, and -3, and V-lambda3. Randomized aminoacids were in CDR-H3 and CDR-L3. Library pools were generated, using each heavy chain VH together with all different light chain libraries. Selections were carried out in solution according to the following procedure: 1. binding of approx. $10^{12}$ phageimid particles of each library to 100 nM biotinylated TfR-avi-his for 0.5 h in a total volume of 1 mL, 2. capture of biotinylated TfR-avi-his and specifically bound phage particles by addition of $5.4 \times 10^7$ streptavidin-coated magnetic beads for 10 min., 3. washing of beads using 5-10×1 mL PBS/Tween 20 and 5-10×1 mL PBS, 4. elution of phage particles by addition of 1 mL 100 mM TEA (triethylamine) for 10 min. and neutralization by adding 500 µL 1 M Tris/HCl pH 7.4 and 5. Re-infection of exponentially growing *E. coli* TG1 bacteria, infection with helper phage VCSM13 and subsequent PEG/NaCl precipitation of phageimid particles to be used in subsequent selection rounds. Selections were carried out over 3-5 rounds using either constant or decreasing (from $10^{-7}$ M to $2 \times 10^{-9}$ M) antigen concentrations. In round 2, capture of antigen/phage complexes was performed using neutravidin plates instead of streptavidin beads. Since the binders generated against the recombinant soluble antigen often showed only weak binding on cells, we introduced two additional selection steps using cells displaying the native antigen after the second or third round of enrichment on the recombinant antigen. Here, the two cell-lines TF-1, and NCI-H460 were used (both available from ATCC). In brief, $1*10^6$ cells were incubated with approx. $10^{12}$ phage particles for 1 h on ice to avoid receptor mediated internalization. Washing was performed by 5-10 centrifugation steps using PBST buffer (PBS containing 1% Tween-20). Entire cells were used to infect the TG1 bacteria for phage rescue.

Specific binders were identified by ELISA as follows: 100 µL of 10 nM biotinylated TfR-avi-his per well were coated on neutravidin plates. Fab-containing bacterial supernatants were added and binding Fabs were detected via their FLAG-tags by using an anti-FLAG/HRP secondary antibody. ELISA-positive clones were bacterially expressed as soluble Fab fragments in 96-well format and supernatants were subjected to a kinetic screening experiment by SPR-analysis using ProteOn XPR36 (BioRad). Clones expressing Fabs with the highest affinity constants were identified and the corresponding phageimids were sequenced.

Purification of Fab Antibodies

Top 10 cells were individually transfected with the phage-imid plasmid of all cell ELISA positive clones. The cells were grown in media and production of Fab antibodies was induced. Fab antibodies were isolated by periplasmic preparation and purified using IMAC.

FACS Analysis

Purified Fab antibodies were applied to TF-1 cells in various concentrations. Cell bound Fab antibodies were detected using a fluorescent labeled anti-Fab antibody and measurements by FACS. EC50 values were calculated.

Production and Characterization of the Selected Clones

Conversion into the IgG Format

Selected clones with a complex half live (t½) between 6 to 20 minutes or an $EC_{50}$ on cells between 10 nM and 500 nM, with a distinct cell binding signal either on FACS or cell ELISA, and cross-reactive binding against both the hTfR-Fc(KiH)-Avi and the cyTfR-Fc(KiH)-Avi antigen were chosen for conversion into the IgG format.

Therefore, the VL domain was amplified by PCR and cloned into a mammalian expression vector, as described above, directly upstream of a CL domain. In addition, the VH domain was amplified by PCR and cloned directly upstream of a CH-Fc domain. The sequences of both expression vectors were determined.

Production of IgG Antibodies

HEK293 EBNA suspension cells were transfected with both, the LC and HC encoding, plasmids and cultivated for 7 days. The supernatant was cleared by sterile filtration. IgG concentration was determined by protein A chromatography.

Determination of EC50 Using the TagLite Technology

The gene of the ECD of hTfR or cyTfR, respectively, including the transmembrane domain was ligated downstream to SNAP-tag into a mammalian expression vector. This vector was used to transfect HEK293 EBNA suspension cells, resulting in display of the TfR with a C-terminal SNAP tag fusion ((SEQ ID NO: 101, SEQ ID NO: 102). The SNAP tag was specifically labeled with SNAP-Lumi4Tb (Cisbio). The labeling efficiency determined by measuring the emission of Terbium at 615 nm. Labeled cells were stored at −80° C.

In presence of anti-humanFc-d2 IgG antibody, labeled cells were incubated with IgG supernatant in various dilutions and the FRET signals (emission of donor dye Lumi4Tb: 615 nM and acceptor dye d2: 665 nM) were measured after 4 hours. The $EC_{50}$ values were calculated, resulting in 25 IgGs, which bound to both hTfR and cyTfR.

Determination of Cell Binding by FACS

The gene of full-length hTfR or cyTfR, respectively, was cloned into a mammalian expression vector. This vector was used for transfection of CHO EBNA suspension cells. IgG supernatant was directly applied to the TfR displaying cells. After washing with PBST, the antigen-antibody complex was detected using an anti-huFc IgG-HRP antibody conjugate, followed by development with 3,3'-5,5'-Tetramethylbenzidine. Functional display was verified using commercially available anti-TfR antibody. All 25 TagLite positive clones exhibited a strong binding signal.

Production and Purification of Monovalent IgG Like Molecules

The VH domain was cloned into a mammalian expression vector encoding the human knob IgG1 HC, which carries the L234A, L235A, and P329G mutations. This vector was used for expression in HEK293 EBNA suspension cells, co-expressing the LC (vector described above) and an empty hole-Fc domain carrying the L234A, L235A, P329G, H435R and Y436F mutations. The resulting protein was purified by protein A affinity chromatography. In cases of monomeric protein was >95%, determined by analytical size exclusion chromatography, the protein was further purified by size exclusion chromatography.

Example 4

Identification of Human and Cynomolgus TfR-Binding Antibodies by Cell ELISA

To screen rabbit B-cell or mouse hybridoma supernatants for antibodies recognizing human and cynomolgus TfR, a cell ELISA using stably transfected CHO-K1 cells way employed. Stable transfectants were obtained by transfecting CHO-K1 cells with expression plasmids containing expression cassettes for the human or cynomolgus TfR as well as for neomycin-phosphotransferase. After transfection, cells were diluted in growth medium containing 500 µg/mL G418 (Life Technologies). After appearance of growing clones, cells were detached, stained with MEM-75 (Abcam) or 13E4 (Life Technologies) and PE-labeled secondary antibodies for human or cynomolgus TfR, and highly fluorescent cells sorted as single cells into 96-well-plate wells (FACS Aria). After 7 days of growth, clones were again checked for TfR expression and best expressing clones selected for cell ELISA experiments.

Briefly, 15,000 cells were seeded per well of a 384-well plate and incubated for 18 h at 37° C., 5% CO$_2$. Supernatant was removed using an automated washer (BIOTEK), and 30 µL of antibody-containing supernatant added to each well, followed by 24 µL of growth medium. After 2 hours of incubation, wells were emptied and 30 µL of 0.05% glutaraldehyde in PBS added for 45 min. at RT. After 3 washes with PBS/0.025% Tween20 (PBST), 30 µL of anti-rabbit-HRP or anti-mouse-HRP (Southern Biotech) diluted 1:5000 in Blocking buffer was added and plates incubated for 1 hour at RT. Wells were washed 6 times with PBST and signal was generated using 30 µL of TMB per well and absorbance measured at 450 nm.

Example 5

Cloning and Expression of Anti-TfR Antibodies

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

PCR Amplification of V-Domains

Total RNA was prepared from B-cells lysate (resuspended in RLT buffer—Qiagen—Cat. No 79216) using the NucleoSpin 8/96 RNA kit (Macherey&Nagel; 740709.4, 740698) according to manufacturer's protocol. RNA was eluted with 60 µL RNAse free water. 6 µL of RNA was used to generate cDNA by reverse transcriptase reaction using the Superscript III First-Strand Synthesis SuperMix (Invitrogen 18080-400) and an oligo-dT-primer according to the manufacturer's instructions. All steps were performed on a Hamilton ML Star System. 4 µL of cDNA were used to amplify the immunoglobulin heavy and light chain variable regions (VH and VL) with the AccuPrime SuperMix (Invitrogen 12344-040) in a final volume of 50 µL using the primers rbHC.up and rbHC.do for the heavy chain, rbLC.up and rbLC.do for the light chain of Wild Type Rabbit B cells and BcPCR_FHLC_leader.fw and BcPCR_huCkappa.rev for the light chain of transgenic rabbit B-cells (see Table below). All forward primers were specific for the signal peptide (of respectively VH and VL) whereas the reverse primers were specific for the constant regions (of respectively VH and VL). The PCR conditions for the RbVH+RbVL were as follows: Hot start at 94° C. for 5 min.; 35 cycles of 20 sec. at 94° C., 20 sec. at 70° C., 45 sec. at 68° C., and a final extension at 68° C. for 7 min. The PCR conditions for the HuVL were as follows: Hot start at 94° C. for 5 min.; 40 cycles of 20 sec. at 94° C., 20 sec. at 52° C., 45 sec. at 68° C., and a final extension at 68° C. for 7 min.

```
rbHC.up
                               (SEQ ID NO: 103)
AAGCTTGCCACCATGGAGACTGGGCTGCG
CTGGCTTC rbHCf.do
                               (SEQ ID NO: 104)
CCATTGGTGAGGGTGCCCGAG rbLC.up
                               (SEQ ID NO: 105)
AAGCTTGCCACCATGGACAYGAGGGCCCC
CACTC rbLC.do
                               (SEQ ID NO: 106)
CAGAGTRCTGCTGAGGTTGTAGGTAC

BcPCR_FHLC_leader.fw
                               (SEQ ID NO: 107)
ATGGACATGAGGGTCCCCGC BcPCR_huCkappa.rev
                               (SEQ ID NO: 108)
GATTTCAACTGCTCATCAGATGGC
```

8 µL of 50 µL PCR solution were loaded on a 48 E-Gel 2% (Invitrogen G8008-02). Positive PCR reactions were cleaned using the NucleoSpin Extract II kit (Macherey&Nagel; 740609250) according to manufacturer's protocol and eluted in 50 µL elution buffer. All cleaning steps were performed on a Hamilton ML Starlet System.

Recombinant Expression of Rabbit Monoclonal Bivalent Antibodies

For recombinant expression of rabbit monoclonal bivalent antibodies, PCR-products coding for VH or VL were cloned as cDNA into expression vectors by the overhang cloning method (R S Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Three variants of the basic plasmid were used: one plasmid containing the rabbit IgG constant region designed to accept the VH regions while two additional plasmids containing rabbit or human kappa LC constant region to accept the VL regions.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

For antibody expression, the isolated HC and LC plasmids were transiently co-transfected into HEK293 cells and the supernatants were harvested after 1 week.

Generation of Vectors for the Expression of Rabbit Monoclonal Monovalent Antibodies For recombinant expression of selected candidates as monoclonal monovalent antibodies rabbit constant regions of all VH chains were converted into human constant regions enclosing the knob-mutation in the CH3 segment. For VL chains derived from rabbit wild-type B-cells, rabbit C kappa constant regions were converted into human. 4 µL of cDNA of the selected candidates were used to amplify the immunoglobulin heavy and light chain variable regions with the AccuPrime SuperMix (Invitrogen 12344-040) in a final volume of 50 µL with forward primers specific for the signal peptide and reverse primers specific for the CDR3-J region with (at the 3' end) overlap sequence (20 bp) homologous to the human constant regions (respectively of VH and VL). The PCR conditions for the VH and VL chain amplification were as follows: Hot start at 94° C. for 5 min.; 35 cycles of 20 sec. at 94° C., 20 sec. at 68° C., 45 sec. at 68° C., and a final extension at 68° C. for 7 min.

PCR-products coding for VH or VL were cloned as cDNA into expression vectors by the overhang cloning method (R S Haun et al., BioTechniques (1992) 13, 515-518; M Z Li et al., Nature Methods (2007) 4, 251-256). The expression vectors contained an expression cassette consisting of a 5' CMV promoter including intron A, and a 3' BGH poly adenylation sequence. In addition to the expression cassette, the plasmids contained a pUC18-derived origin of replication and a beta-lactamase gene conferring ampicillin resistance for plasmid amplification in E. coli. Two variants of the basic plasmid were used: one plasmid containing the human IgG constant region designed to accept the new amplified VH chain and a second plasmid containing the human kappa LC constant region to accept the VL chain.

Linearized expression plasmids coding for the kappa or gamma constant region and VL/VH inserts were amplified by PCR using overlapping primers.

Purified PCR products were incubated with T4 DNA-polymerase which generated single-strand overhangs. The reaction was stopped by dCTP addition.

In the next step, plasmid and insert were combined and incubated with recA which induced site specific recombination. The recombined plasmids were transformed into E. coli. The next day the grown colonies were picked and tested for correct recombined plasmid by plasmid preparation, restriction analysis and DNA-sequencing.

Example 6

Transient Expression of the Monovalent Anti-TfR Antibodies

The antibodies were generated in vivo in transiently transfected HEK293 cells (human embryonic kidney cell line 293-derived) cultivated in F17 Medium (Invitrogen Corp.). For transfection "293-Free" Transfection Reagent (Novagen) was used. Antibodies and antibody-based modified molecules as described above were expressed from individual expression plasmids. Transfections were performed as specified in the manufacturer's instructions. Recombinant protein-containing cell culture supernatants were harvested three to seven days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

Example 7

Purification of One-Armed Transferrin Receptor Antibodies in High Throughput

The 50 mL clarified supernatants containing one armed antibodies in 96 deep-well plates were loaded on 200 µL MabSelectSuRe columns. After washing steps with PBS at pH 7.4, proteins were eluted with 2.5 mM HCl using Tecan/Atoll-system resulting in 0.5 mL eluate. Eluate was neutralized by 2 M Tris pH 8. Purified proteins were quantified using a Nanodrop spectrophotometer and analyzed by CE-SDS under denaturing and reducing conditions and analytical SEC. To obtain protein with high purity (>95%) a large proportion of the antibodies have to be purified further on size exclusion chromatography to separate from half antibody, knob-knob antibodies and higher aggregates. In the following 500 µL of the samples were injected on Superdex200 10/300GL in 20 mM histidine containing 140 mM NaCl pH 6.0 using Dionex UltiMate 3000. This method allows fractionating 25-30 samples/day and therefore allows polishing a large number of screening hits in one-armed format. Fractions were pooled and analyzed again as described above.

Example 8 hCMEC/D3 Cell Culture for Transcytosis Assays

Medium and supplements for hCMEC/D3 (Weksler, B. B. et al., FASEB J. 19 (2005), 1872-1874) were obtained from Lonza. hCMEC/D3 cells (passages 26-29) were cultured to confluence on collagen-coated coverslips (microscopy) or flasks in EBM2 medium containing 2.5% FBS, a quarter of the supplied growth factors and fully complemented with supplied hydrocortisone, gentamycin and ascorbic acid.

For all transcytosis assays, high density pore ($1\times10^8$ pores/cm$^2$) PET membrane filter inserts (0.4 µm, 12 mm diameter) were used in 12-well cell culture plates. Optimum media volumes were calculated to be 400 µL and 1600 µL for apical and basolateral chambers, respectively. Apical chambers of filter inserts were coated with rat tail collagen I (7.5 µg/cm$^2$) followed by fibronectin (5 µg/mL), each incubation lasting for 1 hour at RT. hCMEC/D3 cells were grown to confluent monolayers (approx. $2\times10^5$ cells/cm$^2$) for 10-12 days in EMB2 medium.

Example 9

Transcytosis Assay of Monovalent Antibodies

The entire assay was performed in serum-free EBM2 medium which was otherwise reconstituted as described in Example 1. Filter inserts with cells were incubated apically with monovalent antibodies (concentration: 2.67 µg/mL) for 1 hour at 37° C. following which the entire apical and basolateral media were collected. From these values, paracellular flux was calculated. The monolayers were washed at RT in serum-free medium apically (400 µL) and basolaterally (1600 µL) 3×3-5 min. each. All the washes were collected to monitor efficiency of removal of the unbound antibody. Pre-warmed medium was added to the apical chamber and the filters transferred to a fresh 12 well plate (blocked overnight with PBS containing 1% BSA) containing 1600 µL pre-warmed medium. At this point, cells on filters were lysed in 500 µL RIPA buffer in order to determine specific antibody uptake. The remaining filters were incubated at 37° C. and samples collected at various time points to determine apical and/or basolateral release of antibody. The content of antibody in the samples was quantified using a highly sensitive IgG ELISA (see Example 3). For each time point, data were generated from three filter cell cultures.

Example 10

Sensitive IgG ELISA after Transcytosis Assay

The entire procedure was performed at RT using an automated washer for the wash steps. A 384-well plate was coated with 30 µL/well of 1 µg/mL anti-human/mouse-IgG, Fcγ-specific in PBS for 2 hours followed by 1 hour incubation in blocking buffer PBS containing 1% BSA or 1 CroteinC for human and mouse IgG assays, respectively). Serially diluted samples from the transcytosis assay and standard concentrations of the antibody used in the transcytosis assay were added to the plate and incubated for 2 hours. After four washes, 30 µL/well of 50 ng/mL anti-human/mouse-F(ab)2-Biotin in blocking buffer was added and incubated for a further 2 hours. Following 6 washes, 30 µL/well of 50 ng/mL (huIgG assay) or 100 ng/mL (mIgG assay) Poly-HRP40-Streptavidin (Fitzgerald; in PBS containing 1% BSA and 0.05% Tween-20) was added and incubated for 30 min. After 4 washes, immune complexes were detected by addition of 30 µL/well of BM Chemiluminescence Substrate (Roche). The luminescence signal was measured using a luminescence plate reader and concentration calculated using the fitted standard curve. The sensitivity of the assay ranged from 10 pg/mL to 10 ng/mL.

Example 11

Epitope Mapping by Cell ELISA of CHO Cells Transfected with hTfR Mutants

In order to be able determine the epitope regions on human transferrin receptor (hTfR), mutations were introduced into the hTfR sequence at positions where a cluster of surface-exposed amino acids had different amino acids in the aligned mouse TfR sequence (see Table below), following the rationale that in spite of the significant homology between human and mouse TfR (77% identity), no antibodies directed to the extracellular part are known which show good cross-reactivity between both orthologous. Cloning of plasmids with the corresponding mutations is described above. To map binding of human TfR binders to those epitopes, CHO-K1 cells were transiently transfected with the described plasmids and antibody binding measured in a cell ELISA. Briefly, $10^4$ cells were plated per well of a 96-well plate the day before experiment in normal growth medium (RPMI/10% FCS). The other day, medium was changed to OPTI-MEM Serum-Reduced Medium (Gibco), and 10 µL of a mixture of 1200 µL OPTI-MEM, 12 µg plasmid DNA and 12 µL XtremeGENE transfection reagent (Roche) were added to the wells after 30 minutes of pre-incubation. Cells were incubated for 2 days at 37° C./7.5% $CO_2$, then medium was removed and TfR antibodies added at concentrations between 1 nM and 100 nM in growth medium, followed by 2 h incubation at 4° C. Afterwards, antibody solutions were replaced by 0.05% glutaraldehyde in PBS and cells fixed for 15 min. at RT, then washed twice with PBS and incubated with HRP-conjugated anti-human-Fc secondary antibody (BioRad; 1:2000 in ELISA Blocking Reagent (Roche)) for 1.5 hours at RT. Signal was generated after 3 washes with PBS using 50 µL of TMB per well and absorbance measured at 450 nm.

| Plasmid # | mutations in hTfR |
|---|---|
| 10188 | — |
| 18909 | Thr518Asp/Gln520Lys/Phe521 Ser/Gln524Arg |
| 18910 | Arg325Gln |
| 18911 | Ser355Ala/Asp356Arg/Lys358Asn/Thr359Ile |
| 18912 | Asp204Gln/Lys205Ser/Arg208Asn |
| 18913 | Lys574Gly/Glu575Ala/Ile577Thr/Glu578Gln |
| 18914 | Ala196Ile/Gln197Gly/Asn198Gln/Ser199Asn/Val200Met/Ile201Val/Ile202Thr/Val203Ile/Asp204Val/Lys205Gln/Asn206Ser/Gly207Asn/Arg208Gly/Leu209Asn/Val210Leu/Tyr211Asp/Leu212Pro |
| 18974 | Asp245Glu/Tyr247Ser/Thr248Tyr/Pro249Ser |

Example 12

Surface Plasmon Resonance-Based Binding Assay for Human TfR-Antibody Interaction The binding experiment were carried out on a BIAcore B 4000 (GE Healthcare) equipped with C1 sensorchip (GE Healthcare, cat. no. BR1005-35) pre-treated with anti-human Fab antibody (GE Healthcare, cat. no 28-9583-25) using a standard amine coupling chemistry procedure accordingly to the vendor's manual.

For kinetic measurements the sample antibody was immobilized applying a contact time of 60 seconds and a flow rate of 10 μL/min in phosphate buffer saline pH 7.4, 0.05% Tween 20 at 25° C. Recombinant His6-tagged human transferrin receptor (R&D systems, cat. no 2474-TR-050) was applied in increasing concentrations and the signal monitored over the time. An average time span of 150 seconds of association time and 600 seconds of dissociation time at 30 μL/min flow rate was recorded. Data were fit using a 1:1 binding model (Langmuir isotherm).

The invention claimed is:

1. A blood brain barrier shuttle module comprising a brain effector entity, optionally a linker and exactly one (monovalent) binding entity which binds to transferrin receptor (TfR), wherein the linker if present couples the effector entity to the monovalent binding entity, wherein the monovalent binding entity comprises an anti-TfR antibody or fragment thereof comprising (a) a HVR-H1 comprising the amino acid sequence of SEQ ID NO: 109; (b) a HVR-H2 comprising the amino acid sequence of SEQ ID NO: 110; (c) a HVR-H3 comprising the amino acid sequence of SEQ ID NO: 112; (d) a HVR-L1 comprising the amino acid sequence of SEQ ID NO: 113; (e) a HVR-L2 comprising the amino acid sequence of SEQ ID NO: 114; and (f) a HVR-L3 comprising the amino acid sequence of SEQ ID NO: 115.

2. The blood brain barrier shuttle module according to claim 1, wherein the monovalent binding entity comprises an anti-TfR antibody or fragment thereof comprising a heavy chain variable domain having the amino acid sequence of SEQ ID NO:23 and a light chain variable domain having the amino acid sequence of SEQ ID NO:24.

3. The blood brain barrier shuttle module according to claim 1, wherein the monovalent binding entity specifically binds to human transferrin receptor and to cynomolgus transferrin receptor.

4. The blood brain barrier shuttle module according to claim 1, wherein the monovalent binding entity comprises one scFab directed to the transferrin receptor.

5. The blood brain barrier shuttle module according to claim 1, wherein the monovalent binding entity comprises one scFv directed to the transferrin receptor.

6. The blood brain barrier shuttle module according to claim 1, wherein the brain effector entity is selected from the group consisting of neurological disorder drugs, neurotrophic factors, growth factors, enzymes, cytotoxic agents, antibodies directed to a brain target, monoclonal antibodies directed to a brain target.

7. The blood brain barrier shuttle module according to claim 6, wherein the brain target is selected from the group consisting of β-secretase 1, Aβ (Abeta), epidermal growth factor, epidermal growth factor receptor 2, tau, phosphorylated tau, phosphorylated tau(pS422), apolipoprotein E4, alpha synuclein, CD20, huntingtin, prion protein, parkin, presenilin 2, gamma secretase, death receptor 6, amyloid precursor protein, p75 neurotrophin receptor and caspase 6.

8. The blood brain barrier shuttle module according to claim 1, wherein the monovalent binding entity is conjugated to the C-terminal end of the brain effector entity either directly or via a linker.

9. The blood brain barrier shuttle module according to claim 1, wherein the brain effector entity comprises a full length antibody directed to a brain target.

10. A pharmaceutical formulation comprising a blood brain barrier shuttle module according to claim 1.

* * * * *